US009504756B2

(12) United States Patent
Lyon et al.

(10) Patent No.: US 9,504,756 B2
(45) Date of Patent: Nov. 29, 2016

(54) SELF-STABILIZING LINKER CONJUGATES

(71) Applicant: Seattle Genetics, Inc., Bothell, WA (US)

(72) Inventors: Robert Lyon, Sammamish, WA (US); Svetlana O. Doronina, Snohomish, WA (US); Timothy Bovee, Bothell, WA (US)

(73) Assignee: Seattle Genetics, Inc., Bothell, WA (US)

( * ) Notice: Subject to any disclaimer, the term of this patent is extended or adjusted under 35 U.S.C. 154(b) by 414 days.

(21) Appl. No.: 13/799,244

(22) Filed: Mar. 13, 2013

(65) Prior Publication Data

US 2013/0309256 A1 Nov. 21, 2013

Related U.S. Application Data

(60) Provisional application No. 61/773,067, filed on Mar. 5, 2013, provisional application No. 61/770,983, filed on Feb. 28, 2013, provisional application No. 61/647,373, filed on May 15, 2012.

(51) Int. Cl.
  *A61K 39/00* (2006.01)
  *C07K 7/02* (2006.01)
  *A61K 47/48* (2006.01)
  *C07K 5/062* (2006.01)
  *C07D 207/36* (2006.01)

(52) U.S. Cl.
  CPC ....... *A61K 47/48338* (2013.01); *C07D 207/36* (2013.01); *C07K 5/06052* (2013.01); *C07K 7/02* (2013.01)

(58) Field of Classification Search
  None
  See application file for complete search history.

(56) References Cited

U.S. PATENT DOCUMENTS

| 4,880,935 | A | 11/1989 | Thorpe |
| 5,523,360 | A | 6/1996 | Jelenic et al. |
| 5,973,166 | A | 10/1999 | Mizori et al. |
| 6,130,237 | A | 10/2000 | Denny et al. |
| 6,214,345 | B1 | 4/2001 | Firestone et al. |
| 7,498,298 | B2 | 3/2009 | Doronina et al. |
| 7,659,241 | B2 | 2/2010 | Senter et al. |
| 7,968,687 | B2 | 6/2011 | McDonagh et al. |
| 8,142,784 | B2 | 3/2012 | Ebens, Jr. et al. |
| 8,163,888 | B2 | 4/2012 | Steeves et al. |
| 8,343,928 | B2 | 1/2013 | Doronina et al. |
| 2003/0083263 | A1 | 5/2003 | Doronina et al. |
| 2005/0009751 | A1 | 1/2005 | Senter et al. |
| 2005/0238649 | A1 | 10/2005 | Doronina et al. |
| 2006/0193865 | A1 | 8/2006 | Govindan |
| 2009/0012241 | A1 | 1/2009 | Kozlowski et al. |
| 2009/0018086 | A1 | 1/2009 | Doronina et al. |
| 2009/0111756 | A1 | 4/2009 | Doronina et al. |
| 2010/0104589 | A1 | 4/2010 | Govindan et al. |
| 2011/0020343 | A1 | 1/2011 | Senter et al. |

FOREIGN PATENT DOCUMENTS

| CN | 1938046 A | 3/2007 |
| EP | 0 446 071 A2 | 9/1991 |
| WO | 02/088172 A2 | 11/2002 |
| WO | 2004/010957 A2 | 2/2004 |
| WO | 2005/112919 A2 | 12/2005 |
| WO | 2007/038658 A2 | 4/2007 |
| WO | 2009/002993 A1 | 12/2008 |
| WO | 2010/091150 A1 | 8/2010 |
| WO | 2011/023883 A1 | 3/2011 |
| WO | 2012/054748 A2 | 4/2012 |
| WO | 2012/112708 A1 | 8/2012 |
| WO | 2014/151030 A1 | 9/2014 |

OTHER PUBLICATIONS

Abstract of Hayashi et al (Peptide Science, 2006, vol. 43).*
Carey and Sundberg, 'Advanced Organic Chemistry Part B', 1977, section 1.10, pp. 24-28.*
International Search Report corresponding to PCT/US2013/040951 mailed Oct. 25, 2013, 16 pages.
Agarwal, Paresh et al., "A Pictet-Spengler ligation for protein chemical modification," *PNAS* (Jan. 2, 2013) 110(1):46-51.
Alley et al., "Contribution of Linker Stability to the Activities of Anticancer Immunoconjugates," *Bioconjugate Chem.* (2008) 19:759-765.
Badescu, George et al., "A New Reagent for Stable Thio-Specific Conjugation," *Bioconjugate Chem.* (2014) 25:460-469.
Baldwin, Aaron D. et al., "Tunable degradation of maleimide-thiol adducts in reducing environments," *Bioconjug Chem.* (Oct. 19, 2011), 22(10): 1946-1953.
Borah, H. N. et al., "Microwave-induced One-pot Synthesis of N-carboxyalkyl Maleimides and Phthalimides," *J. Chem. Research (S)* (1998), pp. 272-273.
Kalia, Jeet et al., "Catalysis of imido group hydroloysis in a maleimide conjugate," *Bioorg. Med. Chem. Lett.* (2007) 17:6286-6289.
Kalia, Jeet et al., "Advances in Bioconjugation," *Curr Org Chem.* (Jan. 2010), 14(2): 138-147.
Knight, Peter, "Hydrolysis of p-NN'-Phenylenebismaleimide and its Adducts with Cysteine," *Biochem. J.* (1979), 179:191-197.
Lyon, Robert P. et al., "Self-Stabilizing ADCs: conjugates prepared with maleimide drug-linkers that catalyze their own thiosuccinimide ring hydrolysis," Abstract No. 4333, *American Associate for Cancer Research* (Apr. 2013, Washington DC); 1 page.
Lyon, Robert P. et al. "Self-hydrolyzing maleimides improve the stability and pharmacological properties of antibody-drug conjugates," *Nature Biotechnology Letters* Advance Online Publication (2014), 7 pages.

(Continued)

Primary Examiner — Karen Canella
(74) Attorney, Agent, or Firm — Mintz, Levin, Cohn, Ferris, Glovsky and Popeo, P.C.

(57) ABSTRACT

The present invention provides Ligand-Drug Conjugates, Drug-Linkers, Linkers, and Ligand-Linker Conjugates comprising a self-stabilizing linker assembly component.

15 Claims, 14 Drawing Sheets

(56) References Cited

OTHER PUBLICATIONS

Ondrus, V. et al., "On the use of water as a solvent—simple and short one-step synthesis of maleimides," ARKIVOC (2001) pp. 60-67.

Page, Brigitte et al., "A new fluorometric assay for cytotoxicity measurements in vitro," *Intl. J. of Oncology* (1993); 3:473-476.

Rodrigues, Maria L. et al., "Synthesis and β-lactamase-mediated activation of a cephalosporin-taxol prdrug," (1995), *Chemistry Biology* 2(4):223-227.

Ryan et al., "Tunable reagents for multi-functional bioconjugation: reversible or permanent chemical modification of proteins and peptides by control of maleimide hydrolysis," *Chem. Coomun.* (2011) 47, 5452-5454.

Shen, Ben-Quan et al., "Conjugation site modulates the in vivo stability and therapeutic activity of antibody-drug conjugates," *Nature Biotechnology* (Feb. 2012), 30(2): 184-191.

Smith et al., "Protein Modification, Bioconjugation, and Disulfide Bridging Using Bromomaleimides," *J. Am. Chem. Soc.* (2010), 132(6), 1960-1965.

Walker, M.A., "The Mitsunobu Reaction: A Novel Method for the Synthesis of Bifunctional Maleimide Linkers," *Tetrahedron Letters*, (1994) 35(5):665-668.

International Preliminary Report on Patentability (Chapter I) issued Apr. 28, 2015 corresponding to PCT/US2013/040951 (13 pages).

Written Opinion, Intellectual Property Office of Singapore, mailed Aug. 14, 2015 corresponding to Singapore Patent Application No. 11201406252W (11 pages).

Extended European Search Report corresponding to EP13791383.6 dated May 26, 2016; 11 pages.

Ajaj, Khalid Abu et al., "Development of Protein-Binding Bifunctional Linkers for a New Generation of Dual-Acting Prodrugs," *Bioconjugate Chem.* (Jan. 20, 2009); 20:39-396.

Alley, Stephen C. et al., "Contribution of Linker Stability to the Activities of Anticancer Immunoconjugates," *Bioconjugate Chem.* (Mar. 4, 2008); 19:759-765.

Lyon, Robert P. et al., "Abstract 4333: Self-stabilizing ADCs: antibody-drug conjugates prepared with maleimido drug-linkers that catalyze their own thiosuccinimide ring hydrolysis," Abstract; *Cancer Research* (Apr. 15, 2013) 73(8): Suppl 1, p. 4333; Proceedings: American-Associate-For-Cancer-Research (AACR); Washington, D.C. Apr. 6-10, 2013.

Rao, Kandukuri S. P. Bhushana et al., "Vinblastine-$C_4$ Alkyl Maleoyl and Amino Acid Maleoyl Derivatives: I. Chemistry and Phsicochemical Data," *Anticancer Research* (Apr. 27, 1989) 9:619-624.

\* cited by examiner

SELF-STABILIZING LINKER CONJUGATES

This application claims the benefit of U.S. Provisional Patent Application No. 61/647,373, filed May 15, 2012, and U.S. Provisional Patent Application No. 61/773,067, filed Mar. 5, 2013, each of which is incorporated herein in its entirety and for all purposes.

BACKGROUND OF THE INVENTION

The antibody-drug conjugate (ADC) field has made significant advances with the FDA approval of Brentuximab Vedotin for the treatment of a select group of patients and with the advancement of many other ADCs in the clinic. The linker component of ADCs is one important feature in developing optimized therapeutic agents that are highly active at well tolerated doses. The electrophilic maleimide functional group has proven very useful in the preparation of ADCs due to its high degree of specificity for reacting with thiol groups and the very fast thiol addition kinetics under gentle conditions.

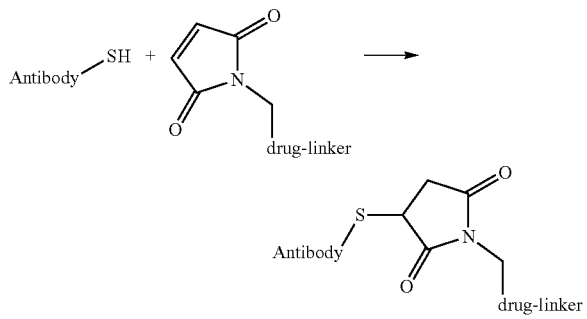

As has been noted by multiple investigators in the bioconjugate field, the thio-substituted product of the reaction between the electrophilic maleimide functional group and free thiol of antibody is subject to slow elimination, thus reversing the above reaction:

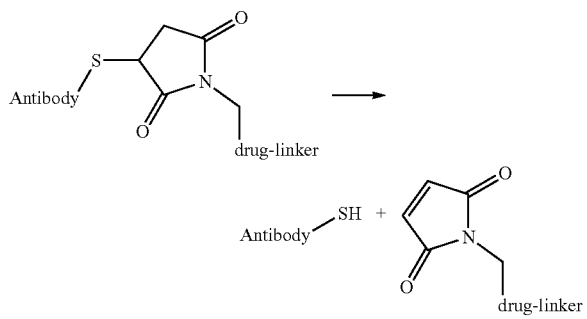

When this reversible reaction occurs in a purified preparation of the ADC, the reaction is largely undetectable because the maleimide and thiol which are regenerated through the elimination process simply react again, thus reforming the intact conjugate. However, when other thiols are present, the net effect can be the transfer of the maleimide from the antibody of the ADC onto any other available thiol. This process has been documented to occur in plasma, in which the maleimide of an ADC transfers to cysteine 34 of serum albumin (Alley et al., *Bioconjugate Chem.* 2008, 19, 759-765). This process has also been reported when an ADC is incubated in the presence of excess cysteine or glutathione (Jununtula et al., *Nature Biotech*, 2012). The present invention provides, inter alia, bioconjugates that do not undergo this transfer reaction.

BRIEF SUMMARY OF THE INVENTION

The invention provides inter alia, Linkers, Drug-Linkers, Ligand-Drug Conjugates, Ligand-Linker Conjugates, Ligand-Functional Agent Conjugates, and Functional Agent-Linkers, and methods of preparing and using them. The Ligand-Drug Conjugates are stable in circulation, yet capable of inflicting cell death once released in the vicinity or within tumor cells.

DETAILED DESCRIPTION

Abbreviations and Definitions

Figure 1A:
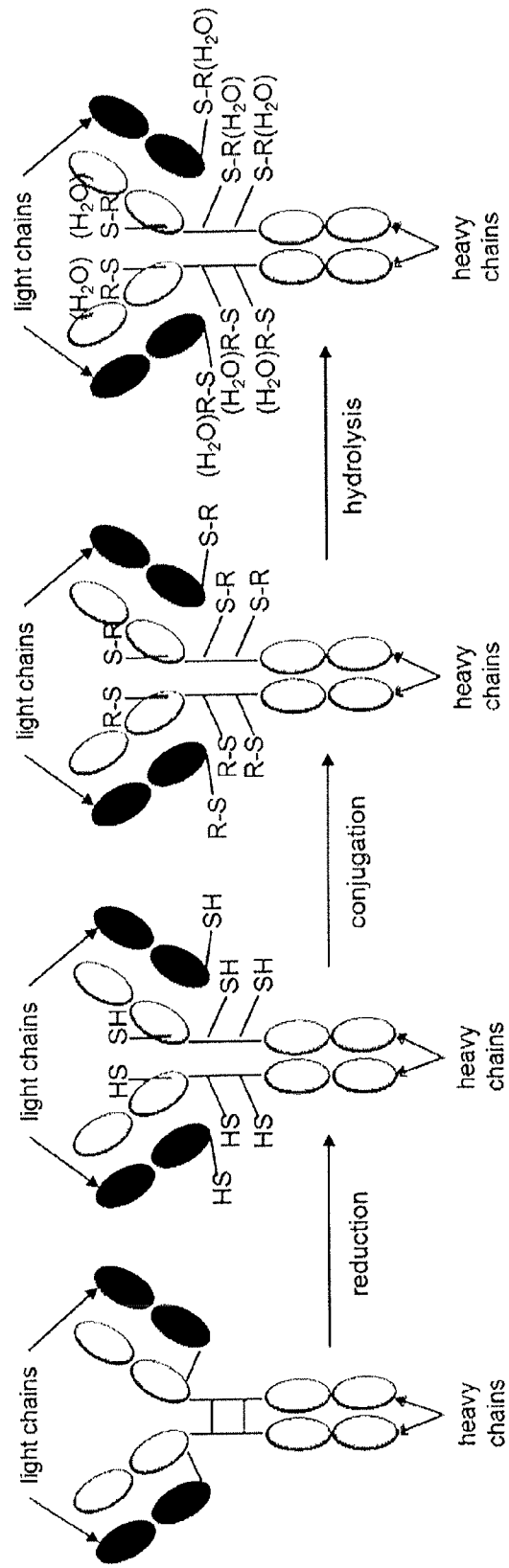
FIGS. 1A and 1B provide a reaction scheme illustrating the reduction of the interchain disulfides of a human IgG1, followed by conjugation of the resulting thiols with a self-stabilizing linker and subsequent hydrolysis of the succinimide ring (FIG. 1A); and the use of mass spectrometry to monitor the change in the molecular weight of the antibody conjugates due to hydrolysis (FIG. 1B).

Unless stated otherwise, the following terms and phrases as used herein are intended to have the following meanings. When trade names are used herein, the trade name includes the product formulation, the generic drug, and the active pharmaceutical ingredient(s) of the trade name product, unless otherwise indicated by context.

The term "electron-withdrawing group" refers to a functional group that draws electrons away from a reaction center. Exemplary electron withdrawing groups include, but are not limited to, —C(=O), —CN, —NO$_2$, —CX$_3$, —X, —COOR, —CONR$_2$, —COR, —COX, —SO$_2$R, —SO$_2$OR, —SO$_2$NHR, —SO$_2$NR$_2$, —PO$_3$R$_2$, —P(O)(CH$_3$)NHR, NO, —NR$_3^+$, —CR=CR$_2$, and —C≡CR wherein X is F, Br, Cl, or I, and R is, at each occurrence, independently selected from the group consisting of hydrogen and C$_{1-6}$ alkyl. Exemplary electron withdrawing groups can also include aryl groups (e.g., phenyl) and certain heteroaryl groups (e.g., pyridine). The term "electron withdrawing groups" includes aryls or heteroaryls further substituted with electron withdrawing groups. Preferred electron withdrawing groups are —C(=O), —CN, —NO$_2$, —CX$_3$, and —X.

The term "base" refers to a functional group that deprotonates water to produce a hydroxide ion. Exemplary bases are amines and nitrogen containing heterocycles. Representative bases include —N(R$^3$)(R$^4$) wherein R$^3$ and R$^4$ are independently selected from H or C$_{1-6}$ alkyl, preferably H or methyl,

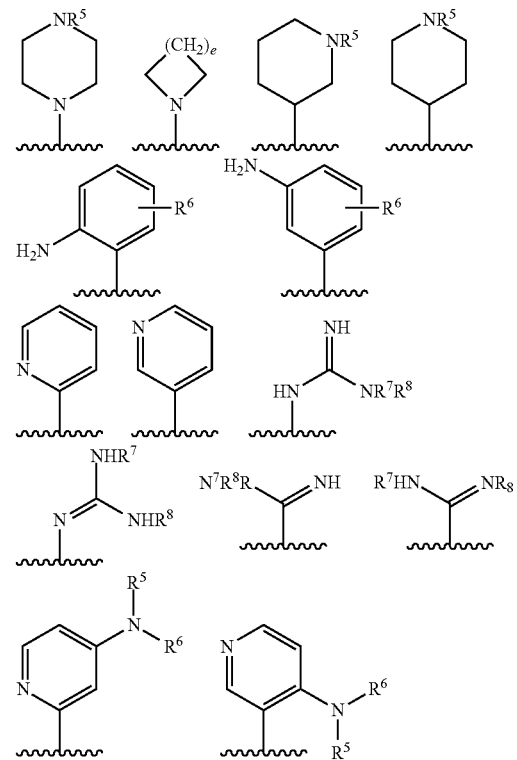

wherein R$^5$, R$^6$, R$^7$ and R$^8$ are, at each occurrence, independently selected from hydrogen or C$_{1-6}$ alkyl, preferably H or methyl, and e is 0-4. In some aspects, the base is a nitrogenous base.

The term "antibody" herein is used in the broadest sense and specifically covers intact monoclonal antibodies, polyclonal antibodies, monospecific antibodies, multispecific antibodies (e.g., bispecific antibodies), and antibody fragments that exhibit the desired biological activity. An intact antibody has primarily two regions: a variable region and a constant region. The variable region binds to and interacts with a target antigen. The variable region includes a complementary determining region (CDR) that recognizes and binds to a specific binding site on a particular antigen. The constant region may be recognized by and interact with the immune system (see, e.g., Janeway et al., 2001, *Immuno. Biology*, 5th Ed., Garland Publishing, New York). An antibody can be of any type (e.g., IgG, IgE, IgM, IgD, and IgA), class (e.g., IgG1, IgG2, IgG3, IgG4, IgA1 and IgA2) or subclass. The antibody can be derived from any suitable species. In some embodiments, the antibody is of human or murine origin. An antibody can be, for example, human, humanized or chimeric.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

An "intact antibody" is one which comprises an antigen-binding variable region as well as a light chain constant domain ($C_L$) and heavy chain constant domains, $C_H1$, $C_H2$, $C_H3$ and $C_H4$, as appropriate for the antibody class. The constant domains may be native sequence constant domains (e.g., human native sequence constant domains) or amino acid sequence variant thereof.

An "antibody fragment" comprises a portion of an intact antibody, comprising the antigen-binding or variable region thereof. Examples of antibody fragments include Fab, Fab', $F(ab')_2$, and Fv fragments, diabodies, triabodies, tetrabodies, linear antibodies, single-chain antibody molecules, scFv, scFv-Fc, multispecific antibody fragments formed from antibody fragment(s), a fragment(s) produced by a Fab expression library, or an epitope-binding fragments of any of the above which immunospecifically bind to a target antigen (e.g., a cancer cell antigen, a viral antigen or a microbial antigen).

An "antigen" is an entity to which an antibody specifically binds.

The terms "specific binding" and "specifically binds" mean that the antibody or antibody derivative will bind, in a highly selective manner, with its corresponding target antigen and not with the multitude of other antigens. Typically, the antibody or antibody derivative binds with an affinity of at least about $1 \times 10^{-7}$ M, and preferably $10^{-8}$ M to le M, $10^{-10}$ M, $10^{-11}$ M, or $10^{-12}$ M and binds to the predetermined antigen with an affinity that is at least two-fold greater than its affinity for binding to a non-specific antigen (e.g., BSA, casein) other than the predetermined antigen or a closely-related antigen.

The term "inhibit" or "inhibition of" means to a reduce by a measurable amount, or to prevent entirely.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may inhibit growth and/or kill existing cancer cells, it may be cytostatic and/or cytotoxic. For cancer therapy, efficacy can, for example, be measured by assessing the time to disease progression (TTP) and/or determining the response rate (RR).

The term "substantial" or "substantially" refers to a majority, i.e. >50% of a population, of a mixture or a sample, preferably more than 50%, 55%, 60%, 65%, 70%, 75%, 80%, 85%, 90%, 91%, 92%, 93%, 94%, 95%, 96%, 97%, 98%, or 99% of a population.

The terms "intracellularly cleaved" and "intracellular cleavage" refer to a metabolic process or reaction inside a cell on a Ligand Drug conjugate (e.g., an Antibody Drug Conjugate (ADC) or the like), whereby the covalent attachment, e.g., the linker, between the Drug moiety (D) and the Ligand unit (e.g., an antibody (Ab)) is broken, resulting in the free Drug, or other metabolite of the conjugate dissociated from the antibody inside the cell. The cleaved moieties of the Drug-Linker-Ligand conjugate are thus intracellular metabolites.

The term "cytotoxic activity" refers to a cell-killing, a cytostatic or an anti-proliferative effect of a Drug-Linker-Ligand conjugate compound or an intracellular metabolite of a Drug-Linker-Ligand conjugate. Cytotoxic activity may be expressed as the $IC_{50}$ value, which is the concentration (molar or mass) per unit volume at which half the cells survive.

The term "cytotoxic agent" as used herein refers to a substance that inhibits or inhibits the function of cells and/or causes destruction of cells. The term is intended to include radioactive isotopes (e.g., $^{211}$At, $^{131}$I, $^{125}$I, $^{90}$Y, $^{186}$Re, $^{188}$Re, $^{153}$Sm, $^{212}$Bi, $^{32}$P, $^{60}$C, and radioactive isotopes of Lu), chemotherapeutic agents, and toxins such as small molecule toxins or enzymatically active toxins of bacterial, fungal, plant or animal origin, including synthetic analogs and derivatives thereof.

The terms "cancer" and "cancerous" refer to or describe the physiological condition or disorder in mammals that is typically characterized by unregulated cell growth. A "tumor" comprises one or more cancerous cells.

An "autoimmune disease" herein is a disease or disorder arising from and directed against an individual's own tissues or proteins.

Examples of a "patient" include, but are not limited to, a human, rat, mouse, guinea pig, monkey, pig, goat, cow, horse, dog, cat, bird and fowl. In an exemplary embodiment, the patient is a human.

The terms "treat" or "treatment," unless otherwise indicated by context, refer to therapeutic treatment and prophylactic measures to prevent relapse, wherein the object is to inhibit or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder.

In the context of cancer, the term "treating" includes any or all of: inhibiting growth of tumor cells, cancer cells, or of a tumor; inhibiting replication of tumor cells or cancer cells, lessening of overall tumor burden or decreasing the number of cancerous cells, and ameliorating one or more symptoms associated with the disease.

In the context of an autoimmune disease, the term "treating" includes any or all of inhibiting replication of cells associated with an autoimmune disease state including, but not limited to, cells that produce an autoimmune antibody, lessening the autoimmune-antibody burden and ameliorating one or more symptoms of an autoimmune disease.

As used herein, the term "Detection unit" refers to refers to any molecule which produces, or can be induced to produce, a detectable signal. Detection units having reporter molecules that can be detected by imaging equipment include, but are not limited to, radioactive, paramagnetic, fluorescent or radioopaque chemical entities. In some embodiments, the Detection unit will be a radioactive compound, a chemiluminescent agent, a fluorescent agent, or a chromogen. In some embodiments, the Detection unit will be a fluorescent molecule such as a fluorophore.

As used herein, the term "Stability unit" refers to a compound that promotes the stability of the conjugate, e.g., by increasing systemic retention of the Ligand when administered to a patient. A Stability unit can also increase the water solubility of the conjugate. An exemplary Stability unit is polyethylene glycol.

The phrase "pharmaceutically acceptable salt," as used herein, refers to pharmaceutically acceptable organic or inorganic salts of a compound (e.g., a Drug, Drug-Linker, or a Ligand-Drug Conjugate). The compound can contain at least one amino group, and accordingly acid addition salts can be formed with the amino group. Exemplary salts include, but are not limited to, sulfate, trifluoroacetate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

Unless otherwise indicated, the term "alkyl" by itself or as part of another term refers to a substituted or unsubstituted straight chain or branched, saturated or unsaturated hydrocarbon having the indicated number of carbon atoms (e.g., "—$C_1$-$C_8$ alkyl" or "—$C_1$-$C_{10}$" alkyl refer to an alkyl group having from 1 to 8 or 1 to 10 carbon atoms, respectively). When the number of carbon atoms is not indicated, the alkyl group has from 1 to 8 carbon atoms. Representative straight chain "—$C_1$-$C_8$ alkyl" groups include, but are not limited to, -methyl, -ethyl, -n-propyl, -n-butyl, -n-pentyl, -n-hexyl, -n-heptyl and -n-octyl; while branched —$C_1$-$C_8$ alkyls include, but are not limited to, -isopropyl, -sec-butyl, -isobutyl, -tert-butyl, -isopentyl, and -2-methylbutyl; unsaturated —$C_2$-$C_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexyl, 2-hexyl, -3-hexyl, -acetylenyl, -propynyl, -1-butynyl, -2-butynyl, -1-pentynyl, -2-pentynyl and -3-methyl-1 butynyl. In some embodiments, an alkyl group is unsubstituted. An alkyl group can be substituted with one or more groups. In some aspects, an alkyl group will be saturated.

Unless otherwise indicated, "alkylene," by itself of as part of another term, refers to a substituted or unsubstituted saturated, branched or straight chain or cyclic hydrocarbon radical of the stated number of carbon atoms, typically 1-10 carbon atoms, and having two monovalent radical centers derived by the removal of two hydrogen atoms from the same or two different carbon atoms of a parent alkane. Typical alkylene radicals include, but are not limited to: methylene (—$CH_2$—), 1,2-ethyl (—$CH_2CH_2$—), 1,3-propyl (—$CH_2CH_2CH_2$—), 1,4-butyl (—$CH_2CH_2CH_2CH_2$—), and the like. In preferred aspects, an alkylene is a branched or straight chain hydrocarbon (i.e., it is not a cyclic hydrocarbon).

Unless otherwise indicated, "aryl," by itself or as part of another term, means a substituted or unsubstituted monovalent carbocyclic aromatic hydrocarbon radical of 6-20 carbon atoms derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, naphthalene, anthracene, biphenyl, and the like. An exemplary aryl group is a phenyl group as follows:

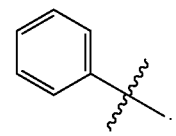

Unless otherwise indicated, an "arylene," by itself or as part of another term, is an aryl group as defined above which has two covalent bonds (i.e., it is divalent) and can be in the ortho, meta, or para configurations as shown in the following structures, with phenyl as the exemplary group:

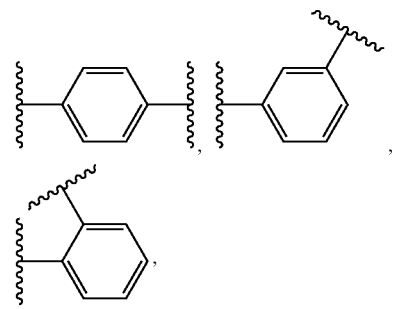

Unless otherwise indicated, a "$C_3$-$C_8$ heterocycle," by itself or as part of another term, refers to a monovalent substituted or unsubstituted aromatic or non-aromatic monocyclic or bicyclic ring system having from 3 to 8 carbon atoms (also referred to as ring members) and one to four heteroatom ring members independently selected from N, O, P or S, and derived by removal of one hydrogen atom from a ring atom of a parent ring system. One or more N, C or S atoms in the heterocycle can be oxidized. The ring that includes the heteroatom can be aromatic or nonaromatic.

Unless otherwise noted, the heterocycle is attached to its pendant group at any heteroatom or carbon atom that results in a stable structure. Representative examples of a $C_3$-$C_8$ heterocycle include, but are not limited to, pyrrolidinyl, azetidinyl, piperidinyl, morpholinyl, tetrahydrofuranyl, tetrahydropyranyl, benzofuranyl, benzothiophene, indolyl, benzopyrazolyl, pyrrolyl, thiophenyl (thiophene), furanyl, thiazolyl, imidazolyl, pyrazolyl, pyrimidinyl, pyridinyl, pyrazinyl, pyridazinyl, isothiazolyl, and isoxazolyl. A "$C_3$-$C_8$ heteroaryl," is an aromatic $C_3$-$C_8$ heterocycle.

Unless otherwise indicated, "$C_3$-$C_8$ heterocyclo," by itself or as part of another term, refers to a $C_3$-$C_8$ heterocycle group defined above wherein one of the heterocycle group's hydrogen atoms is replaced with a bond (i.e., it is divalent). A "$C_3$-$C_8$ heteroarylene," by itself or as part of another term, refers to a $C_3$-$C_8$ heteroaryl group defined above wherein one of the heteroaryl group's hydrogen atoms is replaced with a bond (i.e., it is divalent).

Unless otherwise indicated, a "$C_3$-$C_8$ carbocycle," by itself or as part of another term, is a 3-, 4-, 5-, 6-, 7- or 8-membered monovalent, substituted or unsubstituted, saturated or unsaturated non-aromatic monocyclic or bicyclic carbocyclic ring derived by the removal of one hydrogen atom from a ring atom of a parent ring system. Representative —$C_3$-$C_8$ carbocycles include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, and cyclooctadienyl.

Unless otherwise indicated, a "$C_3$-$C_8$ carbocyclo," by itself or as part of another term, refers to a $C_3$-$C_8$ carbocycle group defined above wherein another of the carbocycle groups' hydrogen atoms is replaced with a bond (i.e., it is divalent).

Unless otherwise indicated, the term "heteroalkyl," by itself or in combination with another term, means, unless otherwise stated, a stable straight or branched chain hydrocarbon, or combinations thereof, fully saturated or containing from 1 to 3 degrees of unsaturation, consisting of the stated number of carbon atoms and from one to ten, preferably one to three, heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group or at the position at which the alkyl group is attached to the remainder of the molecule. The heteroatom Si may be placed at any position of the heteroalkyl group, including the position at which the alkyl group is attached to the remainder of the molecule. Examples include —$CH_2$—$CH_2$-O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —NH—$CH_2$—$CH_2$—NH—C(O)—$CH_2$—$CH_3$, —$CH_2$—$CH_2$—S(O)$_2$—$CH_3$, —CH=CH—O—$CH_3$, —Si($CH_3$)$_3$, —$CH_2$—CH=N—O—$CH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. In preferred embodiments, a $C_1$ to $C_4$ heteroalkyl or heteroalkylene has 1 to 4 carbon atoms and 1 or 2 heteroatoms and a $C_1$ to $C_3$ heteroalkyl or heteroalkylene has 1 to 4 carbon atoms and 1 or 2 heteroatoms. In some aspects, a heteroalkyl or heteroalkylene is saturated.

Unless otherwise indicated, the term "heteroalkylene" by itself or as part of another substituent means a divalent group derived from heteroalkyl (as discussed above), as exemplified by —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini. Still further, for alkylene and heteroalkylene linking groups, no orientation of the linking group is implied.

"Substituted alkyl" and "substituted aryl" mean alkyl and aryl, respectively, in which one or more hydrogen atoms are each independently replaced with a substituent. Typical substituents include, but are not limited to, —X, —R, —$O^{31}$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, —NRC(=O)R, —C(=O)R, —C(=O)NR$_2$, —SO$_3^-$, —SO$_3$H, —S(=O)$_2$R, —OS(=O)$_2$OR, —S(=O)$_2$NR, —S(=O)R, —OP(=O)(OR)$_2$, —P(=O)(OR)$_2$, —PO$^-_3$, —PO$_3$H$_2$, —AsO$_2$H$_2$, —C(=O)R, —C(=O)X, —C(=S)R, —CO$_2$R, —CO$_2^-$, —C(=S)OR, —C(=O)SR, —C(=S)SR, —C(=O)NR$_2$, —C(=S)NR$_2$, or —C(=NR)NR$_2$, where each X is independently a halogen: —F, —Cl, —Br, or —I; and each R is independently —H, —$C_1$-$C_{20}$ alkyl, —$C_6$-$C_{20}$ aryl, —$C_3$-$C_{14}$ heterocycle, a protecting group or a prodrug moiety. Alkylene, carbocycle, carbocyclo, arylene, heteroalkyl, heteroalkylene, heterocycle, heterocyclo, heteroaryl, and heteroarylene groups as described above may also be similarly substituted.

RG is a reactive group that contains a reactive site (RS) that is capable of forming a bond with either the components of the Linker unit (i.e., A, W, Y) or the Drug unit D. RS is the reactive site within a Reactive Group (RG). Reactive groups include sulfhydryl groups to form disulfide bonds or thioether bonds, aldehyde, ketone, or hydrazine groups to form hydrazone bonds, carboxylic or amino groups to form peptide bonds, carboxylic or hydroxy groups to form ester bonds, sulfonic acids to form sulfonamide bonds, alcohols to form carbamate bonds, and amines to form sulfonamide bonds or carbamate bonds. The following table is illustrative of Reactive Groups, Reactive Sites, and exemplary functional groups that can form after reaction of the reactive site. The table is not limiting. One of skill in the art will appreciate that the noted R' and R" portions in the table are effectively any organic moiety (e.g., an alkyl group, aryl group, heteroaryl group, or substituted alkyl, aryl, or heteroaryl, group) which is compatible with the bond formation provided in converting RG to one of the Exemplary Functional Groups. It will also be appreciated that, as applied to the embodiments of the present invention, R' may represent one or more components of the self-stabilizing linker or optional secondary linker, as the case may be, and R" may represent one or more components of the optional secondary linker, drug unit, stabilizing unit, or detection unit, as the case may be.

| RG | RS | Exemplary Functional Groups |
|---|---|---|
| 1) R'—SH | —S— | R'—S—R"<br>R'—S—S—R" |
| 2) R'—C(=O)OH | —C(=O)— | R'—C(=O)NH—R" |
| 3) R'—C(=O)ONHS | —C(=O)— | R'—C(=O)NH—R" |
| 4) R'S(=O)$_2$—OH | —S(=O)$_2$— | R'S(=O)$_2$NH—R" |
| 5) R'—$CH_2$—X (X is Br, I, Cl) | —$CH_2$— | R'—$CH_2$—S—R" |
| 6) R'—NH$_2$ | —N— | R'—NHC(=O)R" |

It will be understood that, once reacted, the reactive site RS can form a new bond with components of the Linker unit or the Drug unit, as the case may be. The reactive site, RS, once linked to the remainder of the Linker unit has typically lost its reactivity.

The term "dilactam" as used herein refers to a cyclic amide that forms from a macro-cyclicization reaction with a thio-substituted succinimide and base present on the self-stabilizing linker assembly.

General

Hydrolysis of a maleimide (or thio-substituted succinimide) represents a nucleophilic addition reaction in which water, acting as the nucleophile, attacks one of the electrophilic carbonyl carbon atoms of the maleimide ring (or succinimide ring). The rate of this reaction is influenced by electrophilicity of the carbonyls, which can vary with the substitution of electron-donating or electron-withdrawing groups present on the nitrogen of the imide group. The rate of the hydrolysis reaction is also influenced by the pH of an aqueous solvent, which effectively increases the nucleophilicity of water with increasing pH. It has been discovered by the present inventors that the placement of a basic group on an N-substituted maleimide also increases the rate of the hydrolysis. By careful engineering of an N-substituent group on the maleimide, the combination of its electron withdrawing influence on the maleimide ring (thus increasing its electrophilicity) and localized basicity (increasing the effective nucleophilicity of nearby water) can be used to tune the rate of hydrolysis of either the parent maleimide or its thio-substituted succinimide derivative. The present invention provides, inter alia, N-substituted maleimides with hydrolysis rates that fall within a useful range wherein their reaction with thiols occurs more quickly than their hydrolysis to the maleic acid derivative, but which yield thio-substituted succinimides with hydrolysis rates that are sufficiently rapid to achieve complete hydrolysis under gentle conditions that are very suitable for the manufacture of protein-based bioconjugates.

The present invention is based, in part, on the discovery that a basic functional group proximal to a maleimide will catalyze the hydrolysis of a thio-substituted succinimide which is formed upon conjugation of the maleimide and a protein thiol leading to a stable bioconjugate. By further combining a proximal basic group with an electron withdrawing group, the rate of thio-substituted succinimide ring hydrolysis can be tuned to a desirable level. Design parameters that affect the rate of hydrolysis include the pKa of the basic group, the strength of the electron withdrawing group when present, and the proximity of both groups to the maleimide carbonyl carbons. Design parameters that affect the percentage hydrolysis include the nature and proximity of the base to the maleimide carbonyl carbons.

Conceptually, without limiting the invention, a Linker unit comprising a self-stabilizing linker assembly is referred to herein as a Self-Stabilizing Linker or Self-Stabilizing Linker unit. The Self-Stabilizing Linker prior to conjugation with the Ligand unit comprises a maleimide group. The Self-Stabilizing Linker is self-stabilizing by virtue of the proximity of the maleimide group to a base within the Linker unit which catalyzes the hydrolysis of its own thio-substituted succinimide after conjugation to the Ligand unit. This is represented schematically below:

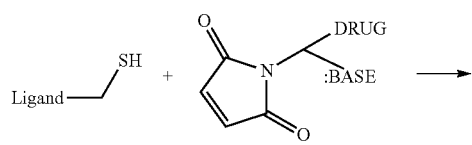

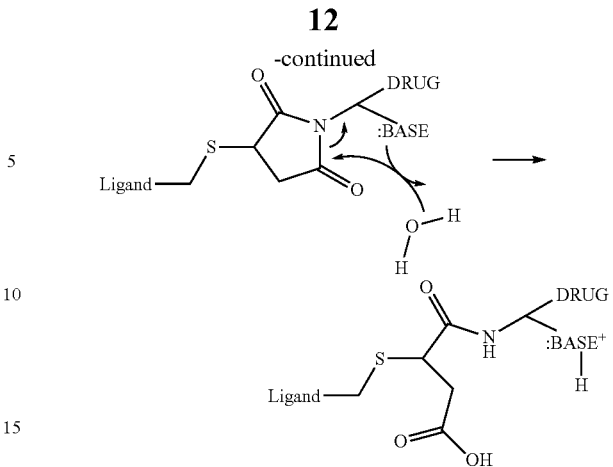

It will be understood that the term Self-Stabilizing Linker refers to the Linker unit both prior to and post stabilization.

In view of the above, the present invention provides in one group of embodiments, a Ligand-Functional Agent Conjugate comprising a Ligand unit and at least one Functional Agent selected from a Drug unit, a Detection Unit, or a Stabilizing Unit, wherein the Ligand unit and each of the Functional Agent(s) are joined by a self-stabilizing linker assembly comprising a succinimide ring or a hydrolyzed succinimide ring directly conjugated to the Ligand unit via a thioether linkage; and a base and an electron withdrawing group (conjugated to the Ligand unit via the succinimide) operably linked to stabilize the conjugate in plasma relative to a ligand drug conjugate lacking the self-stabilizing linker assembly (i.e. by increasing the rate of succinimide ring hydrolysis). In some aspects, the electron withdrawing group is positioned to increase the electrophilicity of the succinimide rendering it more reactive with water and the base is positioned to assist the hydrolysis of the succinimide ring (e.g., by an intramolecular base catalysis mechanism). In some aspects, in place of the succinimide ring is a dilactam formed when the base reacts with the succinimide ring. In another group of embodiments, Functional Agent-Linker units are provided wherein the Linker portion comprises a self-stabilizing linker assembly. In another group of embodiments, Ligand-Linker conjugates are provided, wherein the Linker portion comprises a self-stabilizing linker assembly. In some embodiments, the Linker portion further comprises an optional secondary linker assembly ($L^O$).

In some aspects, the Ligand-Functional Agent Conjugate is a Ligand-Drug Conjugate. Accordingly, the present invention provides in one group of embodiments, a Ligand-Drug Conjugate comprising a Ligand unit and at least one Drug unit, wherein the Ligand unit and each of the Drug unit(s) are joined by a self-stabilizing linker assembly comprising a succinimide ring or a hydrolyzed succinimide ring directly conjugated to the Ligand unit via a thioether linkage; and a base and an electron withdrawing group (conjugated to the Ligand unit via the succinimide ring) operably linked to stabilize the conjugate in plasma relative to a ligand drug conjugate lacking the self-stabilizing linker assembly (i.e. by increasing the rate of succinimide ring hydrolysis). In some aspects, the electron withdrawing group is positioned to increase the electrophilicity of the succinimide rendering it more reactive with water and the base is positioned to assist the hydrolysis of the succinimide ring (e.g., by an intramolecular base catalysis mechanism). In some aspects, in place of the succinimide ring is a dilactam formed when the base reacts with the succinimide ring. In another group of embodiments, Drug-Linker units are provided wherein the Linker portion comprises a self-stabilizing linker assembly. In another group of embodiments, Ligand-Linker conjugates are provided, wherein the Linker portion comprises a self-stabilizing linker assembly. In some embodiments, the Linker portion further comprises an optional secondary linker assembly ($L^O$). In some embodiments, the secondary linker assembly is a releasable linker assembly ($L^R$) which comprises a Cleavable unit and optionally one or more of a Stretcher and a Spacer unit. In some other embodiments, the secondary linker assembly is a non-releasable linker assembly ($L^N$) which comprises one or more of a Stretcher unit and a Spacer unit. In still other embodiments, the invention provides methods of treating cancer, immune disease, infectious diseases and other diseases and disorders using a Ligand-Drug Conjugate comprising a self-stabilizing linker assembly.

The Linker unit of the Ligand-Functional Agent Conjugate (or Ligand-Drug Conjugate) can further comprise, in addition to a self-stabilizing linker assembly, an optional secondary linker assembly ($L^O$) which joins each Functional Agent (or Drug unit) to the self-stabilizing linker assembly. The secondary linker assembly can be a releasable linker assembly or a non-releasable linker assembly.

The term Linker unit can be used herein to refer to the linker portion of the Ligand-Functional Agent Conjugate (or Ligand-Drug Conjugate) comprising the self-stabilizing linker assembly and optional secondary linker assembly.

The Self-Stabilizing Linker Assembly

The Self-Stabilizing Linkers are designed such that the rate of the post-conjugation hydrolysis of the succinimide ring will be controllable and fall within a desired range. The limits of this range are typically dictated by issues which arise in the manufacture of ligand-drug conjugates. On the one hand, hydrolysis which is too slow would require unacceptable delays in the manufacturing process or aggressive conditions of pH and temperature which may induce damage to the protein backbone. Conversely, a maleimide which is too reactive with water may be hydrolyzed to the corresponding maleic acid derivative before it can react with available protein thiols (see undesired pathway):

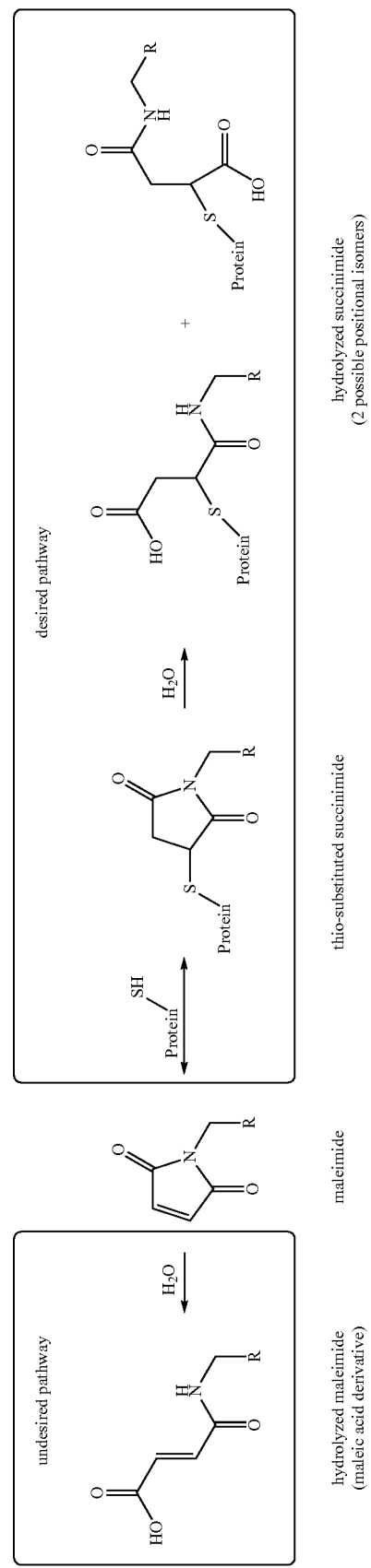

Such maleic acid derivatives are not reactive with thiols, and thus this reaction pathway does not result in a bioconjugate. Therefore, maleimides which undergo hydrolysis faster than thiol addition under applicable conditions are not useful reagents. In general, structural features which increase the hydrolysis rate of a thio-substituted succinimide will also increase the hydrolysis rate of the parent maleimide.

In designing the Self-Stabilizing Linkers of the present invention, it will be understood that the pKa of the basic group, the strength of the electron withdrawing group(s), and the proximity of both groups to the maleimide are inter-related variables and will affect the hydrolysis rate of both the maleimide and corresponding thio-substituted succinimide product. Accordingly, positioning of the electron withdrawing group and base will be dependent upon the pKa of the base and the strength of the electron withdrawing group(s). The skilled artisan will understand that for particularly strong electron withdrawing groups such as fluoro, trifluoromethyl, and nitro, the group can be further from the maleimide. In some embodiments, the hydrolysis reaction may compete with a macro-cyclization reaction such that the resultant conjugates comprise a heterogenous mixture of hydrolyzed thio-substituted succinimide conjugates and cyclized thio-substituted dilactam conjugates. In preferred embodiments, a dilactam will not be formed.

Selected Embodiments of the Invention

In some embodiments, the Ligand-Functional Agent Conjugate is represented by Formula I:

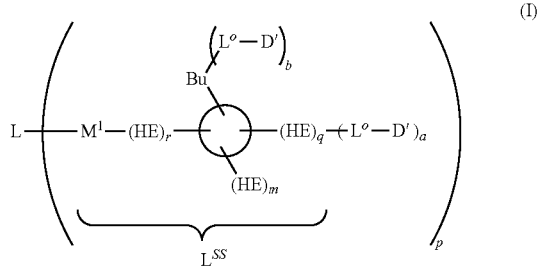

or a salt thereof (e.g., pharmaceutically acceptable salt thereof);
wherein
L is a Ligand unit;
D' is a Drug unit, a Detection unit, or a Stabilizing unit;
$L^O$ is the optional secondary linker assembly; and
$L^{SS}$ is the self-stabilizing linker assembly, wherein
  $M^1$ is a succinimide ring or a hydrolyzed succinimide or together with BU forms a dilactam;
  BU is a Basic unit;
  HE is a hydrolysis enhancer comprising an electron withdrawing group;
  the circle represents a scaffold that can be $C_{1-8}$ alkylene, $C_{1-8}$ heteroalkylene, $C_{6-10}$ arylene, or $C_{4-10}$ heteroarylene, and optionally comprises a reactive site suitable for attachment to the optional secondary linker assembly or D';
  the subscripts m, q and r are each 0 or 1, and the sum of m+q+r is 0, 1 or 2 provided that if m+q+r is 0, the scaffold is a $C_{6-10}$ arylene or $C_{4-10}$ heteroarylene;
  the subscript a and b are each 0 or 1, and the sum of a+b is 1; and
  the subscript p ranges from 1 to 20.

In some aspects, when r is 1, HE does not comprise a carbonyl group, (i.e.,

In some aspects, r is zero.

In some aspects m+q+r is 0. In such aspects, the $C_{6-10}$ arylene or $C_{4-10}$ heteroarylene act as the electron withdrawing group. Exemplary aryls and heteroaryls include phenyl and pyridinyl.

In some aspects m+q+r is 1 or 2.

In some aspects, the Conjugate is represented by Formula I or a salt thereof wherein a is 1 and r is zero.

In some aspects, the Conjugate is represented by Formula I or a salt thereof wherein $L^O$ is present and is a releasable linker assembly, the circle represents a scaffold that is $C_{1-8}$ alkylene or $C_{1-8}$ heteroalkylene (preferably $C_{1-4}$ alkylene or $C_{1-4}$ heteroalkylene), a is 1, r is zero, and the sum of m+q is 1. In some such aspects, the scaffold is $C_{1-3}$ alkylene or $C_{1-3}$ heteroalkylene. In some such aspects, the alkylene is straight chain or branched.

In some aspects, the Conjugate is represented by Formula I or a salt thereof wherein $L^O$ is present and is a releasable linker assembly, the circle represents a scaffold that is $C_{1-8}$ alkylene or $C_{1-8}$ heteroalkylene (preferably $C_{1-4}$ alkylene or $C_{1-4}$ heteroalkylene), a is 1, and m and r are zero. In some such aspects, the scaffold is $C_{1-3}$ alkylene or $C_{1-3}$ heteroalkylene. In some such aspects, the alkylene is straight chain or branched.

In some aspects, the Conjugate is represented by Formula I or a salt thereof wherein $L^O$ is present and is a releasable linker assembly, the circle represents a scaffold that is $C_1$, $C_2$, $C_3$ or $C_4$ straight or branched chain alkylene, a is 1, r is zero, and the sum of m+q is 1.

In some aspects, the Conjugate is represented by Formula I or a salt thereof wherein $L^O$ is present and is a releasable linker assembly, the circle represents a scaffold that is $C_1$, $C_2$, $C_3$ or $C_4$ straight or branched chain alkylene, a is 1, and m and r are zero.

In some aspects, there are no less than 2 and no more than 6 intervening atoms between the base of the Basic unit and the nitrogen atom of the succinimide (hydrolyzed or non-hydrolyzed) or dilactam and there are no more than 5 atoms, no more than 4 atoms, no more than 3 atoms, or no more than 2 intervening atoms between the electron withdrawing group and the nitrogen atom of the succinimide ring (hydrolyzed or non-hydrolyzed) or dilactam.

In each of these embodiments, the alkylene or heteroalkylene chain can be straight or branched. In some aspects, the alkylene or heteroalkylene chain will be a straight chain. In other aspects, it will be branched.

In each of these embodiments, p can range from 1 to 20, preferably 1 to 12, even more 1 to 10 or 1 to 8.

In each of these embodiments, $M^1$ is preferably a succinimide ring (i.e., non-hydrolyzed) or a hydrolyzed succinimide ring (also referred to herein as hydrolyzed succinimide).

In each of these embodiments, D' can be a Drug unit, D, and the Ligand-Functional Agent Conjugate can be a Ligand-Drug conjugate.

In some aspects wherein the scaffold itself is directly linked to the optional secondary linker assembly or D', (for example, in select embodiments when q is zero or when q is zero and r is zero), the scaffold will comprise a reactive site suitable for attachment to the optional secondary linker assembly or D'.

In some embodiments, the self-stabilizing linker assembly ($L^{SS}$) is represented by Formula II:

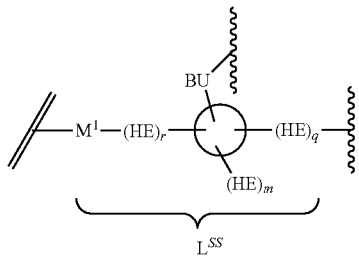

(II)

or a salt thereof (e.g., pharmaceutically acceptable salt) wherein the wavy lines indicates points for attachment of the optional secondary linker assembly to D' or D, and wherein// indicates the point of attachment to a Ligand Unit. In the self-stabilizing linker assembly above, $M^1$ represents a succinimide ring or a hydrolyzed succinimide ring or a dilactam formed when the base reacts with the succinimide ring, BU is a Basic unit, HE is a hydrolysis enhancer comprising an electron withdrawing group, and the circle represents a scaffold that can be $C_{1-8}$ alkylene, $C_{1-8}$ heteroalkylene, $C_{6-10}$ arylene, or $C_{4-10}$ heteroarylene, and optionally comprises a reactive site suitable for attachment to the optional secondary linker assembly, D', or D; and the subscripts m, q and r are each 0 or 1, and the sum of m+q+r is 0, 1 or 2 provided that if m+q+r is 0, the scaffold is a $C_{6-10}$ arylene or $C_{4-10}$ heteroarylene.

In some aspects, when r is 1, HE does not comprise a carbonyl group, (i.e., C(=O))

In some aspects, the self-stabilizing linker assembly is represented by Formula II wherein r is zero.

In some aspects m+q+r is 0. In such aspects, the $C_{6-10}$ arylene or $C_{4-10}$ heteroarylene act as the electron withdrawing group. Exemplary aryls and heteroaryls include phenyl and pyridinyl.

In some aspects m+q+r is 1 or 2.

In some aspects, the self-stabilizing linker assembly is represented by Formula II or a salt thereof wherein the circle represents a scaffold that is $C_{1-8}$ alkylene or $C_{1-8}$ heteroalkylene (preferably $C_{1-4}$ alkylene or heteroalkylene), r is zero, and the sum of m+q is 1. In some such aspects, the scaffold is $C_{1-3}$ alkylene or $C_{1-3}$ heteroalkylene. In some such aspects, the alkylene is a straight chain or branched alkylene.

In some aspects, the self-stabilizing linker assembly is represented by Formula II or a salt thereof wherein, the circle represents a scaffold that is $C_{1-8}$ alkylene or $C_{1-8}$ heteroalkylene (preferably $C_{1-4}$ alkylene or heteroalkylene) and m and r are zero. In some such aspects, the scaffold is $C_{1-3}$ alkylene or $C_{1-3}$ heteroalkylene. In some such aspects, the alkylene is a straight chain or branched alkylene.

In some aspects, the self-stabilizing linker assembly is represented by Formula II or a salt thereof wherein the circle represents a scaffold that is $C_1$, $C_2$, $C_3$, or $C_4$ straight or branched chain alkylene, r is zero, and the sum of m+q is 1.

In some aspects, the self-stabilizing linker assembly is represented by Formula II or a salt thereof wherein the circle represents a scaffold that is $C_1$, $C_2$, $C_3$, or $C_4$ straight or branched chain alkylene, and m and r are zero.

In some aspects, there are no less than 2 and no more than 6 intervening atoms between the base of the Basic unit and the nitrogen atom of the succinimide (hydrolyzed or non-hydrolyzed) or dilactam and there are no more than 5 atoms, no more than 4 atoms, no more than 3 atoms, or no more than 2 intervening atoms between the electron withdrawing group and the nitrogen atom of the succinimide ring (hydrolyzed or non-hydrolyzed) or dilactam.

In each of these embodiments, the alkylene or heteroalkylene chain will be a straight or branched chain. In some aspects, the alkylene or heteroalkylene chain will be a straight chain. In other aspects, it will be a branched chain.

In each of these embodiments, $M^1$ is preferably a succinimide ring or a hydrolyzed succinimide ring.

In each of these embodiments, D' is preferably D, a Drug unit.

Returning to the embodiments of the invention wherein the Ligand-Functional Agent Conjugate has the Formula (I):

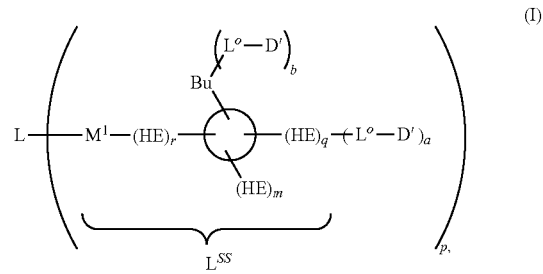

(I)

or a salt thereof, wherein each of the scaffold, L, $M^1$, HE, BU, $L^O$, D', and the subscripts p, a, b, m, q and r have the meanings provided above, selected embodiments include those wherein:

1) m is 1, and q and r are 0;
2) q is 1, and m and r are 0;
3) r is 1, and m and q are 0;
4) m is 1, q and r are 0, and a is 1;
5) q is 1, m and r are 0, and a is 1;
6) r is 1, m and q are 0, and a is 1;
7) m is 1, q and r are 0, and D' is a Drug unit, D;
8) q is 1, m and r are 0, and D' is a Drug unit, D;
9) r is 1, m and q are 0, and D' is a Drug unit, D;
10) m is 1, q and r are 0, a is 1, and D' is a Drug unit, D;
11) q is 1, m and r are 0, a is 1, and D' is a Drug unit, D; or
12) r is 1, m and q are 0, a is 1, and D' is a Drug unit, D.

In other selected embodiments, including each of the selected embodiments of 1), 2) 3), 4), 5), 6), 7), 8), 9), 10), 11), and 12) above, the Basic unit (BU) comprises a primary, a secondary amine, or a tertiary amine. In still other selected embodiments, including each of the selected embodiments of 1), 2) 3), 4), 5), 6), 7), 8), 9), 10), 11), and 12) above, the Basic unit is selected from the group consisting of))—(C($R^9$)($R^{10}$))$_x$NH$_2$, —(C($R^9$)($R^{10}$))$_x$NHR$^a$, and —(C($R^9$)($R^{10}$))$_x$NR$^a_2$, wherein x is an integer of from 0-4 (or from 1 to 4) and each R$^a$ is independently selected from the group consisting of $C_{1-6}$ alkyl and $C_{1-6}$ haloalkyl, or two R$^a$ groups are combined with the nitrogen to which they are attached to form an azetidinyl, pyrrolidinyl or piperidinyl group, provided that if x is zero there are no less than 2 intervening atoms between the base of the Basic unit and the nitrogen atom of the succinimide (hydrolyzed or non-hydrolyzed) or dilactam, and each $R^9$ and $R^{10}$ are independently selected from H or $C_{1-3}$ alkyl. In still other selected embodiments, including each of the selected embodiments of 1), 2) 3), 4), 5), 6), 7), 8), 9), 10), 11), and 12) above, the Basic unit is selected from the group consisting of —(CH$_2$)$_x$NH$_2$, —(CH$_2$)$_x$NHR$^a$, and —(CH$_2$)$_x$NR$^a_2$, wherein x is an integer of from 0 to 6 (preferably 0 to 4, or 1 to 4) provided that if x is zero there are no less than 2 intervening atoms between the base of the Basic unit and the nitrogen atom of the succinimide (hydrolyzed or non-hydrolyzed) or dilactam, and each $R^a$ is independently selected from the group consisting of $C_{1-6}$ alkyl and $C_{1-6}$ haloalkyl, or two $R^a$ groups are combined with the nitrogen to which they are attached to form an azetidinyl, pyrrolidinyl or piperidinyl group. In yet other selected embodiments, x is an integer of from 1 to 4. In even other selected embodiments, including each of the selected embodiments of 1), 2) 3), 4), 5), 6), 7), 8), 9), 10), 11), and 12) above, the Basic unit is —$NH_2$, —$CH_2NH_2$, —$CH_2CH_2NH_2$, —$CH_2CH_2CH_2NH_2$, or —$CH_2CH_2CH_2CH_2NH_2$ provided that if the Basic unit is —$NH_2$, there are no less than 2 intervening atoms between the base and the nitrogen atom of the succinimide (hydrolyzed or non-hydrolyzed) or dilactam.

In still other selected embodiments, including the selected embodiments of 2), 5), 8), and 11) above and including the embodiments of the preceding paragraph, HE comprises a carbonyl, sulfonyl or phosphoryl moiety.

In yet other selected embodiments, including each of the selected embodiments above (e.g., each of the selected embodiments of 1), 2) 3), 4), 5), 6), 7), 8), 9), 10), 11), and 12) above and including the embodiments of the preceding paragraphs), there are no less than 2 and no more than 6 intervening atoms between the base of the Basic unit and the nitrogen atom of the succinimide (hydrolyzed or non-hydrolyzed) or dilactam and there are no more than 5 atoms, no more than 4 atoms, no more than 3 atoms, or no more than 2 intervening atoms between the electron withdrawing group and the nitrogen atom of the succinimide ring (hydrolyzed or non-hydrolyzed) or dilactam.

In yet other selected embodiments, including each of the selected embodiments above (e.g., each of the selected embodiments of 1), 2) 3), 4), 5), 6), 7), 8), 9), 10), 11), and 12) above and including the embodiments of the preceding paragraphs, $M^1$ is a succinimide ring or hydrolyzed succinimide.

In yet other selected embodiments, including each of the selected embodiments above (e.g., each of the selected embodiments of 1), 2) 3), 4), 5), 6), 7), 8), 9), 10), 11), and 12) above and including the embodiments of the preceding paragraphs, the circle represents a scaffold that is $C_{1-8}$ alkylene or $C_{1-8}$ heteroalkylene (preferably $C_{1-4}$ alkylene or $C_{1-4}$ heteroalkylene). In some such aspects the alkylene is a straight or branched chain alkylene.

In yet other selected embodiments, the Ligand-Functional Agent Conjugates have the formula:

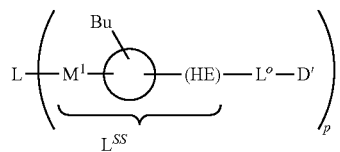

or a pharmaceutically acceptable salt thereof, wherein each of the scaffold, L, $M^1$, HE, BU, $L^O$, D', and the subscript p has the meaning provided above, selected embodiments include those wherein:
1) the Basic unit (BU) comprises a primary, a secondary amine, or a tertiary amine, and D' is preferably a Drug unit D.
2) the Basic unit is selected from the group consisting of —$(C(R^9)(R^{10}))_xNH_2$, —$(C(R^9)(R^{10}))_xNHR^a$, and —$(C(R^9)(R^{10}))_xNR^a_2$, wherein x is an integer of from 0-4 (or 1-4) and each $R^a$ is independently selected from the group consisting of $C_{1-6}$ alkyl and $C_{1-6}$ haloalkyl, or two $R^a$ groups are combined with the nitrogen to which they are attached to form an azetidinyl, pyrrolidinyl or piperidinyl group, provided that if x is zero, there are no less than 2 intervening atoms between the base of the Basic unit and the nitrogen atom of the succinimide (hydrolyzed or non-hydrolyzed) or dilactam, and $R^9$ and $R^{10}$ are independently selected from H or $C_{1-3}$ alkyl, and D' is preferably a Drug unit D.
3) the Basic unit is selected from the group consisting of —$(CH_2)_xNH_2$, —$(CH_2)_xNHR^a$, and —$(CH_2)_xNR^a_2$, wherein x is an integer of from 0 to 6 (preferably 0 to 4 or 1 to 4) provided that if x is zero, there are no less than 2 intervening atoms between the base of the Basic unit and the nitrogen atom of the succinimide (hydrolyzed or non-hydrolyzed) or dilactam, and each $R^a$ is independently selected from the group consisting of $C_{1-6}$ alkyl and $C_{1-6}$ haloalkyl, or two $R^a$ groups are combined with the nitrogen to which they are attached to form an azetidinyl, pyrrolidinyl or piperidinyl group, and D' is preferably a Drug unit D. In yet other selected embodiments, X is an integer of from 1 to 4.
4) the Basic unit is —$NH_2$, —$CH_2NH_2$, —$CH_2CH_2NH_2$, —$CH_2CH_2CH_2NH_2$, or —$CH_2CH_2CH_2CH_2NH_2$ provided that if the Basic unit is —$NH_2$, there are no less than 2 intervening atoms between the base and the nitrogen atom of the succinimide (hydrolyzed or non-hydrolyzed) or dilactam; and D' is preferably a Drug unit D.

In still other selected embodiments, including each of the selected embodiments above, HE comprises a carbonyl, sulfonyl or phosphoryl moiety, and D' is preferably a Drug unit D.

In yet other selected embodiments, including each of the selected embodiments above, there are no less than 2 and no more than 6 intervening atoms between the base of the Basic unit and the nitrogen atom of the succinimide (hydrolyzed or non-hydrolyzed) or dilactam and there are no more than 5 atoms, no more than 4 atoms, no more than 3 atoms, or no more than 2 intervening atoms between the electron withdrawing group and the nitrogen atom of the succinimide ring (hydrolyzed or non-hydrolyzed) or dilactam, and D' is preferably a Drug unit (D).

In yet other selected embodiments, including each of the selected embodiments above, $M^1$ is a succinimide ring or hydrolyzed succinimide, and D' is preferably a Drug unit (D).

In yet other selected embodiments, including each of the selected embodiments above, the circle represents a scaffold that is $C_{1-8}$ alkylene or $C_{1-8}$ heteroalkylene (preferably $C_{1-4}$ alkylene or $C_{1-4}$ heteroalkylene), and D' is preferably a Drug unit (D). In some such aspects, the alkylene is a straight chain or branched chain alkylene.

In still other selected embodiments, including each of the selected embodiments above, HE is a carbonyl, and D' is preferably a Drug unit (D).

In still other selected embodiments, including each of the selected embodiments above, HE is a carbonyl and the circle represents a scaffold that is a straight chain $C_{1-8}$ alkylene or $C_{1-8}$ heteroalkylene (preferably $C_{1-4}$ alkylene or $C_{1-4}$ heteroalkylene), and D' is preferably a Drug unit (D).

In still other selected embodiments, including each of the selected embodiments above, HE is a carbonyl and the circle represents a scaffold that is a branched chain $C_{1-8}$ alkylene or $C_{1-8}$ heteroalkylene (preferably $C_{1-4}$ alkylene or $C_{1-4}$ heteroalkylene), and D' is preferably a Drug unit (D).

In yet other selected embodiments, Ligand-Drug Conjugates have the formula:

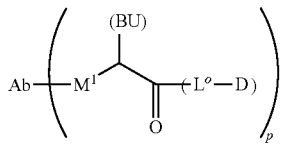

or a pharmaceutically acceptable salt thereof, wherein the Ligand portion is an antibody (Ab), the subscript p ranges from 1 to 20 (preferably 1 to 12), and $M^1$, BU, $L^O$ are as described in any of the embodiments provided herein, and D is a Drug unit. For example, in some aspects, $L^O$ is a releasable linker assembly, and BU is —$(CH_2)_xNH_2$, —$(CH_2)_xNHR^a$, and —$(CH_2)_xNR^a_2$, wherein x is an integer of from 1-4 and each $R^a$ is independently selected from the group consisting of $C_{1-6}$ alkyl and $C_{1-6}$ haloalkyl, or two $R^a$ groups are combined with the nitrogen to which they are attached to form an azetidinyl, pyrrolidinyl or piperidinyl group. In yet other aspects, $L^O$ is a releasable linker assembly, and BU is —$CH_2NH_2$, —$CH_2CH_2NH_2$, —$CH_2CH_2CH_2 NH_2$, or —$CH_2CH_2CH_2CH_2NH_2$. In some aspects, the Ab can be replaced by a non-antibody protein.

In yet other selected embodiments, the Ligand-Drug Conjugates have the formula:

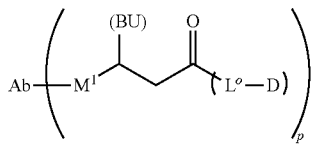

or a pharmaceutically acceptable salt thereof wherein the Ligand portion is an antibody (Ab) and the subscript p ranges from 1 to 20 (preferably 1 to 12) and $M^1$, BU, and $L^O$ are as described in any of the embodiments provided herein, and D is a Drug unit. For example, in some aspects, $L^O$ is a releasable linker assembly, and BU is —$(CH_2)_xNH_2$, —$(CH_2)_xNHR^a$, and —$(CH_2)_xNR^a_2$, wherein x is an integer of from 1-4 and each $R^a$ is independently selected from the group consisting of $C_{1-6}$ alkyl and $C_{1-6}$ haloalkyl, or two $R^a$ groups are combined with the nitrogen to which they are attached to form an azetidinyl, pyrrolidinyl or piperidinyl group. In yet other aspects, $L^O$ is a releasable linker assembly, and BU is —$CH_2NH_2$, —$CH_2CH_2NH_2$, —$CH_2CH_2CH_2 NH_2$, or —$CH_2CH_2CH_2CH_2 NH_2$. In some aspects, the Ab can be replaced by a non-antibody protein.

In yet other selected embodiments, the Ligand-Drug Conjugates have the formula:

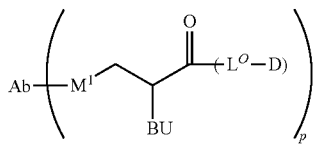

or a pharmaceutically acceptable salt thereof wherein the Ligand portion is an antibody (Ab), the subscript p ranges from 1 to 20 (preferably 1 to 12), and $M^1$, BU, and $L^O$ are as described in any of the embodiments provided herein and D is a Drug unit. For example, in some aspects, $L^O$ is a releasable linker assembly, and BU is —$(CH_2)_xNH_2$, —$(CH_2)_xNHR^a$, and —$(CH_2))_xNR^a_2$, wherein x is an integer of from 0-4 and each $R^a$ is independently selected from the group consisting of $C_{1-6}$ alkyl and $C_{1-6}$ haloalkyl, or two $R^a$ groups are combined with the nitrogen to which they are attached to form an azetidinyl, pyrrolidinyl or piperidinyl group. In yet other aspects, $L^O$ is a releasable linker assembly, and BU is —$NH_2$, —$CH_2NH_2$, —$CH_2CH_2NH_2$, —$CH_2CH_2CH_2 NH_2$, or —$CH_2CH_2CH_2CH_2 NH_2$. In some aspects, the Ab can be replaced by a non-antibody protein.

Having described a variety of Ligand-Functional Agent Conjugates and Ligand-Drug Conjugates provided by the present disclosure, one of skill in the art will appreciate that component assemblies are also useful. Accordingly, the present invention provides Fuctional Agent-Linker Conjugates (e.g., Drug-Linker Conjugates), Linkers, and Ligand-Linker assemblies.

Functional Agent-Linker Conjugates

In another embodiment, the present invention provides Functional Agent-Linker Conjugates (e.g., Drug-Linker Conjugates) having the formula:

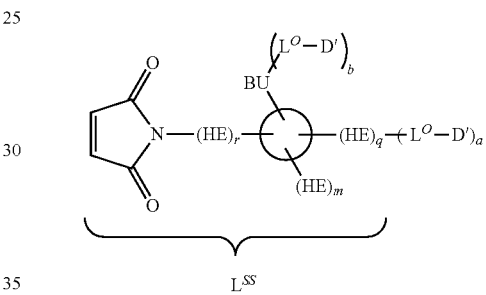

or a salt thereof (e.g., pharmaceutically acceptable salt) wherein,

D' is a Drug unit, a Detection unit, or a Stabilizing unit;
$L^O$ is an optional secondary linker assembly; and
$L^{SS}$ is the self-stabilizing linker assembly, wherein
  BU is a Basic unit;
  HE is a hydrolysis enhancer comprising an electron withdrawing group;
  the circle represents a scaffold that can be $C_{1-8}$ alkylene, $C_{1-8}$ heteroalkylene, $C_{6-10}$ arylene, or $C_{4-10}$ heteroarylene, and optionally comprises a reactive site suitable for attachment to the optional secondary linker assembly or D';
  the subscripts m, q and r are each 0 or 1, and the sum of m+q+r is 0, 1 or 2 provided that if m+q+r is 0, the scaffold is a $C_{6-10}$ arylene or $C_{4-10}$ heteroarylene, and the subscript a and b are each 0 or 1, and the sum of a+b is 1.

In certain selected embodiments, the Functional Agent-Linker Conjugate is represented by the formula:

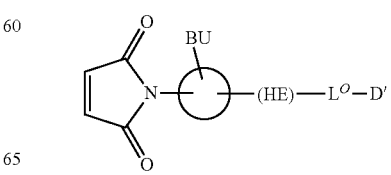

or a salt thereof, while in other selected embodiments, the Drug-Linker Conjugate is represented by the formulae:

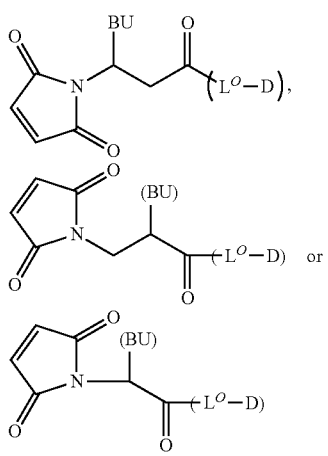

or a salt thereof, wherein the circle, HE, BU, $L^O$ and D' have the meanings provided above for Formula I and D is a Drug unit. Additionally, each of the specifically recited selected embodiments for the circle, HE, BU, $L^O$ and D' (for Formula I or any of the conjugates provided herein) are equally applicable to these Drug-Linker Conjugates. In preferred aspects D' is a Drug unit, D.

Linkers

Also provided herein are Linkers having the formula:

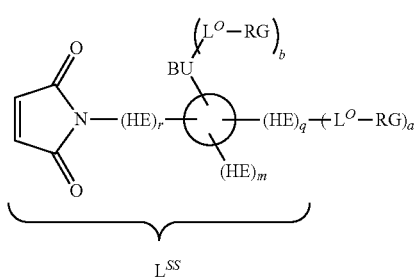

or a salt thereof (e.g., pharmaceutically acceptable salt), wherein

RG is a reactive group (comprising a reactive site) at the terminus of $L^O$, suitable for attaching a Drug unit;

$L^O$ is an optional secondary linker assembly that is present; and $L^{SS}$ is the self-stabilizing linker assembly, wherein BU is a Basic unit;

HE is a hydrolysis enhancer comprising an electron withdrawing group;

the circle represents a scaffold that can be $C_{1-8}$ alkylene, $C_{1-8}$ heteroalkylene, $C_{6-10}$ arylene, or $C_{4-10}$ heteroarylene, and optionally comprises a reactive site suitable for attachment to the optional secondary linker assembly or Drug unit;

the subscripts m, q and r are each 0 or 1, and the sum of m+q+r is 0, 1 or 2 provided that if m+q+r is 0, the scaffold is a $C_{6-10}$ arylene or $C_{4-10}$ heteroarylene; and the subscript a and b are each 0 or 1, and the sum of a+b is 1.

In some aspects wherein the Linker is attached to a Detection unit or a Stabilizing unit, RG is a reactive group that contains a reactive site that is capable of forming a bond with a Detection unit or a Stabilizing unit instead of a Drug unit.

In certain selected embodiments, the Linker is represented by the formula:

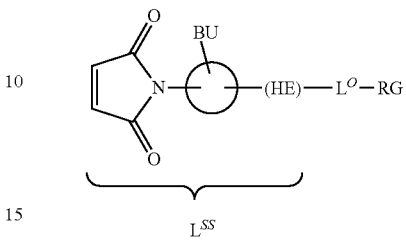

or a salt thereof, while in other selected embodiments, the Linker is represented by the formulae:

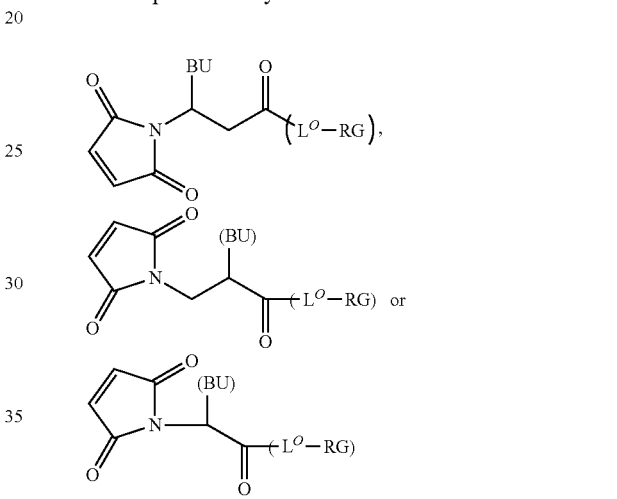

or a salt thereof (e.g., pharmaceutically acceptable salt) wherein the circle, HE, BU, $L^O$ and RG have the meanings provided above. Additionally, each of the specifically recited selected embodiments for BU, $L^O$ and RG (for any of the conjugates provided herein) are equally applicable to these Linkers.

Ligand-Linker Conjugates

Also provided herein are Ligand-Linker Conjugates, having the formula:

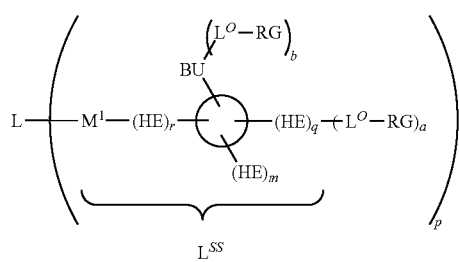

or a salt thereof (e.g., pharmaceutically acceptable salt) wherein

L is a Ligand unit;

the subscript p ranges from 1 to 20;

RG is a reactive group (comprising a reactive site) at the terminus of $L^O$ which is suitable for attaching a Drug unit;

$L^O$ is an optional secondary linker assembly that is present; and $L^{SS}$ is a self-stabilizing linker assembly, wherein $M^1$ is a succinimide ring or hydrolyzed succinimide;

BU is a Basic unit;

HE is a hydrolysis enhancer comprising an electron withdrawing group;

the circle represents a scaffold that can be $C_{1-8}$ alkylene, $C_{1-8}$ heteroalkylene, $C_{6-10}$ arylene, or $C_{4-10}$ heteroarylene, and optionally comprises a reactive site suitable for attachment to the optional secondary linker assembly or Drug unit;

the subscripts m, q and r are each 0 or 1, and the sum of m+q+r is 0, 1 or 2 provided that if m+q+r is 0, the scaffold is a $C_{6-10}$ arylene or $C_{4-10}$ heteroarylene; and the subscript a and b are each 0 or 1, and the sum of a+b is 1.

In some aspects wherein the Ligand-Linker Conjugate is attached to a Detection unit or a Stabilizing unit instead of a Drug unit, RG is a reactive group that contains a reactive site that is capable of forming a bond with a Detection unit or a Stabilizing unit instead of a Drug unit.

In certain selected embodiments, the Ligand-Linker Conjugate is represented by the formula:

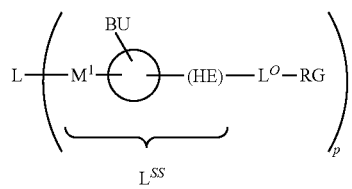

or a salt thereof while in other selected embodiments, the Ligand-Linker Conjugate is represented by the formula:

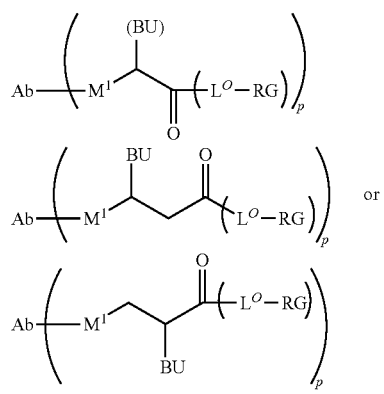

or a salt thereof (e.g., pharmaceutically acceptable salt), wherein L is an antibody (Ab), and the circle, HE, $M^1$, BU, $L^O$ and RG have the meanings provided above. Additionally, each of the specifically recited selected embodiments for Ab, $M^1$, BU, $L^O$ and RG (for any of the conjugates provided herein) are equally applicable to these Ligand-Linker conjugates.

In some embodiments of the invention, the self-stabilizing linker assembly instead of being represented by the structure for $L^{SS}$ is represented by $L^{TT}$ and has Formula (III):

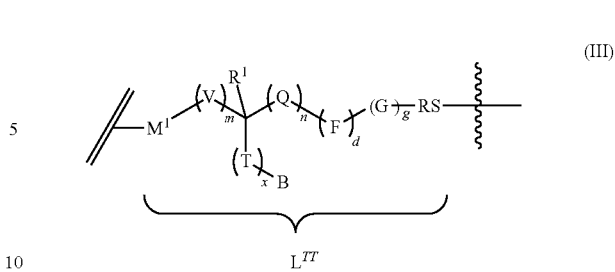

or a pharmaceutically acceptable salt thereof, wherein the wavy line indicates points of attachment of the optional secondary linker assembly or Drug unit and wherein // indicates the point of attachment to a Ligand unit;

wherein $M^1$ is a non-hydrolyzed or hydrolyzed succinimide or $M^1$ forms a dilactam with B (e.g., a dilactam is formed when B reacts with the succinimide ring), wherein the succinimide or dilactam is conjugated to the Ligand unit via a thioether linkage;

V, Q, T, and G are independently selected from $—(C(R^9)(R^{10}))—$;

$R^1$ is H or $C_{1-3}$ alkyl;

$R^9$ and $R^{10}$ are, in each occurrence, independently selected from H or $C_{1-3}$ alkyl;

F is $C(E^1)(E^2)$ wherein $E^1$ and $E^2$ are independently selected from hydrogen, an electron withdrawing group, or $E^1$ and $E^2$ together are (=O);

RS is a reactive site for conjugation to a component of the optional secondary linker assembly or Drug unit;

g is 0 to 5;

m is 0 to 5;

n is 0 to 5;

d is 0 or 1;

x is 0 to 4, provided that when m is 0, x is 1 to 4;

and B is a base.

In some aspects, there are from 1 to 20 drug-linkers attached to each Ligand unit.

In selected embodiments, Ligand-Drug Conjugates have the formula:

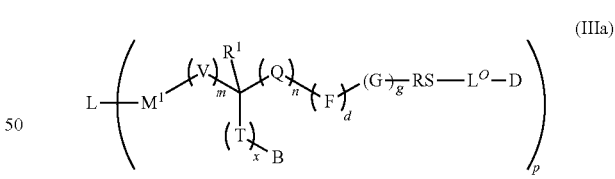

or a pharmaceutically acceptable salt thereof.

In selected embodiments, Drug-linkers have the formula:

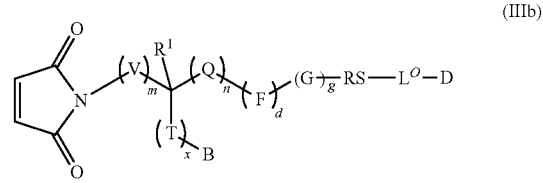

or a pharmaceutically acceptable salt thereof.

In selected embodiments, Linkers have the formula $$\text{(IIIc)}$$

or a pharmaceutically acceptable salt thereof.

In selected embodiments, Ligand-Linker Conjugates have the formula:

$$\text{(IIId)}$$

or a pharmaceutically acceptable salt thereof.

In formulas IIIa, IIIb, IIIc, and IIId or pharmaceutically acceptable salts thereof:

L, if present, is a Ligand unit;

$L^O$ is an optional secondary linker assembly;

RG, if present, is a reactive group (comprising a reactive site) at the terminus of $L^O$ which is suitable for attaching a Drug unit;

$M^1$, if present, is a non-hydrolyzed or hydrolyzed succinimide or $M^1$ forms a dilactam with B (e.g., a dilactam is formed when the base reacts with the succinimide ring), wherein the succinimide or dilactam is conjugated to the Ligand unit via a thioether linkage;

V, Q, T, and G are independently selected from $-(C(R^9)(R^{10}))-$;

$R^1$ is H or $C_{1-3}$ alkyl;

$R^9$ and $R^{10}$ are, in each occurrence, independently selected from H or $C_{1-3}$ alkyl;

F is $C(E^1)(E^2)$ wherein $E^1$ and $E^2$ are independently selected from hydrogen, an electron withdrawing group, or $E^1$ and $E^2$ together are (=O);

RS is a reactive site for conjugation to a component of the optional secondary linker assembly or Drug unit;

g is 0 to 5;
m is 0 to 5;
n is 0 to 5;
d is 0 or 1;
x is 0 to 4, provided that when m is 0, x is 1 to 4;
p, if present, ranges from 1 to 20, preferably 1 to 12;
and B is a base.

It will be understood that for Formula III (including IIIa, IIIb, IIIc, and IIId) and pharmaceutically acceptable salts thereof, the electron withdrawing group will either be represented by F (e.g., $E^1$, $E^2$ or $E^1$ and $E^2$) or by the reactive site RS. For example, when d is zero, or when $E^1$ and $E^2$ are hydrogen, the reactive site will act as an electron withdrawing group. In some aspects, when d is zero, RS is —C(=O)—. In some aspects, n, d, and g are zero or m, n, d, and g are zero and RS is —C(=O)—.

Exemplary embodiments wherein the Ligand-Drug Conjugates, Drug-Linkers, Linkers, or Ligand-Linker conjugates are represented by Formula III (or formulae IIIa, IIIb, IIIc, or IIId, as the case may be) or pharmaceutically acceptable salts thereof, include those wherein m is zero; m is zero and n is zero, one, two, or three; x is 1; x is zero and n is zero, one, two, or three; and m is zero, n is zero, and x is 1. Exemplary embodiments include those described herein wherein $R^9$ and $R^{10}$ are hydrogen. Exemplary embodiments include those wherein $E^1$ and $E^2$ are independently selected from H, —CN, —NO$_2$, —CX$_3$ wherein X is halogen or $E^1$ and $E^2$ together are (=O). The remainder of the substituents are as defined.

Exemplary embodiments wherein the Ligand-Drug Conjugates, Drug-Linkers, Linkers, or Ligand-Linker conjugates are represented by Formula III (or formulae IIIa, IIIb, IIIc, or IIId, as the case may be) or pharmaceutically acceptable salts thereof include those wherein:

(i) $E^1$ and $E^2$ are independently selected from hydrogen, —CN, —NO$_2$, —CX$_3$, and —X wherein X is halogen or $E^1$ and $E^2$ together are (=O);
(ii) m is zero and n is zero, one two or three;
(iii) x is 1;
(iv) x is 4;
(v) x is zero, and n is zero, one, two or three;
(vi) m is zero, n is zero, and x is 1;
(vii) d is 1 and g is 1 to 5;
(viii) d is 1 and g is 2 to 5;
(ix) n, d, and g are zero;
(x) m, n, d, and g are zero;
(xi) RS is —C(=O)—;
(xii) $E^1$ and $E^2$ are together (=O);
(xiii) B is or —N(R$^3$)(R$^4$), wherein R$^3$, R$^4$, R$^5$, R$^6$, R$^7$ and R$^8$ are independently selected from H or C$_{1-6}$ alkyl and e is 0 to 4;

(xiv) B is —N(R$^3$)(R$^4$), wherein R$^3$ and R$^4$ are independently selected from H or C$_{1-6}$ alkyl;

(xv) B is as in (xiii) or (xiv) and $R^3$, $R^4$, $R^5$, $R^6$, $R^7$ and $R^8$ are independently selected from H or $C_{1-3}$ alkyl;
(xvi) B is as in (xiii) or (xiv) and $R^3$, $R^4$, $R^5$, $R^6$, $R^7$ and $R^8$ are independently selected from H or methyl;
(xvii) B is as in (xiii) or (xiv) or (xvi) and $R^3$ and $R^4$ are hydrogen;
(xviii) B is as in (xiii) or (xiv) or (xvi) and at least one of $R^3$ and $R^4$ are hydrogen;
(xix) B is as in (xiii) or (xiv) or (xvi) and at least one of $R^3$ and $R^4$ is not hydrogen;
(XX) $R^1$, $R_9$, and $R^{10}$ are independently selected from H or methyl;
(xxi) $R^1$, $R^9$, and $R^{10}$ are hydrogen;
(xxii) $R^1$, $R^9$, and $R^{10}$ are independently selected from H or methyl;
(xxiii) The cleavable unit is present;
(xxiv) The cleavable unit is present and has the formula $-(AA-AA)_{1-6-}$; wherein AA is at each occurrence independently selected from an amino acid;
(xxv) The cleavable unit is present and conjugated directly to the Drug unit;
(xxvi) The cleavable unit is present and conjugated directly to the Drug unit via a cleavable peptide, disulfide, or hydrazone bond;
(xxvii) The cleavable unit is present and the Spacer and Stretcher unit are absent;
(xxviii) The Drug is an auristatin;
(xxix) $M^1$ is a hydrolyzed or non-hydrolyzed succinimide;
(xxx) p is about 4;
(xxxi) p is about 8;
(xxxii) the t1/2 of hydrolysis of the thio-substituted succinimide of the Self-Stabilizing unit is from about 10 minutes to about 2.5 hours at pH 7.4 and 22° C.;
(xxxiii) the t1/2 of hydrolysis of the thio-substituted succinimide of the Self-Stabilizing unit is from about 10 minutes to about 1 hour at pH 7.4 and 22° C.;
(xxxiv) the t1/2 of hydrolysis of the thio-substituted succinimide of the Self-Stabilizing unit is from about 10 minutes to about 30 minutes at pH 7.4 and 22° C.;
(xxxv) the Ligand unit is an antibody;
(xxxvi) the Ligand unit is an antibody and is attached to the Linker unit though a cysteine residue of an interchain disulfide;
(xxxvii) the Ligand unit is a monoclonal antibody;
and any combinations or subcombinations of (i) through (xxxvii) provided that the combinations or subcombinations do not conflict with each other (e.g., xxx and xxxi conflict because p cannot be both about 4 and about 8). For example, in selected embodiments, m is zero, and n is zero, one, two, or three. In other selected embodiments, m is zero, n is zero, and x is one. In any of these selected embodiments, d can be one and g can be from 1 to 5 or d can be one and g can be from 2 to 5. In any of these embodiments, one or more of (i), (iii) or (xi)-(xxxvi) can apply.

In each of the selected embodiments wherein the Ligand-Drug Conjugates, Drug-Linkers, Linkers, or Ligand-Linker conjugates are represented by Formula III (or formulae IIIa, IIIb, IIIc, or IIId, as the case may be) or pharmaceutically acceptable salts thereof, the optional secondary linker assembly can be represented by the following formula:

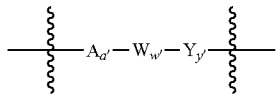

wherein -A- is an optional Stretcher unit, the subscript a' is 0 or 1; —W— is an optional Cleavable unit, the subscript w' is 0 or 1; and —Y— is an optional Spacer unit, and the subscript y' is 0 or 1.

Also included are selected embodiments wherein the Linker has the formula:

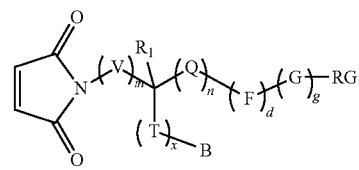

or a pharmaceutically acceptable salt thereof wherein V, T, B, $R^1$, Q, F, G, m, x, n, d, and g are as defined for formula III and RG is a reactive group comprising a reactive site, RS, for conjugation to the Drug unit D when the secondary linker assembly is absent or to a component of the secondary linker assembly wherein the secondary linker assembly secondary linker has the following formula:

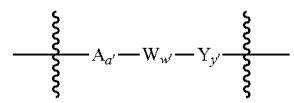

wherein -A- is an optional Stretcher unit, the subscript at is 0 or 1; —W— is an optional Cleavable unit, the subscript w' is 0 or 1; and —Y— is an optional Spacer unit, and the subscript y' is 0 or 1.

Further Embodiments of the Invention

Exemplary self-stabilizing linker assemblies prior to conjugation with a Ligand and following conjugation and hydrolysis of the thio-substituted succcinimide which is formed upon conjugation are as follows:

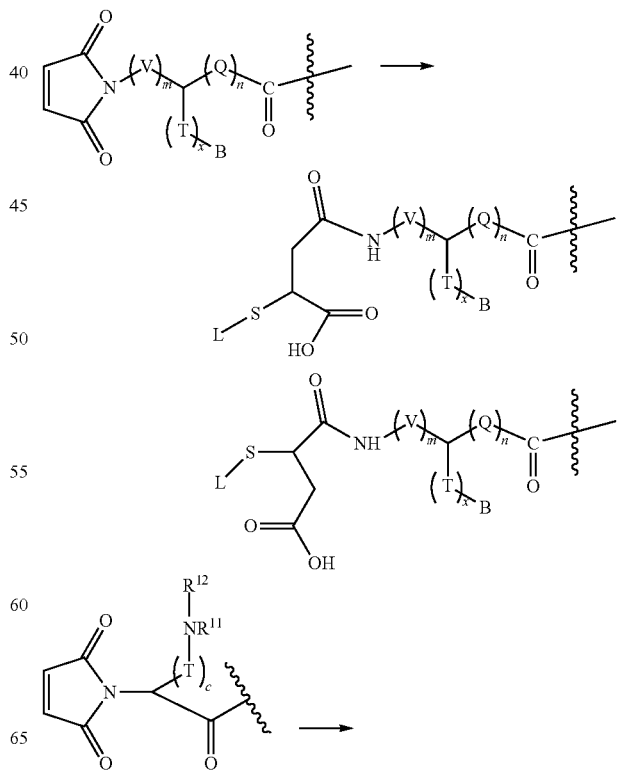

33
-continued

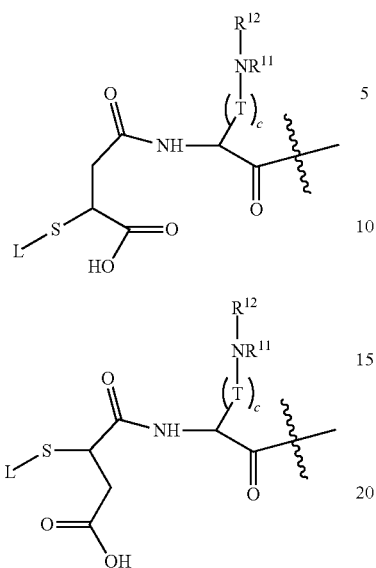

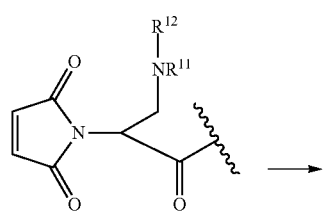

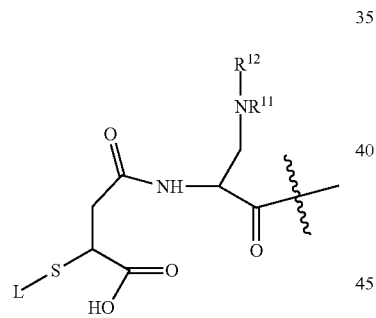

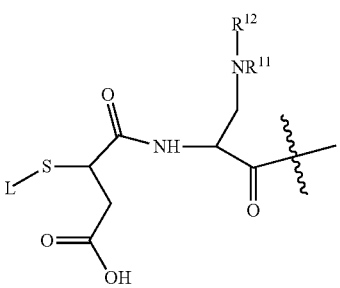

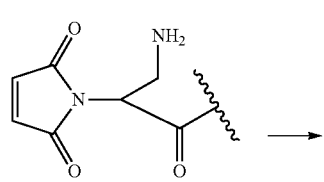

34
-continued

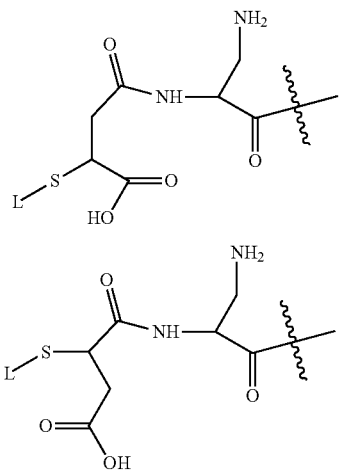

or pharmaceutically acceptable salts thereof, wherein V, Q, T, m, n, x, and B, are as defined above for Formula III or any other selected embodiment, c is from 1 to 4, and $R^{11}$ and $R^{12}$ are, at each occurrence, independently selected from H or $C_1$-$C_6$ alkyl. In an exemplary embodiment c is 1 or 4. The "S" of the hydrolyzed thio-succinimide represents a sulfur atom of the Ligand (e.g., antibody). The wavy line indicates linkage to the secondary linker assembly or Drug unit. In an exemplary embodiment, the wavy line indicates linkage to the following secondary linker assembly $$-\!\!\xi\!\!-\!A_{a'}\!-\!W_{w'}\!-\!Y_{y'}\!-\!\xi\!\!-$$

wherein -A- is an optional Stretcher unit, the subscript a' is 0 or 1; —W— is an optional Cleavable unit, the subscript w' is 0 or 1; and —Y— is an optional Spacer unit, and the subscript y' is 0 or 1.

In some aspects of the present invention, a self-stabilizing linker assembly may undergo macro-cyclization to form a dilactam as follows wherein R represents the remainder of the conjugate:

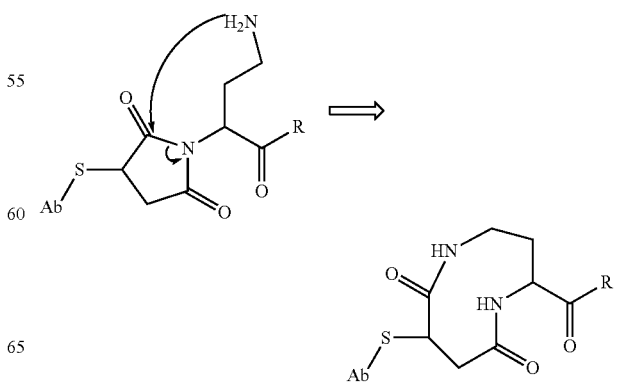

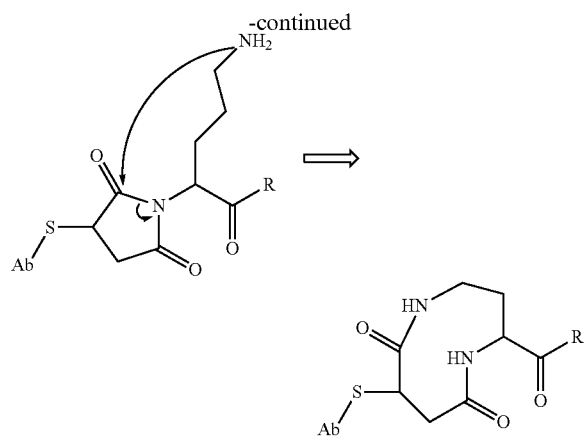

Secondary Linker Assembly

The optional secondary linker can comprise a variety of linking groups. In each of the embodiments provided herein, including the specifically recited embodiments, $L^O$ can be present and have the formula:

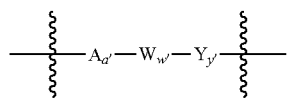

wherein
-A- is an optional Stretcher unit, the subscript a' is 0 or 1;
—W— is an optional Cleavable unit, the subscript w' is 0 or 1; and
—Y— is an optional Spacer unit, and the subscript y' is 0 or 1;

The optional secondary linker assembly can be a releaseable linker assembly, $L^R$. In those embodiments, w is 1. In some other aspects, the optional secondary linker assembly is a non-releasable linker assembly. In those embodiments w is 0 and release of drug is via a total protein degradation pathway (i.e., non-cleavable pathway).

The Ligand Unit

In some embodiments of the invention, a Ligand Unit is present. The Ligand unit (L-) is a targeting agent that specifically binds to a target moiety. The Ligand can specifically bind to a cell component (a Cell Binding Agent) or to other target molecules of interest. In some aspects, the Ligand unit acts to deliver the Drug unit to the particular target cell population with which the Ligand unit interacts. Ligands include, but are not limited to, proteins, polypeptides and peptides. Suitable Ligand units include, for example, antibodies, e.g., full-length antibodies and antigen binding fragments thereof, interferons, lymphokines, hormones, growth factors and colony-stimulating factors, vitamins, nutrient-transport molecules (such as, but not limited to, transferrin), or any other cell binding molecule or substance. In some aspects, the ligand is a non-antibody protein targeting agent. In some aspects, a Ligand-Functional Agent is provided wherein D' is a Detection Unit or Stabilizing unit and the Ligand unit is a protein (e.g., a non-antibody protein).

In some aspects, a Ligand unit forms a bond with the maleimide of the Self-Stabilizing Basic unit via a sulfhydryl group of the Ligand to form a thio-substituted succinimide. The sulfhydryl group can be present on the Ligand in the Ligand's natural state, for example a naturally-occurring antibody, or can be introduced into the Ligand via chemical modification.

It has been observed for bioconjugates that the site of drug conjugation can affect a number of parameters including ease of conjugation, drug-linker stability, effects on biophysical properties of the resulting bioconjugates, and in-vitro cytotoxicity. With respect to drug-linker stability, the site of conjugation of a drug-linker to a ligand can affect the ability of the conjugated drug-linker to undergo an elimination reaction and for the drug linker to be transferred from the ligand of a bioconjugate to an alternative reactive thiol present in the milieu of the bioconjugate, such as, for example, a reactive thiol in albumin, free cysteine, or glutathione when in plasma. Use of the Self-Stabilizing Linkers of the present invention is particularly beneficial when conjugated to thiol residues at sites that are susceptible to the elimination reaction and subsequent transfer of drug-linker if non-self-stabilizing alkyl maleimides are used (e.g., maleimido-caproyl drug linker). Such sites include, for example, the interchain disulfides as well as select cysteine engineered sites. Use of the Self-Stabilizing Linkers of the present invention provides a stable linkage and ability to attach multiple drugs to each Ligand unit.

In one aspect, the Ligand unit has one or more lysine residues that can be chemically modified to introduce one or more sulfhydryl groups. The reagents that can be used to modify lysines include, but are not limited to, N-succinimidyl S-acetylthioacetate (SATA) and 2-Iminothiolane hydrochloride (Traut's Reagent).

In another embodiment, the Ligand unit can have one or more carbohydrate groups that can be chemically modified to have one or more sulfhydryl groups.

In another embodiment, the sulfhydryl groups is be generated by reduction of the interchain disulfides. Accordingly, in some embodiments, the Linker unit is conjugated to a cysteine residue of the reduced interchain disulfides.

In another embodiment, the sulfhydryl group is chemically introduced into the antibody, for example by introduction of a cysteine residue. Accordingly, in some embodiments, the Linker unit is conjugated to an introduced cysteine residue.

Useful non-immunoreactive protein, polypeptide, or peptide Ligands include, but are not limited to, transferrin, epidermal growth factors ("EGF"), bombesin, gastrin, gastrin-releasing peptide, platelet-derived growth factor, IL-2, IL-6, transforming growth factors ("TGF"), such as TGF-α and TGF-β, vaccinia growth factor ("VGF"), insulin and insulin-like growth factors I and II, somatostatin, lectins and apoprotein from low density lipoprotein.

Particularly preferred ligands are antibodies. Useful polyclonal antibodies are heterogeneous populations of antibody molecules derived from the sera of immunized animals. Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture.

Useful monoclonal antibodies include, but are not limited to, human monoclonal antibodies, humanized monoclonal antibodies, or chimeric human-mouse (or other species) monoclonal antibodies. The antibodies include full-length antibodies and antigen binding fragments thereof. Human monoclonal antibodies may be made by any of numerous techniques known in the art (e.g., Teng et al., 1983, *Proc. Natl. Acad. Sci. USA.* 80:7308-7312; Kozbor et al., 1983, *Immunology Today* 4:72-79; and Olsson et al., 1982, *Meth. Enzymol.* 92:3-16).

The antibody can be a functionally active fragment, derivative or analog of an antibody that immunospecifically binds to target cells (e.g., cancer cell antigens, viral antigens, or microbial antigens) or other antibodies bound to tumor cells or matrix. In this regard, "functionally active" means that the fragment, derivative or analog is able to elicit anti-anti-idiotype antibodies that recognize the same antigen that the antibody from which the fragment, derivative or analog is derived. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay) (See, e.g., Kabat et al., 1991, *Sequences of Proteins of Immunological Interest*, Fifth Edition, National Institute of Health, Bethesda, Md.; Kabat E et al., 1980, *J. Immunology* 125(3):961-969).

Other useful antibodies include fragments of antibodies such as, but not limited to, $F(ab')_2$ fragments, Fab fragments, Fvs, single chain antibodies, diabodies, tribodies, tetrabodies, scFv, scFv-FV, or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as for example, those having a variable region derived from a murine monoclonal and human immunoglobulin constant regions. (See, e.g., U.S. Pat. Nos. 4,816,567; and 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., 1988, *Science* 240:1041-1043; Liu et al., 1987, *Proc. Natl. Acad. Sci. USA* 84:3439-3443; Liu et al., 1987, *J. Immunol.* 139:3521-3526; Sun et al., 1987, *Proc. Natl. Acad. Sci. USA* 84:214-218; Nishimura et al., 1987, *Cancer. Res.* 47:999-1005; Wood et al., 1985, *Nature* 314:446-449; and Shaw et al., 1988, *J. Natl. Cancer Inst.* 80:1553-1559; Morrison, 1985, *Science* 229:1202-1207; Oi et al., 1986, *BioTechniques* 4:214; U.S. Pat. No. 5,225,539; Jones et al., 1986, *Nature* 321:552-525; Verhoeyan et al., 1988, *Science* 239:1534; and Beidler et al., 1988, *J. Immunol.* 141:4053-4060; each of which is incorporated herein by reference in its entirety.

Completely human antibodies are particularly desirable and can be produced using transgenic mice that are incapable of expressing endogenous immunoglobulin heavy and light chains genes, but which can express human heavy and light chain genes.

Antibodies include analogs and derivatives that are either modified, i.e., by the covalent attachment of any type of molecule as long as such covalent attachment permits the antibody to retain its antigen binding immunospecificity. For example, but not by way of limitation, derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques including, but not limited to, specific chemical cleavage, acetylation, formylation, metabolic synthesis in the presence of tunicamycin, etc. Additionally, the analog or derivative can contain one or more unnatural amino acids.

Antibodies can have modifications (e.g., substitutions, deletions or additions) in amino acid residues that interact with Fc receptors. In particular, antibodies can have modifications in amino acid residues identified as involved in the interaction between the anti-Fc domain and the FcRn receptor (see, e.g., International Publication No. WO 97/34631, which is incorporated herein by reference in its entirety).

Antibodies immunospecific for a cancer cell antigen can be obtained commercially or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, the literature publications, or by routine cloning and sequencing.

In a specific embodiment, known antibodies for the treatment of cancer can be used. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing.

In another specific embodiment, antibodies for the treatment of an autoimmune disease are used in accordance with the compositions and methods of the invention. Antibodies immunospecific for an antigen of a cell that is responsible for producing autoimmune antibodies can be obtained from any organization (e.g., a university scientist or a company) or produced by any method known to one of skill in the art such as, e.g., chemical synthesis or recombinant expression techniques. In another embodiment, useful antibodies are immunospecific for the treatment of autoimmune diseases include, but are not limited to, anti-nuclear antibody; anti-ds DNA; Anti-ss DNA, anti-cardiolipin antibody IgM, IgG; anti-phospholipid antibody IgM, IgG; anti-SM antibody; anti-mitochondrial antibody; thyroid antibody; microsomal antibody; thyroglobulin antibody; anti-SCL-70 antibody; anti-Jo antibody; anti-$U_1$RNP antibody; anti-La/SSB antibody; anti-SSA; anti-SSB antibody; anti-perital cells antibody; anti-histones antibody; anti-RNP antibody; C-ANCA antibody; P-ANCA antibody; anti-centromere antibody; Anti-Fibrillarin antibody and anti-GBM antibody.

In certain embodiments, useful antibodies can bind to a receptor or a receptor complex expressed on an activated lymphocyte. The receptor or receptor complex can comprise an immunoglobulin gene superfamily member, a TNF receptor superfamily member, an integrin, a cytokine receptor, a chemokine receptor, a major histocompatibility protein, a lectin, or a complement control protein. Non-limiting examples of suitable immunoglobulin superfamily members are CD2, CD3, CD4, CD8, CD19, CD20, CD22, CD28, CD30, CD70, CD79, CD90, CD152/CTLA-4, PD-1, and ICOS. Non-limiting examples of suitable TNF receptor superfamily members are CD27, CD40, CD95/Fas, CD134/OX40, CD137/4-1BB, TNF-R1, TNFR-2, RANK, TACI, BCMA, osteoprotegerin, Apo2/TRAIL-R1, TRAIL-R2, TRAIL-R3, TRAIL-R4, and APO-3. Non-limiting examples of suitable integrins are CD11a, CD11b, CD11c, CD18, CD29, CD41, CD49a, CD49b, CD49c, CD49d, CD49e, CD49f, CD103, and CD104. Non-limiting examples of suitable lectins are C-type, S-type, and I-type lectin.

The Drug Unit, D

The drug unit (D) can be any cytotoxic, cytostatic or immunosuppressive drug also referred to herein as a cytotoxic, cytostatic or immunosuppressive agent. The Drug unit has an atom that can form a bond with the Linker Unit. In some embodiments, the Drug unit D has a nitrogen atom that can form a bond with the Linker unit. In other embodiments, the Drug unit D has a carboxylic acid that can form a bond with the Linker unit. In other embodiments, the Drug unit D has a sulfhydryl group that can form a bond with the Linker unit. In other embodiments, the Drug unit D has a hydroxyl group or ketone that can form a bond with the Linker unit.

Useful classes of cytotoxic or immunosuppressive agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like. Particularly examples of useful classes of cytotoxic agents include, for example, DNA minor groove binders, DNA alkylating agents, and tubulin inhibitors. Exemplary cytotoxic agents include, for example, auristatins, camptothecins, duocarmycins, etoposides, maytansines and maytansinoids (e.g., DM1 and DM4), taxanes, benzodiazepines (e.g., pyrrolo[1,4]benzodiazepines (PBDs), indolinobenzodiazepines, and oxazolidinobenzodiazepines) and vinca alkaloids. Select benzodiazepine containing drugs are described in WO 2010/091150, WO 2012/112708, WO 2007/085930, and WO 2011/023883.

Individual cytotoxic or immunosuppressive agents include, for example, an androgen, anthramycin (AMC), asparaginase, 5-azacytidine, azathioprine, bleomycin, busulfan, buthionine sulfoximine, calicheamicin, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, etoposide, an estrogen, 5-fluordeoxyuridine, 5-fluorouracil, gemcitabine, gramicidin D, hydroxyurea, idarubicin, ifosfamide, irinotecan, lomustine (CCNU), maytansine, mechlorethamine, melphalan, 6-mercaptopurine, methotrexate, mithramycin, mitomycin C, mitoxantrone, nitroimidazole, paclitaxel, palytoxin, plicamycin, procarbizine, rhizoxin, streptozotocin, tenoposide, 6-thioguanine, thioTEPA, topotecan, vinblastine, vincristine, vinorelbine, VP-16 and VM-26.

In some typical embodiments, suitable cytotoxic agents include, for example, DNA minor groove binders (e.g., enediynes and lexitropsins, a CBI compound; see also U.S. Pat. No. 6,130,237), duocarmycins (see U.S. Publication No. 20060024317), taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In some embodiments, the Drug unit is an anti-tubulin agent. Examples of anti-tubulin agents include, but are not limited to, taxanes (e.g., Taxol® (paclitaxel), Taxotere® (docetaxel)), T67 (Tularik) and vinca alkyloids (e.g., vincristine, vinblastine, vindesine, and vinorelbine). Other anti-tubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin.

In certain embodiments, the cytotoxic agent is maytansine or a maytansinoid, another group of anti-tubulin agents. (ImmunoGen, Inc.; see also Chari et al., 1992, Cancer Res. 52:127-131 and U.S. Pat. No. 8,163,888).

In some embodiments, the Drug unit is an auristatin. Auristatins include, but are not limited to, AE, AFP, AEB, AEVB, MMAF, and MMAE. The synthesis and structure of auristatins are described in U.S. Patent Application Publication Nos. 2003-0083263, 2005-0238649 2005-0009751, 2009-0111756, and 2011-0020343; International Patent Publication No. WO 04/010957, International Patent Publication No. WO 02/088172, and U.S. Pat. Nos. 7,659,241 and 8,343,928; each of which is incorporated by reference in its entirety and for all purposes. Exemplary auristatins of the present invention bind tubulin and exert a cytotoxic or cytostatic effect on the desired cell line.

Exemplary auristatin Drug units have the following formula or a pharmaceutically acceptable salt thereof wherein the wavy line indicates site of attachment to the Linker unit:

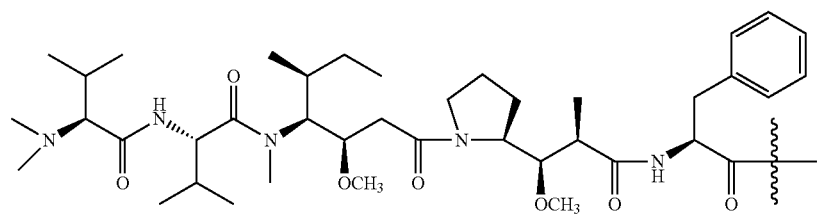

-continued

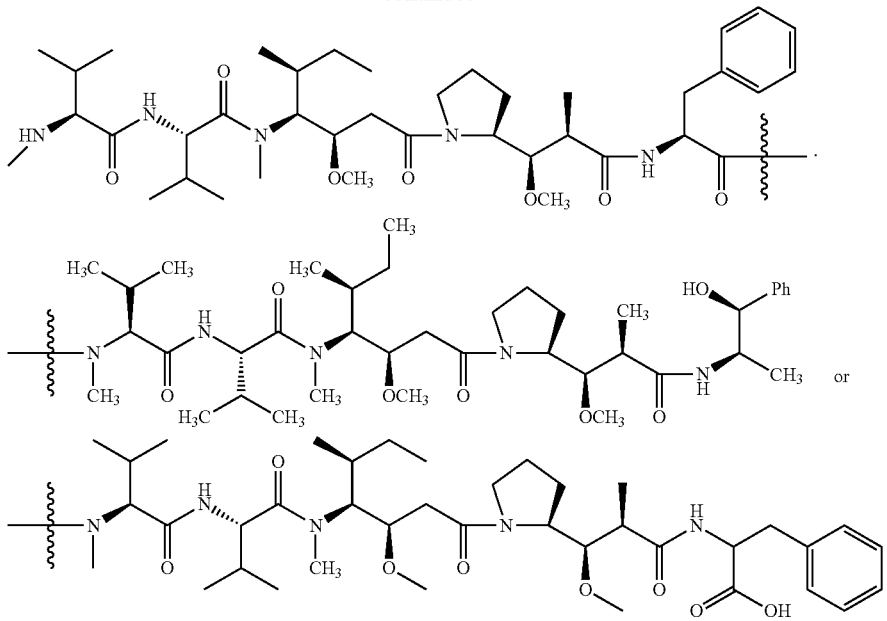

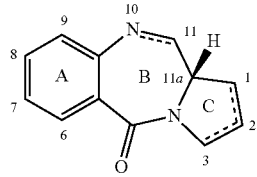

but can differ in the number, type and position of substituents, in both their aromatic A rings and pyrrolo C rings, and in the degree of saturation of the C ring. In the B-ring there is either an imine (N=C), a carbinolamine(NH—CH(OH)), or a carbinolamine methyl ether (NH—CH(OMe)) at the N10-C11 position, which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site. The ability of PBDs to faun an adduct in the minor groove enables them to interfere with DNA processing, hence their use as antitumour agents. The biological activity of these molecules can be potentiated by, for example, joining two PBD units together through their C8/C'-hydroxyl functionalities via a flexible alkylene linker. The PBD dimers are thought to form sequence-selective DNA lesions such as the palindromic 5'-Pu-GATC-Py-3' interstrand crosslink which is thought to be mainly responsible for their biological activity.

There are a number of different assays that can be used for determining whether a Ligand-Drug Conjugate exerts a cytostatic or cytotoxic effect on a cell line. In one example for determining whether a Ligand-Drug Conjugate exerts a cytostatic or cytotoxic effect on a cell line, a thymidine incorporation assay is used. For example, cells at a density of 5,000 cells/well of a 96-well plated is cultured for a 72-hour period and exposed to 0.5 µCi of $^3$H-thymidine during the final 8 hours of the 72-hour period, and the incorporation of $^3$H-thymidine into cells of the culture is measured in the presence and absence of Ligand-Drug Conjugate. The Ligand-Drug Conjugate has a cytostatic or cytotoxic effect on the cell line if the cells of the culture have reduced $^3$H-thymidine incorporation compared to cells of the same cell line cultured under the same conditions but not contacted with the Ligand-Drug Conjugate.

In another example, for determining whether a Ligand-Drug Conjugate exerts a cytostatic or cytotoxic effect on a cell line, cell viability is measured by determining in a cell the uptake of a dye such as neutral red, trypan blue, or ALAMAR™ blue (see, e.g., Page et al., 1993, *Intl. J. of Oncology* 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytoxicity (Skehan et al., 1990, *J. Nat'l Cancer Inst.* 82:1107-12). Preferred Ligand-Drug Conjugates include those with an IC$_{50}$ value (defined as the mAB concentration that gives 50% cell kill) of less than 1000 ng/ml, preferably less than 500 ng/ml, more preferably less than 100 ng/ml, even most preferably less than 50 or even less than 10 ng/ml on the cell line.

General procedures for linking a drug to linkers are known in the art. See, for example, U.S. Pat. Nos. 8,163,888, 7,659,241, 7,498,298, U.S. Publication No. US20110256157 and International Application Nos. WO2011023883, and WO2005112919.

M$^1$—The succinimide

A non-hydrolyzed succinimide (also referred to herein as a succinimide ring) conjugated to the Ligand unit via a thioether linkage can be represented as follows wherein R represents the remainder of the Linker unit optionally conjugated to a Drug unit, Detection unit or Stabilizing Unit:

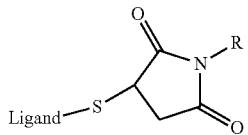

A hydrolyzed succinimide (also referred to herein as a hydrolyzed succinimide ring) conjugated to the Ligand unit via a thioether linkage can be represented as one of its two positional isomers as follows wherein R represents the remainder of the Linker unit optionally conjugated to a Drug unit, Detection unit or Stabilizing Unit:

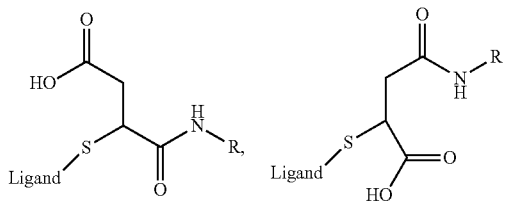

It will be understood for the non-hydrolyzed succinimides and hydrolyzed succinimide representations, there can be from 1 to 20, preferably 1 to 12, 1 to 10 or 1 to 8 self-stabilizing linkers conjugated to each Ligand. In some aspects, there are from 1 to 20, preferably 1 to 12, 1 to 10 or 1 to 8 drug-linkers conjugated to each Ligand. Additionally, for the conjugates described herein where a Ligand is not attached, the succinimide is in an unsaturated form as a maleimide (capable of reactive with a thiol or the Ligand).

Basic Units

In Formula I, as well as the other formulae comprising a self-stabilizing linker ($L^{SS}$), the Basic unit (BU) can be essentially any base capable of facilitating a hydroxide ion (or water) attack to hydrolyze a nearby succinimide group. Accordingly, BU represents any "base" but is typically a group comprising a tethered amine or nitrogen containing heterocycle; the amine or nitrogen containing heterocycle acting as the base of the Basic unit. Representative amines include —N($R^3$)($R^4$) wherein $R^3$ and $R^4$ are independently selected from H or $C_{1-6}$ alkyl, preferably H or methyl,

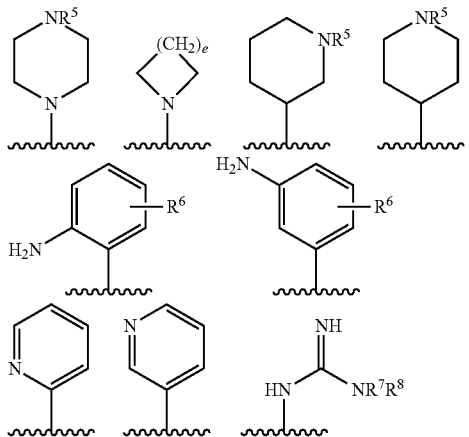

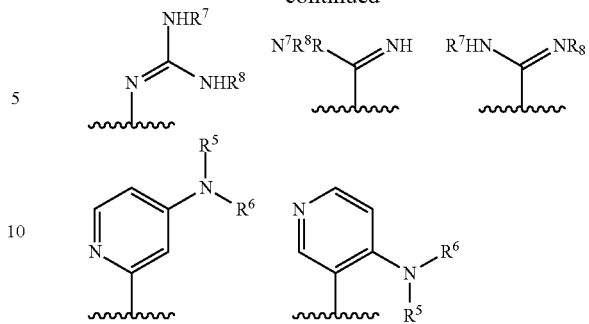

wherein $R^5$, $R^6$, $R^7$ and $R^8$ are, at each occurrence, independently selected from hydrogen or $C_{1-6}$ alkyl, preferably H or methyl, and e is 0-4. In the formulae above, the wavy line indicates the point of attachment to a tethering group (typically an alkylene linker —$(C(R^9)(R^{10}))_x$— wherein the subscript x is an integer of from 0 to 6 (or 1 to 6) provided that if x is 0 there are no less than 2 intervening atoms between the base of the Basic unit and the nitrogen atom of the succinimide (hydrolyzed or non-hydrolyzed) or dilactam and $R^9$ and $R^{10}$ are independently selected from H or $C_{1-3}$ alkyl. In some aspects, the alkylene linker is —$(CH_2)_x$— wherein the subscript x is an integer of from 0 to 6 (or 1 to 6) provided that if x is 0 there are no less than 2 intervening atoms between the base of the Basic unit and the nitrogen atom of the succinimide (hydrolyzed or non-hydrolyzed) or dilactam. The subscript x is preferably 0 to 4, 1 to 4, or from 1 to 3, or from 2 to 3, or from 2 to 4, but can also be 0, 1, 2, 3 or 4. Accordingly, the Basic unit, will in some embodiments, be selected from the group consisting of —$(CH_2)_x$ $NH_2$, —$(CH_2)_x NHR^a$, and —$(CH_2)_x NR^a_2$, wherein x is an integer of from 0 to 4, 1 to 4, or from 1 to 3, or from 2 to 3, or from 2 to 4, but can also be 0, 1, 2, 3 or 4, and each $R^a$ is independently selected from the group consisting of $C_{1-6}$ alkyl and $C_{1-6}$ haloalkyl, or two $R^a$ groups are combined with the nitrogen to which they are attached to form an azetidinyl, pyrrolidinyl or piperidinyl group. In some aspects, the base will be a nitrogenous base.

Hydrolysis Enhancers (HE) and Electron-Withdrawing Groups

The hydrolysis enhancers (HE) of Formula I, as well as the other formulae comprising a self-stabilizing linker ($L^{SS}$), can be essentially any electron-withdrawing group capable of facilitating the hydrolysis of a nearby succinimide group. The hydrolysis is further facilitated by the Basic unit (BU) assisting a hydroxide ion (or water) attack to hydrolyze a nearby succinimide group; or to render the nearby succinimide group more susceptible to hydrolysis. Accordingly, HE can include a functional group that draws electrons away from a reaction center. Exemplary electron withdrawing groups include, but are not limited to, —C(=O), (=O), —CN, —$NO_2$, —$CX_3$, —X, —COOR, —$CONR_2$, —COR, —COX, —$SO_2R$, —$SO_2OR$, —$SO_2NHR$, —$SO_2NR_2$, —$PO_3R_2$, —P(O)($CH_3$)NHR, NO, —$NR_3^+$, —CR=$CR_2$, and —C≡CR wherein X is F, Br, Cl, or I, and R is, at each occurrence, independently selected from the group consisting of hydrogen and $C_{1-6}$ alkyl. Exemplary electron withdrawing groups can also include aryl groups (e.g., phenyl) and certain heteroaryl groups (e.g., pyridine). The term "electron withdrawing groups" includes aryls or heteroaryls further substituted with electron withdrawing groups.

In some embodiments, HE comprises a carbonyl, sulfonyl or phosphoryl moiety. In some embodiments, the hydrolysis enhancer (HE) is —CH$_2$C(O)—, —C(O)—, —C(O)CH$_2$—, —CH$_2$CH$_2$C(O)—, or —CH$_2$C(O)NH—.

In some embodiments wherein HE is directly linked to the secondary linker assembly or Drug unit or Stability unit or Detection unit, HE will comprise a reactive site suitable for attachment to the optional secondary linker assembly or Drug unit. In some aspects, the electron withdrawing group will itself act as both the electron withdrawing group and a reactive site for attachment to the optional secondary linker assembly or Drug unit (e.g., —C(=O)—).

The Optional Secondary Linker Assembly ($L^O$)

As noted above, the optional secondary linker assembly can be represented by the formula:

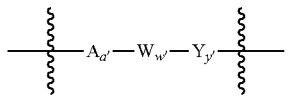

wherein -A- is an optional Stretcher unit, the subscript a' is 0 or 1; —W— is an optional Cleavable unit, the subscript w' is 0 or 1; and —Y— is an optional Spacer unit, and the subscript y' is 0 or 1. The wavy line adjacent to the optional Stretcher unit indicates the site of attachment to the self-stabilizing linker assembly and the wavy line adjacent to the optional Spacer unit indicates the site of attachment to the Drug unit.

General methods of linking a Drug unit, a Detection unit, or a Stability unit to a Ligand unit are known in the art and linkers known in the art can be adapted for use with a self-stabilizing linker assembly or modified to include a basic component and/or electron withdrawing group using the teachings described herein. For example, auristatin and maytansine ADCs are currently in clinical development for the treatment of cancer. Monomethyl auristatin E is conjugated through a protease cleavable peptide linker to an antibody, monomethyl auristatin F is conjugated directly to an antibody through maleimidocaproic acid, DM1 is conjugated through a disulfide or directly through the heterobifunctional SMCC linker, and DM4 is conjugated through a disulfide linker. These linker systems can be adapted for use with a self-stabilizing linker assembly or modified to include a basic component and/or electron withdrawing group using the teachings described herein and provide release of drug by a cleavable or non-cleavable system depending on the linker system used. Disulfide, thioether, peptide, hydrazine, ester, or carbamate bonds are all examples of bonds that can be used to connect a Drug Unit to a Linker Unit. Stretcher units, Cleavable units, and Spacer units are described in more detail below.

Also contemplated within the present invention are branched linkers. Accordingly, in one aspect, the Stretcher unit is designed in such a way to allow branching within the Linker unit, e.g., the attachment of more than one Drug unit or Detection unit or Stabilizing unit to each self-stabilizing linker assembly, as represented by the following formula:

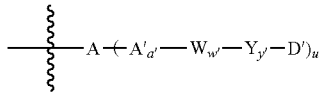

wherein the wavy line indicates the site of attachment to the self-stabilizing linker assembly, —W— is an optional Cleavable unit, the subscript w' is 0 or 1; —Y— is an optional Spacer unit, the subscript y' is 0 or 1, u is from 2 to 20 (preferably from 2 to 10); A is a Stretcher unit, A' is an optional Stretcher unit component at the terminus of A; and a' is 0 or 1. Each A', W, Y, and D' can be the same or different. Each Cleavable unit can be attached to the Stretcher unit (either A or A') through the same or different functional group on the Stretcher unit. In some aspects, D' is a Drug unit D.

Exemplary Ligand-Functional Agent Conjugates or Ligand-Drug Conjugates having either branched or non-branched linkers have the following formulae:

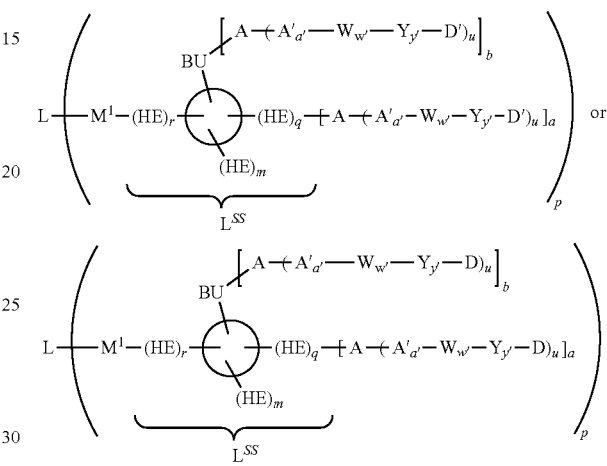

or a salt thereof (e.g., pharmaceutically acceptable salt), wherein each of L, M$^1$, HE, BU, D', and the subscripts p, a, b, m, q, and r have the meanings provided for Formula I and any of the selected embodiments for Formula I, D is a Drug unit, the circle represents a scaffold that can be C$_{1-8}$ alkylene, C$_{1-8}$ heteroalkylene, C$_{6-10}$ arylene, or C$_{4-10}$ heteroarylene, and optionally comprises a reactive site suitable for attachment to A, W, Y or D' (or D as the case may be); —W— is an optional Cleavable unit, the subscript w' is 0 or 1; —Y— is an optional Spacer unit, the subscript y' is 0 or 1, A is a Stretcher unit, A' is an optional Stretcher unit component at the terminus of A; a' is 0 or 1; and u is from 1 to 20 (preferably from 1 to 10) wherein when u is from 2 to 20 A is present and when u is 1, A can be present or absent. Each A', W, Y, and D' (or D as the case may be) can be the same or different. Each Cleavable unit can be attached to the Stretcher unit (either A or A') through the same or different functional group on the Stretcher unit. In some aspects, w' is 1. In some aspects, w' is 1 and a' is 0. In aspects, wherein the linker isn't branched u is 1 and a' is 0. In other aspects, wherein the linker is branched, u is from 2 to 20 (preferably from 2 to 10). In each of these selected embodiments, the circle can represent a scaffold that is alkylene or C$_{1-8}$ heteroalkylene (preferably C$_{1-4}$ alkylene or C$_{1-4}$ heteroalkylene) or C$_{1-3}$ alkylene or C$_{1-3}$ heteroalkylene. In some such aspects, the alkylene is straight chain or branched.

Ligand-Functional Agent Conjugates having either branched or non-branched linkers can be represented by the following formulas:

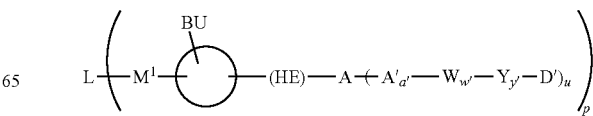

-continued

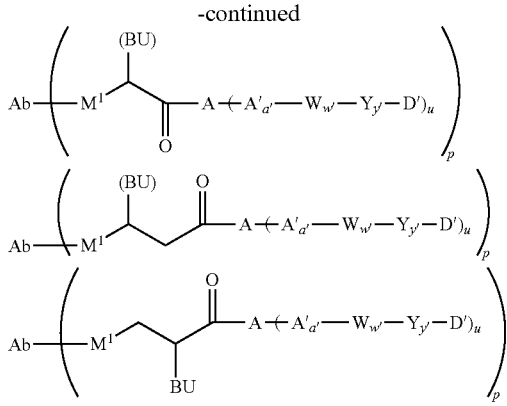

or a salt thereof (e.g., pharmaceutically acceptable salt), wherein each of L, $M^1$, HE, BU, D', and the subscript p have the meanings provided for Formula I and any of the selected embodiments for Formula I, the circle represents a scaffold that can be $C_{1-8}$ alkylene, $C_{1-8}$ heteroalkylene, $C_{6-10}$ arylene, or $C_{4-10}$ heteroarylene, and optionally comprises a reactive site suitable for attachment to A, W, Y or D', —W— is an optional Cleavable unit, the subscript w' is 0 or 1; —Y— is an optional Spacer unit, the subscript y' is 0 or 1, A is a Stretcher unit, A' is an optional Stretcher unit component at the terminus of A; a' is 0 or 1; and u is from 1 to 20 (preferably from 1 to 10), wherein when u is from 2 to 20 A is present and when u is 1, A can be present or absent. Each A', W, Y, and D' can be the same or different. Each Cleavable unit can be attached to the Stretcher unit (either A or A') through the same or different functional group on the Stretcher unit. In some aspects, w' is 1. In some aspects, w' is 1 and a' is 0. In aspects, wherein the linker isn't branched u is 1, a' is 0, and A can be present or absent. In other aspects, wherein the linker is branched u is from 2 to 20 (preferably from 2 to 10).

Ligand-Drug Conjugates having either branched or non-branched linkers can be represented by the following formulas:

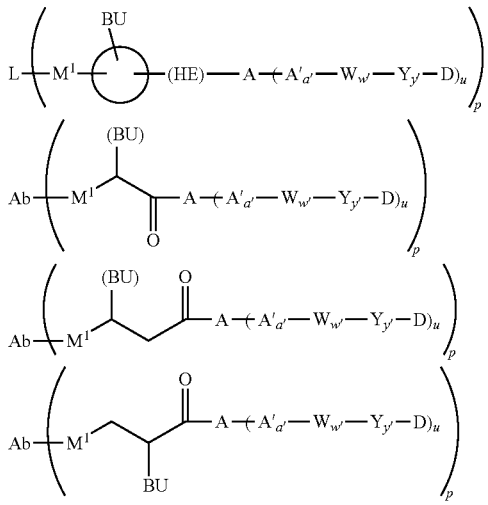

or a salt thereof (e.g., pharmaceutically acceptable salt), wherein each of L, $M^1$, HE, BU, and the subscript p have the meanings provided for Formula I and any of the selected embodiments for Formula I, D is a Drug unit, the circle represents a scaffold that can be $C_{1-8}$ alkylene, $C_{1-8}$ heteroalkylene, $C_{6-10}$ arylene, or $C_{4-10}$ heteroarylene, and optionally comprises a reactive site suitable for attachment to A, W, Y or D, —W— is an optional Cleavable unit, the subscript w' is 0 or 1; —Y— is an optional Spacer unit, the subscript y' is 0 or 1, A is a Stretcher unit, A' is an optional Stretcher unit component at the terminus of A; a' is 0 or 1; and u is from 1 to 20 (preferably from 1 to 10), wherein when u is from 2 to 20 A is present and when u is 1, A can be present or absent. Each A', W, Y, and D can be the same or different. Each Cleavable unit can be attached to the Stretcher unit (either A or A') through the same or different functional group on the Stretcher unit. In some aspects, w' is 1. In some aspects, w' is 1 and a' is 0. In aspects, wherein the linker isn't branched u is 1, a' is 0, and A can be present or absent. In other aspects, wherein the linker is branched u is from 2 to 20 (preferably from 2 to 10).

Functional Agent-Linker Conjugates having either branched or non-branched linkers can be represented by the following formulas:

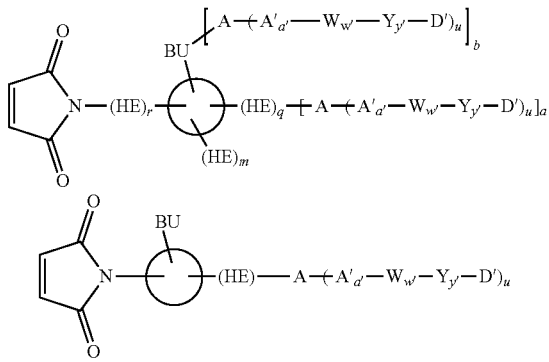

or a salt thereof (e.g., pharmaceutically acceptable salt), wherein each of HE, BU, D', and the subscripts p, a, b, m, q, and r have the meanings provided for Formula I and any of the selected embodiments for Formula I, the circle represents a scaffold that can be $C_{1-8}$ alkylene, $C_{1-8}$ heteroalkylene, $C_{6-10}$ arylene, or $C_{4-10}$ heteroarylene, and optionally comprises a reactive site suitable for attachment to A, W, Y or D'; W— is an optional Cleavable unit, the subscript w' is 0 or 1; —Y— is an optional Spacer unit, the subscript y' is 0 or 1, A is a Stretcher unit, A' is an optional Stretcher unit component at the terminus of A; a' is 0 or 1; and u is from 1 to 20 (preferably from 1 to 10, wherein when u is from 2 to 20, A is present and when u is 1, A can be present or absent. Each A', W, Y, and D' can be the same or different. Each Cleavable unit can be attached to the Stretcher unit (either A or A') through the same or different functional group on the Stretcher unit. In some aspects, w' is 1. In some aspects, w' is 1 and a' is 0. In aspects, wherein the linker isn't branched u is 1, a' is 0, and A can be present or absent. In other aspects, wherein the linker is branched u is from 2 to 20 (preferably from 2 to 10). In each of these selected embodiments, the circle can represent a scaffold that is $C_{1-8}$ alkylene or $C_{1-8}$ heteroalkylene (preferably $C_{1-4}$ alkylene or $C_{1-4}$ heteroalkylene) or $C_{1-3}$ alkylene or $C_{1-3}$ heteroalkylene. In some such aspects, the alkylene is straight chain or branched. In each of these selected embodiments, D' can be D.

In some aspects

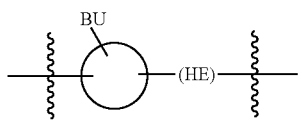

is represented by:

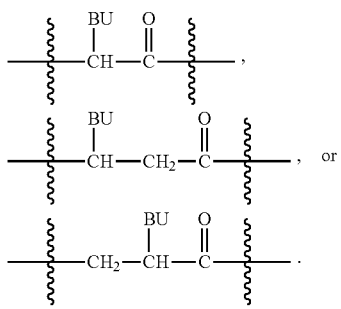

In some such aspects, D' is D.

Ligand-Linker Conjugates having either branched or non-branched linkers can be represented by the following formulas:

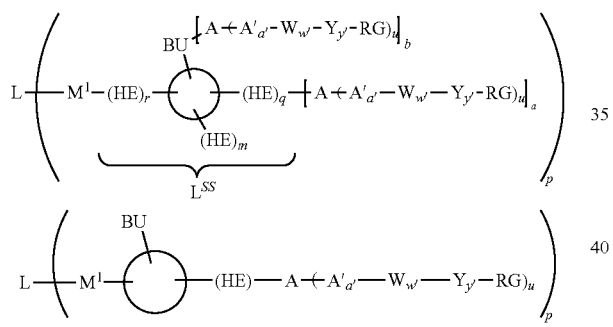

or a salt thereof (e.g., pharmaceutically acceptable salt), wherein each of L, $M^1$, HE, BU, and the subscripts p, a, b, m, q, and r have the meanings provided for Formula I and any of the selected embodiments for Formula I, the circle represents a scaffold that can be $C_{1-8}$ alkylene, $C_{1-8}$ heteroalkylene, $C_{6-10}$ arylene, or $C_{4-10}$ heteroarylene, and optionally comprises a reactive site suitable for attachment to A, W, Y or D; RG is a reactive group (comprising a reactive site) at the terminus of

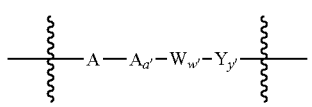

which is suitable for attaching a Drug unit (or alternatively a Detection unit or a Stability unit), W— is an optional Cleavable unit, the subscript w' is 0 or 1; —Y— is an optional Spacer unit, the subscript y' is 0 or 1, A is a Stretcher unit, A' is an optional Stretcher unit component at the terminus of A; a' is 0 or 1; and u is from 1 to 20 (preferably from 1 to 10) wherein when u is from 2 to 20, A is present and when u is 1, A can be present or absent. Each A', W, Y, and D can be the same or different. Each Cleavable unit can be attached to the Stretcher unit (either A or A') through the same or different functional group on the Stretcher unit. In some aspects, w' is 1. In some aspects, w' is 1 and a' is 0. In aspects, wherein the linker isn't branched u is 1, a' is 0, and A can be present or absent. In other aspects, wherein the linker is branched u is from 2 to 20 (preferably from 2 to 10). In each of these selected embodiments, the circle can represent a scaffold that is $C_{1-8}$ alkylene or $C_{1-8}$ heteroalkylene (preferably $C_{1-4}$ alkylene or $C_{1-4}$ heteroalkylene) or $C_{1-3}$ alkylene or $C_{1-3}$ heteroalkylene. In some such aspects, the alkylene is straight chain or branched.

In some aspects

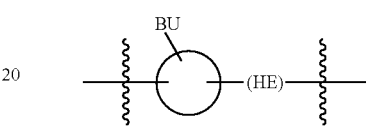

is represented by:

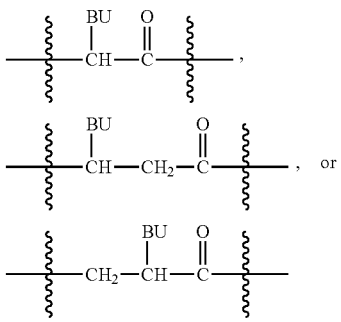

Branched or non-branched Linkers can be represented by the following formulas:

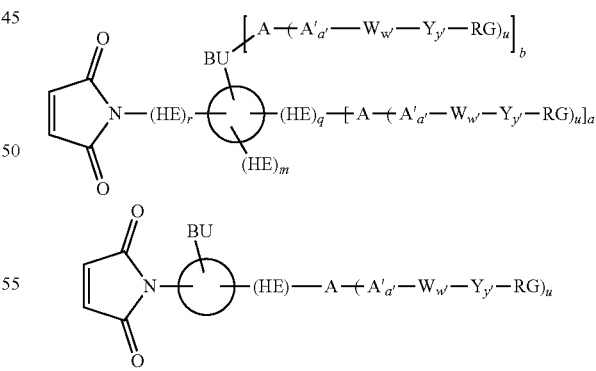

or a salt thereof (e.g., pharmaceutically acceptable salt), wherein each of the scaffold, HE, BU, and the subscripts a, b, m, q, and r have the meanings provided for Formula I and any of the selected embodiments for Formula I, the circle represents a scaffold that can be $C_{1-8}$ alkylene, $C_{1-8}$ heteroalkylene, $C_{6-10}$ arylene, or $C_{4-10}$ heteroarylene, and optionally comprises a reactive site suitable for attachment to A, W, Y or D; RG is a reactive group (comprising a reactive site) at the terminus of

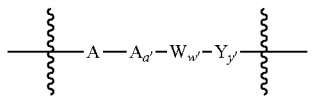

which is suitable for attaching a Drug unit (or alternatively a Detection unit or a Stabilizing unit), W— is an optional Cleavable unit, the subscript w' is 0 or 1; —Y— is an optional Spacer unit, the subscript y' is 0 or 1, A is a Stretcher unit, A' is an optional Stretcher unit component at the terminus of A; a' is 0 or 1; and u is from 1 to 20 (preferably from 1 to 10), wherein when u is from 2 to 20, A is present and when u is 1, A can be present or absent. Each A', W, Y, and D can be the same or different. Each Cleavable unit can be attached to the Stretcher unit (either A or A') through the same or different functional group on the Stretcher unit. In some aspects, w' is 1. In some aspects, w' is 1 and a' is 0. In aspects, wherein the linker isn't branched u is 1, a' is 0, and A can be present or absent. In other aspects, wherein the linker is branched u is from 2 to 20 (preferably from 2 to 10). In each of these selected embodiments, the circle can represent a scaffold that is $C_{1-8}$ alkylene or $C_{1-8}$ heteroalkylene (preferably $C_{1-4}$ alkylene or $C_{1-4}$ heteroalkylene) or $C_{1-3}$ alkylene or $C_{1-3}$ heteroalkylene. In some such aspects, the alkylene is straight chain or branched.

In some aspects

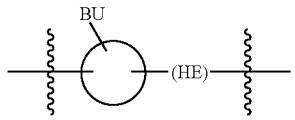

is represented by:

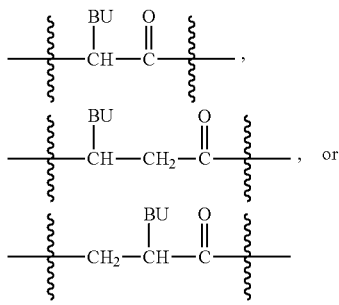

In some other aspects, exemplary Ligand-Drug Conjugates having either branched or non-branched linkers have the following formulae:

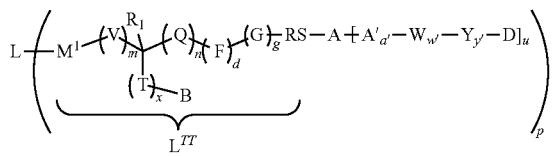

or a pharmaceutically acceptable salt thereof wherein each of L, $M^1$, V, $R^1$, T, B, Q, F, G, and RS and the subscripts p, m, x, n, d, and g have the meanings provided for Formula III and any of the selected embodiments, L is a Ligand unit, W— is an optional Cleavable unit, the subscript w' is 0 or 1; —Y— is an optional Spacer unit, the subscript y' is 0 or 1, A is a Stretcher unit, A' is an optional Stretcher unit component at the terminus of A; a' is 0 or 1; and u is from 1 to 20 (preferably from 1 to 10) wherein when u is from 2 to 20, A is present and when u is 1, A can be present or absent. Each A', W, Y, and D can be the same or different. Each Cleavable unit can be attached to the Stretcher unit (either A or A') through the same or different functional group on the Stretcher unit. In some aspects, w' is 1. In some aspects, w' is 1 and a' is 0. In aspects, wherein the linker isn't branched u is 1, a' is 0, and A can be present or absent. In other aspects, wherein the linker is branched u is from 2 to 20 (preferably from 2 to 10).

Stretcher units, Cleavable units, and Spacer units are described in more detail below.

The Stretcher Unit

The Stretcher unit (-A-), when present, extends the framework of the Linker unit to provide more distance between the self-stabilizing linker assembly and the Drug unit. A Stretcher unit is capable of linking the self-stabilizing linker assembly to the Cleavable unit when the Cleavable unit is present, the self-stabilizing linker assembly to the Spacer unit when the Cleavable unit is absent but the Spacer unit is present and the self-stabilizing linker assembly to the Drug unit when both the Cleavable unit and the Spacer unit are absent. As described, a Stretcher unit is capable of attaching to more than one Cleavable unit, Spacer unit, and/or Drug unit.

The Stretcher unit can also act to alter the physiochemical properties of the Drug-Linker depending on components of the Stretcher unit. In some aspects, the Stretcher unit will be added in order to increase the solubility of the Drug-Linker and will comprise one or multiple solubility-enhancing groups such as ionic groups or water-soluble polymers. Water-soluble typically includes any segment or polymer that is soluble in water at room temperature and includes poly(ethylene)glycol groups as well as other polymers such as polyethyleneimines.

A Stretcher unit can comprise one or multiple stretcher groups. Exemplary stretcher groups include, for example, —NH—$C_1$-$C_{10}$alkylene-, —NH—$C_1$-$C_{10}$ alkylene-NH—C(O)—$C_1$-$C_{10}$ alkylene-, —NH—$C_1$-$C_{10}$alkylene-C(O)—NH—$C_1$-$C_{10}$alkylene-, —NH—$(CH_2CH_2O)_s$—, —NH—$(CH_2CH_2O)_s$—$CH_2$—, —NH—$(CH_2CH_2NH)_s$—$(CH_2)_s$—NH—$(CH_2CH_2NH)_s$—$(CH_2)_s$—NH—C(O)—$(CH_2)_s$—NH—$(C_3$-$C_8$ carbocyclo)-, —NH-(arylene-)-, and —NH—$(C_3$-$C_8$ heterocyclo-)-, wherein each s is independently 1-10. A representative stretcher group having a carbonyl group for linkage to the remainder of the Linker unit or the Drug unit is as follow:

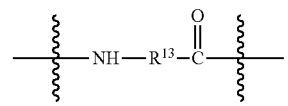

wherein $R^{13}$ is —$C_1$-$C_{10}$ alkylene-, —$C_3$-$C_8$carbocyclo-, -arylene-, —$C_1$-$C_{30}$heteroalkylene-, —$C_3$-$C_8$heterocyclo-, —$C_1$-$C_{10}$alkylene-arylene-, -arylene-$C_1$-$C_{10}$alkylene-, —$C_1$-$C_{10}$alkylene-($C_3$-$C_8$-carbocyclo)-, —($C_3$-$C_8$-carbocyclo)-$C_1$-$C_{10}$alkylene-, —$C_1$-$C_{10}$alkylene-($C_3$-$C_8$ heterocyclo)-, —($C_3$-$C_8$ heterocycle)-$C_1$-$C_{10}$ alkylene-, —$(CH_2CH_2O)_{1-10}$(—$CH_2)_{1-3}$—, or —$(CH_2CH_2NH)_{1-10}$(—$CH_2)_{1-3}$—. In some embodiments, $R^{13}$ is —$C_1$-$C_{10}$ alkylene- or —$C_1$-$C_{30}$heteroalkylene-. In some embodiments, $R^{13}$ is —$C_1$-$C_{10}$ alkylene-, —$(CH_2CH_2O)_{1-10}$(—$CH_2)_{1-3}$—, or —(CH$_2$CH$_2$NH)$_{1-10}$(—CH$_2$)$_{1-3}$—. In some embodiments, R$^{13}$ is —C$_1$-C$_{10}$ alkylene-polyethyleneglycol, or polyethyleneimine.

Non-cleavable drug release systems are known in the art and can be adapted for use with the self-stabilizing linker assemblies of the present invention as Stretcher units and/or Spacer units. A non-cleavable linker in capable of linking a Drug unit to a Ligand in a generally stable and covalent manner and is substantially resistant to acid-induced cleavage, light-induced cleavage, peptidase- or esterase-induced cleavage, and disulfide bond cleavage. Drug is released from Ligand Drug Conjugates containing non-cleavable linkers via alternative mechanisms, such as proteolytic ligand degradation.

Cross-linking reagents that form non-cleavable linkers between maytansinoid drugs and ligands are well known in the art and can adapted for use herein. Exemplary cross-linking reagents that form non-cleavable linkers between the maytansinoid drugs and ligands comprise a maleimido or haloacetyl-based moiety. They include N-succinimidyl 4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), κ-maleimidoundecanoic acid N-succinimidyl ester (KMUA), γ-maleimidobutyric acid N-succinimidyl ester (GMBS), c-maleimidocaproic acid N-hydroxysuccinimide ester (EMCS), m-maleimidobenzoyl-N-hydroxysuccinimide ester (MBS), N-(.alpha.-maleimidoacetoxy)-succinimide ester [AMAS], succinhnidyl-6-(β-maleimidopropionamido)hexanoate (SMPH), N-succinimidyl 4-(p-maleimidophenyl)-butyrate (SMPB), and N-(p-maleimidophenyl)isocyanate (PMPI), N-succinimidyl-4-(iodoacetyl)-aminobenzoate (STAB), N-succinimidyl iodoacetate (SIA), N-succinimidyl bromoacetate (SBA) and N-succinimidyl 3-(bromoacetamido)propionate (SBAP). Additional Stretcher units for use in combination with the self-stabilizing linker assembly of the present invention can be found, for example, in U.S. Pat. No. 8,142,784, incorporated herein by reference in its entirety and for all purposes.

The Cleavable Unit

The Cleavable unit (—W—), when present, is capable of linking the self-stabilizing linker assembly to the Spacer unit when the Spacer unit is present or the self-stabilizing linker assembly to the Drug unit when the Spacer unit is absent. The linkage from the self-stabilizing linker assembly to the Spacer unit or to the Drug unit can be directly from the self-stabilizing linker assembly when the Stretcher unit is absent or via the Stretcher unit if the Stretcher unit is present.

In some embodiment, the Cleavable unit will be directly conjugated to the self-stabilizing linker assembly on one end and to the Drug unit on the other end. In other embodiments, the Cleavable unit will be directly conjugated to the Stretcher unit on one end and to the Drug unit on the other end. In yet other embodiments, the Cleavable unit will be directly conjugated to the Stretcher unit on one end and to the Spacer unit on the other end. In even yet other embodiments, the Cleavable unit will be directly conjugated to the self-stabilizing linker assembly on one end and to the Spacer unit on the other end. Any of specifically described self-stabilizing linker assemblies described herein can be used in these embodiments.

The Cleavable unit is capable of forming a cleavable bond with a Drug unit or a Spacer unit. Reactive groups for forming cleavable bonds can include, for example, sulfhydryl groups to form disulfide bonds, aldehyde, ketone, or hydrazine groups to form hydrazone bonds, carboxylic or amino groups to form peptide bonds, and carboxylic or hydroxy groups to form ester bonds.

The nature of the Cleavable unit can vary widely. For example, cleavable linkers include disulfide containing linkers that are cleavable through disulfide exchange, acid-labile linkers that are cleavable at acidic pH, and linkers that are cleavable by hydrolases, peptidases, esterases, and glucoronidases.

In some aspects, the structure and sequence of the Cleavable unit is such that the unit is cleaved by the action of enzymes present at the target site. In other aspects, the Cleavable unit can be cleavable by other mechanisms. The Cleavable unit can comprise one or multiple cleavage sites.

In some embodiments, the Cleavable unit will comprise one amino acid or one or more sequences of amino acids. The Cleavable unit can comprise, for example, a monopeptide, a dipeptide, tripeptide, tetrapeptide, pentapeptide, hexapeptide, heptapeptide, octapeptide, nonapeptide, decapeptide, undecapeptide or dodecapeptide unit.

Each amino acid can be natural or unnatural and/or a D- or L-isomer provided of course that there is a cleavable bond. In some embodiments, the Cleavable unit will comprise only natural amino acids. In some aspects, the Cleavable unit will comprise 1 to 12 amino acids in contiguous sequence.

In some embodiments, each amino acid is independently selected from the group consisting of alanine, arginine, aspartic acid, asparagine, histidine, glycine, glutamic acid, glutamine, phenylalanine, lysine, leucine, serine, tyrosine, threonine, isoleucine, proline, tryptophan, valine, cysteine, methionine, selenocysteine, ornithine, penicillamine, β-alanine, aminoalkanoic acid, aminoalkynoic acid, aminoalkanedioic acid, aminobenzoic acid, amino-heterocyclo-alkanoic acid, heterocyclo-carboxylic acid, citrulline, statine, diaminoalkanoic acid, and derivatives thereof. In some embodiments, each amino acid is independently selected from the group consisting of alanine, arginine, aspartic acid, asparagine, histidine, glycine, glutamic acid, glutamine, phenylalanine, lysine, leucine, serine, tyrosine, threonine, isoleucine, proline, tryptophan, valine, cysteine, methionine, and selenocysteine. In some embodiments, each amino acid is independently selected from the group consisting of alanine, arginine, aspartic acid, asparagine, histidine, glycine, glutamic acid, glutamine, phenylalanine, lysine, leucine, serine, tyrosine, threonine, isoleucine, proline, tryptophan, and valine. In some embodiments, each amino acid is selected from the proteinogenic or the non-proteinogenic amino acids.

In another embodiment, each amino acid is independently selected from the group consisting of the following L-(natural) amino acids: alanine, arginine, aspartic acid, asparagine, histidine, glycine, glutamic acid, glutamine, phenylalanine, lysine, leucine, serine, tyrosine, threonine, isoleucine, tryptophan and valine.

In another embodiment, each amino acid is independently selected from the group consisting of the following D-isomers of these natural amino acids: alanine, arginine, aspartic acid, asparagine, histidine, glycine, glutamic acid, glutamine, phenylalanine, lysine, leucine, serine, tyrosine, threonine, isoleucine, tryptophan and valine.

In some embodiments, the bond between the Cleavable unit and the Drug unit can be enzymatically cleaved by one or more enzymes, including a tumor-associated protease, to liberate the Drug unit (-D), which in one embodiment is protonated in vivo upon release to provide a Drug (D).

Useful Cleavable units can be designed and optimized in their selectivity for enzymatic cleavage by a particular enzyme, for example, a tumor-associated protease. In one embodiment, a linkage (or bond) between the Cleavable unit and the Drug unit or Spacer unit is that which cleavage is catalyzed by cathepsin B, C and D, or a plasmin protease.

In certain embodiments, the Cleavable unit can comprise only natural amino acids. In other embodiments, the Cleavable unit can comprise only non-natural amino acids. In some embodiments, the Cleavable unit can comprise a natural amino acid linked to a non-natural amino acid. In some embodiments, the Cleavable unit can comprise a natural amino acid linked to a D-isomer of a natural amino acid.

An exemplary Cleavable unit is the dipeptide -Val-Cit-, -Phe-Lys- or -Val-Ala.

In some embodiments, the Cleavable unit will comprises a peptide and will comprise from 1 to 12 amino acids. In some such embodiments, the peptide will be conjugated directly to the Drug unit and the Spacer unit will be absent. In some such embodiments, the Stretcher unit and Spacer unit will be absent. In one aspect, the peptide will be a dipeptide.

In some embodiments, the Cleavable unit —$W_w$— will be represented by -(-AA-)$_{1-12}$-, or (-AA-AA-)$_{1-6}$ wherein AA is at each occurrence independently selected from natural or non-natural amino acids. In one aspect, AA is at each occurrence independently selected from natural amino acids. One of skill in the art would appreciate that amino acids are typically linked to the Drug unit or Spacer unit through functional units present in the amino acid, e.g., its carboxylic acid or amino termini.

In some such aspects, the Ligand Drug Conjugates and Drug-Linkers are represented by the following formulae or salts thereof wherein L, $L^{SS}$, $L^{TT}$ A, a', AA, Y, y', D, and p are as defined in any of the embodiments described herein and f is an integer from 1 to 12:

$$L \text{—(} L^{TT} \text{—} A_{a'} \text{—} AA_f \text{—} Y_{y'} \text{—} D)_p,$$
$$L \text{—(} L^{SS} \text{—} A_{a'} \text{—} AA_f \text{—} Y_{y'} \text{—} D)_p,$$
$$L \text{—(} L^{TT} \text{—} A_{a'} \text{—} AA_f \text{—} D)_p,$$
$$L \text{—(} L^{SS} \text{—} A_{a'} \text{—} AA_f \text{—} D)_p,$$
$$L \text{—(} L^{TT} \text{—} AA_f \text{—} D)_p, \quad L \text{—(} L^{SS} \text{—} AA_f \text{—} D)_p,$$
$$L^{TT} \text{—} A_{a'} \text{—} AA_f \text{—} Y_{y'} \text{—} D, \quad L^{SS} \text{—} A_{a'} \text{—} AA_f \text{—} Y_{y'} \text{—} D,$$
$$L^{TT} \text{—} A_{a'} \text{—} AA_f \text{—} D, \quad L^{SS} \text{—} A_{a'} \text{—} AA_f \text{—} D,$$
$$L^{TT} \text{—} AA_f \text{—} D, \quad \text{or} \quad L^{SS} \text{—} AA_f \text{—} D$$

It will be understood that although not reflected in the above formulae, such formulaes can be modified as taught herein to include branched linkers, i.e., multiple Drug units can be attached to each self-stabilizing linker assembly.

In other aspects, the Cleavable unit will comprise a glucoronide unit, preferably 1 or 2 glucoronide units. In some such embodiments, the Glucuronide unit comprises a sugar moiety (Su) linked via a glycoside bond (—O'—) to a self-immolative Spacer:

—[Su—O'—Y]—

The glycosidic bond (—O'—) is typically a β-glucuronidase-cleavage site, such as a bond cleavable by human, lysosomal β-glucuronidase.

In some aspects, —[Su—O'—Y]— is represented by the following formula:

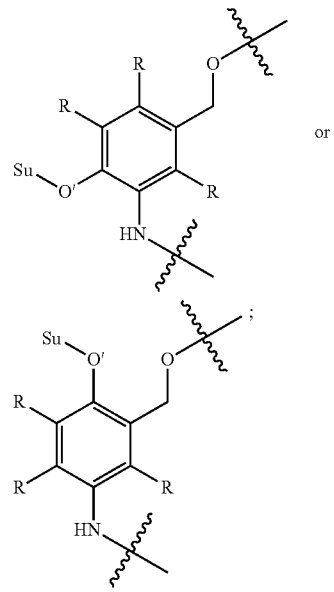

wherein Su is a Sugar moiety, —O'— represents a glycosidic bond; each R is independently hydrogen, a halogen, —CN, or —NO$_2$; wherein the wavy bond adjacent to the nitrogen atom indicates covalent attachment to the Stretcher unit or to the Ligand and the wavy bond adjacent to the oxygen indicates covalent attachment to the Spacer unit or to the Drug unit. An exemplary Linker unit comprising a glucoronide prior to conjugation to an antibody and post conjugation is as follows wherein the wavy line indicates attachment to a Drug unit or Spacer unit and Ab represents an antibody and S is a sulfur atom of the antibody. It will be understood that more than one self-stabilizing assembly can be attached to each antibody:

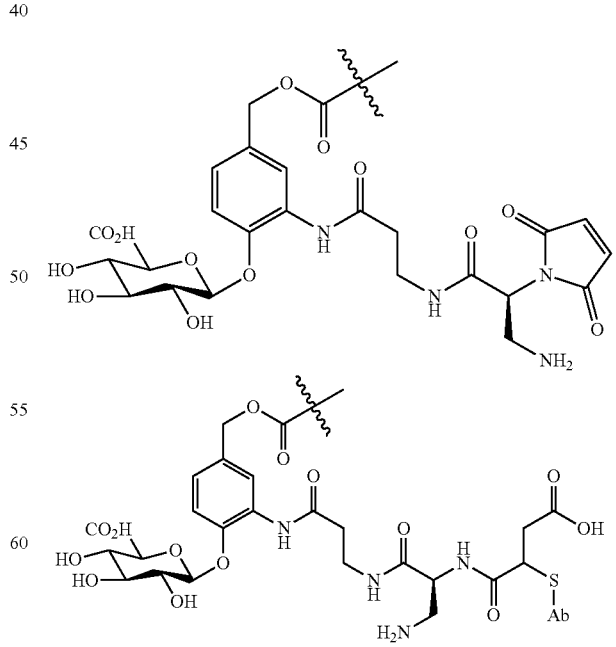

In some embodiments, the Cleavable unit itself will comprise a sulfur atom that is capable of forming a bond with a sulfur atom of a Spacer unit or Drug unit to form a disulfide or hindered disulfide. Cleavage occurs between the two sulfur atoms of the disulfide. In some such embodiments, one of the sulfur atoms is cleaved from the Drug unit and, provided there is no further release mechanism, the other sulfur atom remains attached to the Drug unit. A Linker unit comprising a Cleavable unit having a sulfur atom is capable of forming a bond with a sulfur atom of a Spacer unit or Drug unit to form a disulfide or hindered disulfide Exemplary linkers include, for example, the following Drug-Linker wherein the wavy line indicates the site of attachment to the remainder of the Linker unit, D is a maytansinoid drug, and $R_a$ and $R_b$ are independently selected from H or methyl.

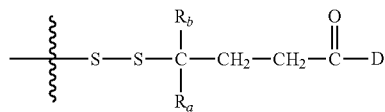

A variety of disulfide linkers are known in the art and can adapted for use in the present invention, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate), SMPT (N-succinimidyl-oxycarbonyl-alpha-methyl-alpha-(2-pyridyl-dithio) toluene), and SPP (N-succinimidyl 4-(2-pyridyldithio) pentanoate). (See, e.g., Thorpe et al., 1987, *Cancer Res.* 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.)

In some embodiments, the cleavable linker is pH-sensitive and will comprise, for example, an acid-labile linker that is hydrolyzable in the lysosome (e.g., a hydrazone, semicarbazone, thiosemicarbazone, cis-aconitic amide, orthoester, acetal, or ketal group) can be used. (See, e.g., U.S. Pat. Nos. 5,122,368; 5,824,805; 5,622,929; Dubowchik and Walker, 1999, *Pharm. Therapeutics* 83:67-123; Neville et al., 1989, *Biol. Chem.* 264:14653-14661.) Such linkers are relatively stable under neutral pH conditions, such as those in the blood, but are unstable at below pH 5.5 or 5.0, the approximate pH of the lysosome.

In some embodiments, the Cleavable unit will be conjugated directly to the Drug unit and the Spacer unit will be absent and the Cleavable unit will be linked to the Drug unit via a cleavable peptide, disulfide, or hydrazone bond.

The Spacer Unit

The Spacer unit (—Y—), when present, links a Cleavable unit to the Drug unit or a Stretcher unit to the Drug unit or a self-stabilizing linker assembly to a Drug unit. Like the Stretcher unit, the Spacer unit, when present can act to extend the framework of the Linker unit. The Spacer unit can comprise multiple self-immolative or non-self immolative groups. In some embodiments, the Spacer unit comprises one or more self-immolative groups. In this context, the term "self-immolative group" refers to a bifunctional chemical moiety that is capable of covalently linking together two spaced chemical moieties into a normally stable tripartite molecule. It will spontaneously separate from the second chemical moiety if its bond to the first moiety is cleaved. In other embodiments, the Spacer unit is not self-immolative. In these embodiments, part or all of the Spacer unit remains attached to the Drug unit.

In some embodiments, —Y— is a self-immolative group and is linked to a Cleavable unit via the methylene carbon atom of the self-immolative group, and linked connected directly to the Drug unit via a carbonate, carbamate or ether group.

In some embodiments, —Yy- is a p-aminobenzyl alcohol (PAB) unit whose phenylene portion is optionally substituted with —$C_1$-$C_8$ alkyl, —O—($C_1$-$C_8$ alkyl), -halogen, -nitro or -cyano.

In another embodiment, —Yy- can be a carbonate group. An unsubstituted PAB unit is as follows:

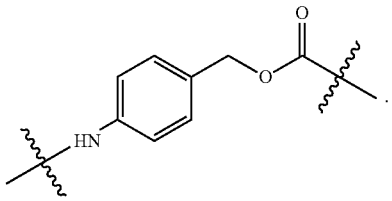 [SMILES: *Nc1ccc(COC(*)=O)cc1]

Other examples of self-immolative groups include, but are not limited to, aromatic compounds that are electronically similar to the PAB group such as 2-aminoimidazol-5-methanol derivatives (see, e.g., Hay et al., 1999, *Bioorg. Med. Chem. Lett.* 9:2237) and ortho or para-aminobenzylacetals. Spacers can be used that undergo cyclization upon amide bond hydrolysis, such as substituted and unsubstituted 4-aminobutyric acid amides (see, e.g., Rodrigues et al., 1995, *Chemistry Biology* 2:223), appropriately substituted bicyclo[2.2.1] and bicyclo[2.2.2] ring systems (see, e.g., Storm et al., 1972, *J. Amer. Chem. Soc.* 94:5815) and 2-aminophenylpropionic acid amides (see, e.g., Amsberry et al., 1990, *J. Org. Chem.* 55:5867). Elimination of amine-containing drugs that are substituted at the α-position of glycine (see, e.g., Kingsbury et al., 1984, *J. Med. Chem.* 27:1447) are also examples of self-immolative groups.

Other suitable Spacer units are disclosed in Published U.S. Patent Application No. 2005-0238649, the disclosure of which is incorporated by reference herein.

Exemplary Stretcher units, Cleavable units, and Spacer units that can be used with the present compositions and methods are described in WO 2004010957, WO 2007/038658, WO 2005/112919, U.S. Pat. Nos. 6,214,345, 7,659,241, 7,498,298, 7,968,687, 8,163,888, and U.S. Publication No. 2009-0111756, 2009-0018086, 2009-0274713, each of which is incorporated herein by reference in its entirety and for all purposes.

In embodiments wherein the Conjugates are conjugated to a Stabilizing unit or a Detection unit in lieu of a Drug unit, the optional Secondary Linker Assembly will typically be absent. In embodiments where the Secondary Linker Assembly is present, the Stretcher unit will generally be present but the Cleavable unit and the Spacer unit will be absent. The Stretcher unit will extend the framework of the Linker unit to provide more distance between the self-stabilizing assembly and the Detection unit or Stability unit. In such aspects, the Stretcher unit is capable of linking the self-stabilizing linker assembly to the Detection unit or the Stabilizing unit.

Drug Loading

The number of self-stabilizing linkers per Ligand is represented by p. In embodiments wherein the linkers are not branched, p represents the number of drug-linker molecules (or detection-linker or stability-linker molecules) per Ligand (e.g., antibody). Depending on the context, p can represent the average number of self-stabilizing linkers per Ligand (or in embodiments where the linkers are not branched, the average number of drug-linker molecules (or detection-linker or stability-linker molecules) per Ligand (e.g., antibody)). The variable p ranges from 1 to 20, typically 1 to 12, 1 to 10 and is preferably from 1 to 8. In some preferred embodiments, when p represents the average number of self-stabilizing linkers per antibody, p ranges from about 2 to about 5. In some embodiments, p is about 2, about 4, or about 8. In some preferred embodiments, when p represents the average number of drug-linker molecules per antibody, p ranges from about 2 to about 5. In some embodiments, p is about 2, about 4, or about 8. The number of D' per self-stabilizing linkers is represented by u. u ranges from 1 to 10.

The average number of Drugs units per Ligand unit in a preparation from a conjugation reaction may be characterized by conventional means such as mass spectroscopy, ELISA assay, HIC and HPLC. The quantitative distribution of Drug-Linker-Ligand conjugates in terms of p may also be determined. In some instances, separation, purification, and characterization of homogeneous Ligand-Drug Conjugates, where p is a certain value from Ligand-Drug Conjugate with other drug loadings may be achieved by means such as reverse phase HPLC or electrophoresis.

Self-Stabilizing Linker Assembly ($L^{SS}$ or $L^{TT}$) and Rates of Hydrolysis

The Self-Stabilizing linker assembly links the Ligand unit to a Stretcher unit if the Stretcher unit is present, links the Ligand unit to a Cleavable unit if the Stretcher unit is absent and a Cleavable unit is present, links the Ligand unit to a Spacer unit if the Stretcher unit and the Cleavable unit are absent and the Spacer unit is present, or links the Ligand Unit to D' (e.g., a Drug Unit) if the Stretcher unit, Cleavable unit and Spacer unit are absent. In some embodiments, the Stretcher unit, Cleavable unit, and Spacer unit will be absent and the self-stabilizing linker assembly will be conjugated directly to D' (e.g., a Drug Unit). In other embodiments, one or more of the Stretcher unit, Cleavable unit, and Spacer unit will be present.

The rate at which the thio-substituted succinimide of the Self-Stabilizing Linker when part of a Ligand-Drug Conjugate undergoes hydrolysis can be quantified using the t1/2 of hydrolysis. t1/2 of hydrolysis refers to the time taken for half of the compound of interest to hydrolyze, i.e., undergo a ring opening, under stated conditions (e.g., pH 7.4 and 22° C.). In some embodiments of the present invention, the t1/2 of hydrolysis of the thio-substituted succinimide of the Self-Stabilizing unit is less than 4 hours, preferably less than 3 hours, even more preferably, less than 2 hours, less than 1 hour, less than 45 minutes, less than 30 minutes, less than 15 minutes using the following assay and stated conditions.

The hydrolysis reaction rates of maleimido drug linkers following conjugation to antibody cysteines can be determined by mass spectrometry, as the hydrolyzed product has a molecular weight 18 daltons greater than the unhydrolyzed conjugate. Reduction of the interchain disulfides of a human IgG1 creates a single reduced cysteine on the light chain and three reduced cysteines on the heavy chain. The self-stabilizing maleimide drug-linker can then be conjugated to the reduced antibody at pH 7.4 and 22° C. and introduced to a high-resolution electrospray mass spectrometer via a reversed-phase HPLC column which separates the conjugated light and heavy chains. The masses of the conjugated light and heavy chains can thus be measured, and the peak intensities determined by standard mass spectrometry data processing software (e.g., MassLynx). By performing a series of injections over time, the disappearance of the peak corresponding to the mass of the original, unhydrolyzed conjugate and the appearance of the peak corresponding to the mass of the hydrolyzed conjugate can be monitored, the intensities of the peaks determined, and the percentage of hydrolyzed conjugate calculated at each timepoint. By plotting the hydrolysis percentage versus time, a curve is generated (e.g., using PRISM) which can be fit to a standard equation for exponential phenomena which includes a parameter for t1/2.

In some aspects, the Self-Stabilizing Linker will be designed such that the maleimide component of the Self-Stabilizing Linker does not substantially undergo hydrolysis prior to conjugation to the Ligand unit.

In some embodiments of the present invention, the t1/2 of hydrolysis of the thio-substituted succinimide of the Self-Stabilizing Linker is from about 5 or about 10 minutes to about 24 hours, preferably from about 5 or about 10 minutes to about 12 hours, more preferably from about 5 or about 10 minutes to about 5 hours, more preferably from about 5 or about 10 minutes to about 2.5 hours, even more preferably from about 5 or about 10 minutes to about 1 hour, even more preferably from about 5 or about 10 minutes to about 30 minutes, even more preferably from about 5 or about 10 minutes to about 20 minutes, and even more preferably from about 10 minutes to about 15 minutes at a pH of about 7 to about 7.5 (e.g., 7.4) and a temperature of about 22° C.

In some such embodiments wherein the t1/2 of hydrolysis is as stated above, the hydrolysis goes to completion. Complete hydrolysis is considered to be achieved if 90% of the thio-substituted succinimide hydrolyzes. Preferably, 95% or greater, 96%, 97%, 98%, 99% or 100% hydrolysis will be achieved. In some embodiments, the hydrolysis reaction will compete with a dilactam formation and will not achieve completion. In some such embodiments, at least 90% of the reaction product will be a combination of either a hydrolyzed thio-substituted succinimide Ligand-Drug Conjugate or a thio-substituted dilactam Ligand-Drug Conjugate. Preferably at least 95% or greater, 96%, 97%, 98%, 99% or 100% of the reaction product will be a combination of either a hydrolyzed thio-substituted Ligand-Drug Conjugate or a thio-substituted dilactam Ligand-Drug Conjugate. The percentage of hydrolysis can be calculated from the mass spectrometric data of the conjugate at the final timepoint by determining the intensity of the peak corresponding to the mass of the original, unhydrolyzed conjugate and the intensity of the peak corresponding to the mass of the hydrolyzed conjugate, and using the sum of the peak intensities to determine the percentage hydrolyzed and percentage unhydrolyzed.

In addition to characterizing the Ligand-Drug Conjugate by its t1/2 of hydrolysis and/or the efficiency of the hydrolysis reaction, the stability of the Ligand-Drug Conjugate can be characterized by the ability of the Ligand-Drug Conjugate to undergo an elimination reaction and for the Drug-Linker to be transferred from the Ligand unit to an alternative reactive thiol present in the milieu of the Ligand-Drug Conjugate. In some embodiments, the Drug-Linker will exhibit no or substantially no disassociation from the Ligand under the following assay and stated conditions. The phrase "substantially no disassociation from the Ligand" is considered to be achieved if less than 40%, preferably less than 20%, even more preferably less than 10%, or even more preferably less than 5% or less than 2% of the Drug-Linker in a sample disassociates from the Ligand.

The elimination of a drug-linker containing an enzyme-cleavable linker from an antibody can be measured in ex vivo plasma by the following method. The conjugate is placed in sterile plasma and incubated at 37° C. At the beginning of the incubation and at varying timepoints from 1 hour to 1 week or longer, an aliquot is removed at frozen at −80° C. Upon completion of the timepoints, the samples are passed over a protein A affinity resin to capture the antibody, the resin is washed with buffer, and then drug is released from the captured antibody by treatment with an appropriate enzyme (e.g. papain or proteinase K for peptide-based cleavable linkers). The released drug can then be quantified by standard LC-MS methodology, and the quantity of drug measured at each timepoint divided by the quantity of drug measured for the pre-incubation aliquot to determine the percentage of drug remaining conjugated to the antibody at each timepoint. The precision of this assay can be improved by including an internal standard antibody-drug conjugate which is prepared using an isotopically labeled version of the same drug-linker, such that the drug which is released from it can be detected independently in the LC-MS assay from the drug released from the test drug-linker by virtue of its mass difference. This isotopically labeled internal standard antibody-drug conjugate is added to each sample in equal amounts immediately prior to the protein A capture step. The quantitation of the drug released from the test ADC is then performed ratiometrically to the signal from the internal standard by conventional LC-MS techniques.

An alternative method for evaluating the elimination of a maleimide drug-linker from an antibody (or other ligand) is to incubate the conjugate in buffer (e.g., phosphate-buffered saline) at slightly elevated pH (e.g., pH 8.0) in the presence of a large excess of a small-molecule thiol (e.g., N-acetyl cysteine, NAC) which will react with any maleimide that eliminates from the parent conjugate. LC-MS assays can be performed to detect and quantify the drug-linker conjugated to NAC, or the parent ligand-conjugate. In the latter case, the ratio of the ligand-conjugate to unconjugated ligand can be measured and will remain constant over time if the ligand-conjugate is stable. Additional methods are provided in the examples section.

Treatment of Cancer

The Ligand-Drug Conjugates are useful for inhibiting the multiplication of a tumor cell or cancer cell, causing apoptosis in a tumor or cancer cell, or for treating cancer in a patient. The Ligand-Drug Conjugates can be used accordingly in a variety of settings for the treatment of cancers. The Ligand-Drug Conjugates can be used to deliver a drug to a tumor cell or cancer cell. Without being bound by theory, in one embodiment, the Ligand unit of a Ligand-Drug Conjugate binds to or associates with a cancer-cell or a tumor-cell-associated antigen, and the Ligand-Drug Conjugate can be taken up (internalized) inside a tumor cell or cancer cell through receptor-mediated endocytosis or other internalization mechanism. The antigen can be attached to a tumor cell or cancer cell or can be an extracellular matrix protein associated with the tumor cell or cancer cell. Once inside the cell, via a cleavable or non-cleavable mechanism, depending upon the components of the linker system, the drug is released within the cell. In an alternative embodiment, the Drug or Drug unit is cleaved from the Ligand-Drug Conjugate outside the tumor cell or cancer cell, and the Drug or Drug unit subsequently penetrates the cell.

The Ligand-Drug Conjugates can provide conjugation-specific tumor or cancer drug targeting, thus reducing general toxicity of the drug. In some embodiments, the Linker units stabilize the Ligand-Drug Conjugates in blood, yet are capable of liberating drug once inside the cell.

In one embodiment, the Ligand unit binds to the tumor cell or cancer cell.

In another embodiment, the Ligand unit binds to a tumor cell or cancer cell antigen which is on the surface of the tumor cell or cancer cell.

In another embodiment, the Ligand unit binds to a tumor cell or cancer cell antigen which is an extracellular matrix protein associated with the tumor cell or cancer cell.

The specificity of the Ligand unit for a particular tumor cell or cancer cell can be important for determining those tumors or cancers that are most effectively treated. For example, a ligand drug conjugate having a BR96Ligand unit can be useful for treating antigen positive carcinomas including those of the lung, breast, colon, ovaries, and pancreas. Ligand-Drug Conjugates having an anti-CD30 or an anti-CD70 binding Ligand unit can be useful for treating hematologic malignancies.

Other particular types of cancers that can be treated with a ligand drug conjugates include, but are not limited to, those disclosed in Table 1:

TABLE 1

Solid tumors, including but not limited to:
fibrosarcoma, myxosarcoma, liposarcoma, chondrosarcoma,
osteogenic sarcoma, chordoma, angiosarcoma, endotheliosarcoma,
lymphangiosarcoma, lymphangioendotheliosarcoma, synovioma,
mesothelioma, Ewing's tumor, leiomyosarcoma, rhabdomyosarcoma,
colon cancer, colorectal cancer, kidney cancer, pancreatic cancer,
bone cancer, breast cancer, ovarian cancer, prostate cancer,
esophogeal cancer, stomach cancer, oral cancer, nasal cancer, throat
cancer, squamous cell carcinoma, basal cell carcinoma,
adenocarcinoma, sweat gland carcinoma, sebaceous gland carcinoma,
papillary carcinoma, papillary adenocarcinomas, cystadenocarcinoma,
medullary carcinoma, bronchogenic carcinoma, renal cell carcinoma,
hepatoma, bile duct carcinoma, choriocarcinoma, seminoma, embryonal
carcinoma, Wilms' tumor, cervical cancer, uterine cancer, testicular
cancer, small cell lung carcinoma, bladder carcinoma, lung cancer,
epithelial carcinoma, glioma, glioblastoma multiforme, astrocytoma,
medulloblastoma, craniopharyngioma, ependymoma, pinealoma,
hemangioblastoma, acoustic neuroma, oligodendroglioma, meningioma,
skin cancer, melanoma, neuroblastoma, retinoblastoma
blood-borne cancers, including but not limited to:
acute lymphoblastic leukemia "ALL", acute lymphoblastic
B-cell leukemia, acute lymphoblastic T-cell leukemia,
acute myeloblastic leukemia "AML", acute promyelocytic
leukemia "APL", acute monoblastic leukemia, acute
erythroleukemic leukemia, acute megakaryoblastic leukemia, acute
myelomonocytic leukemia, acute nonlymphocytic leukemia, acute
undifferentiated leukemia, chronic myelocytic leukemia "CML", chronic
lymphocytic leukemia "CLL", hairy cell leukemia, multiple myeloma
acute and chronic leukemias:
lymphoblastic, myelogenous, lymphocytic, myelocytic leukemias
Lymphomas:
Hodgkin's disease, non-Hodgkin's Lymphoma, Multiple
myeloma, Waldenström's macroglobulinemia,
Heavy chain disease, Polycythemia vera Multi-Modality Therapy for Cancer Cancers, including, but not limited to, a tumor, metastasis, or other disease or disorder characterized by uncontrolled cell growth, can be treated or inhibited by administration of a Ligand-Drug Conjugate.

In other embodiments, methods for treating cancer are provided, including administering to a patient in need thereof an effective amount of a Ligand-Drug Conjugate and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. The Ligand-Drug Conjugates can be administered to a patient that has also undergone surgery as treatment for the cancer.

In some embodiments, the patient also receives an additional treatment, such as radiation therapy. In a specific embodiment, the Ligand-Drug Conjugate is administered concurrently with the chemotherapeutic agent or with radiation therapy. In another specific embodiment, the chemotherapeutic agent or radiation therapy is administered prior or subsequent to administration of a ligand drug conjugate.

A chemotherapeutic agent can be administered over a series of sessions. Any one or a combination of the chemotherapeutic agents, such a standard of care chemotherapeutic agent(s), can be administered.

Additionally, methods of treatment of cancer with a Ligand-Drug Conjugate are provided as an alternative to chemotherapy or radiation therapy where the chemotherapy or the radiation therapy has proven or can prove too toxic, e.g., results in unacceptable or unbearable side effects, for the subject being treated. The patient being treated can, optionally, be treated with another cancer treatment such as surgery, radiation therapy or chemotherapy, depending on which treatment is found to be acceptable or bearable.

Treatment of Autoimmune Diseases

The Ligand-Drug Conjugates are useful for killing or inhibiting the replication of a cell that produces an autoimmune disease or for treating an autoimmune disease. The Ligand-Drug Conjugates can be used accordingly in a variety of settings for the treatment of an autoimmune disease in a patient. The Ligand-Drug Conjugates can be used to deliver a drug to a target cell. Without being bound by theory, in one embodiment, the Ligand-Drug Conjugate associates with an antigen on the surface of a target cell, and the ligand drug conjugate is then taken up inside a target-cell through receptor-mediated endocytosis. Once inside the cell, one or more specific peptide sequences within the Linker unit are cleaved, resulting in release of the Drug or Drug unit. The released Drug or Drug unit is then free to migrate in the cytosol and induce cytotoxic or cytostatic activities. In an alternative embodiment, the Drug is cleaved from the Ligand-Drug Conjugate outside the target cell, and the Drug or Drug unit subsequently penetrates the cell.

In one embodiment, the Ligand unit binds to an autoimmune antigen. In one aspect, the antigen is on the surface of a cell involved in an autoimmune condition.

In another embodiment, the Ligand unit binds to an autoimmune antigen which is on the surface of a cell.

In one embodiment, the Ligand unit binds to activated lymphocytes that are associated with the autoimmune disease state.

In a further embodiment, the Ligand-Drug Conjugate kills or inhibit the multiplication of cells that produce an autoimmune antibody associated with a particular autoimmune disease.

Particular types of autoimmune diseases that can be treated with the ligand drug conjugates include, but are not limited to, Th2 lymphocyte related disorders (e.g., atopic dermatitis, atopic asthma, rhinoconjunctivitis, allergic rhinitis, Omenn's syndrome, systemic sclerosis, and graft versus host disease); Th1 lymphocyte-related disorders (e.g., rheumatoid arthritis, multiple sclerosis, psoriasis, Sjorgren's syndrome, Hashimoto's thyroiditis, Grave's disease, primary biliary cirrhosis, Wegener's granulomatosis, and tuberculosis); activated B lymphocyte-related disorders (e.g., systemic lupus erythematosus, Goodpasture's syndrome, rheumatoid arthritis, and type I diabetes); and those disclosed in Table 2.

TABLE 2

Active Chronic Hepatitis, Addison's Disease, Allergic Alveolitis, Allergic Reaction, Allergic Rhinitis, Alport's Syndrome, Anaphlaxis, Ankylosing Spondylitis, Anti-phosholipid Syndrome, Arthritis, Ascariasis, Aspergillosis, Atopic Allergy, Atropic Dermatitis, Atropic Rhinitis, Behcet's Disease, Bird-Fancier's Lung, Bronchial Asthma,
Caplan's Syndrome, Cardiomyopathy, Celiac Disease, Chagas' Disease, Chronic Glomerulonephritis, Cogan's Syndrome, Cold Agglutinin Disease, Congenital Rubella Infection, CREST Syndrome, Crohn's Disease, Cryoglobulinemia, Cushing's Syndrome, Dermatomyositis, Discoid Lupus, Dressler's Syndrome, Eaton-Lambert Syndrome, Echovirus Infection, Encephalomyelitis, Endocrine opthalmopathy, Epstein-Barr Virus Infection, Equine Heaves, Erythematosis, Evan's Syndrome, Felty's Syndrome, Fibromyalgia, Fuch's Cyclitis, Gastric Atrophy, Gastrointestinal Allergy, Giant Cell Arteritis, Glomerulonephritis, Goodpasture's Syndrome, Graft v. Host Disease, Graves' Disease, Guillain-Barre Disease, Hashimoto's Thyroiditis, Hemolytic Anemia, Henoch-Schonlein Purpura, Idiopathic Adrenal Atrophy, Idiopathic Pulmonary Fibritis, IgA Nephropathy, Inflammatory Bowel Diseases, Insulin-dependent Diabetes Mellitus, Juvenile Arthritis, Juvenile Diabetes Mellitus (Type I), Lambert-Eaton Syndrome, Laminitis, Lichen Planus, Lupoid Hepatitis, Lupus, Lymphopenia, Meniere's Disease, Mixed Connective Tissue Disease, Multiple Sclerosis, Myasthenia Gravis, Pernicious Anemia, Polyglandular Syndromes, Presenile Dementia, Primary Agammaglobulinemia, Primary Biliary Cirrhosis, Psoriasis, Psoriatic Arthritis, Raynauds Phenomenon, Recurrent Abortion, Reiter's Syndrome, Rheumatic Fever, Rheumatoid Arthritis, Sampter's Syndrome, Schistosomiasis, Schmidt's Syndrome, Scleroderma, Shulman's Syndrome, Sjorgen's Syndrome, Stiff-Man Syndrome, Sympathetic Ophthalmia, Systemic Lupus Erythematosis, Takayasu's Arteritis, Temporal Arteritis, Thyroiditis, Thrombocytopenia, Thyrotoxicosis, Toxic Epidermal Necrolysis, Type B Insulin Resistance, Type I Diabetes Mellitus, Ulcerative Colitis, Uveitis, Vitiligo, Waldenstrom's Macroglobulemia, Wegener's Granulomatosis Multi-Drug Therapy of Autoimmune Diseases Methods for treating an autoimmune disease are also disclosed including administering to a patient in need thereof an effective amount of a Ligand-Drug Conjugate and another therapeutic agent known for the treatment of an autoimmune disease.

Treatment of Infectious Diseases

The Ligand-Drug Conjugates are useful for killing or inhibiting the multiplication of a cell that produces an infectious disease or for treating an infectious disease. The Ligand-Drug Conjugates can be used accordingly in a variety of settings for the treatment of an infectious disease in a patient. The Ligand-Drug Conjugates can be used to deliver a drug to a target cell. In one embodiment, the Ligand unit binds to the infectious disease cell.

In one embodiment, the conjugates kill or inhibit the multiplication of cells that produce a particular infectious disease.

Particular types of infectious diseases that can be treated with the Ligand-Drug Conjugates include, but are not limited to, those disclosed in Table 3.

TABLE 3

Bacterial Diseases:
Diphtheria, Pertussis, Occult Bacteremia, Urinary Tract Infection, Gastroenteritis, Cellulitis, Epiglottitis, Tracheitis, Adenoid Hypertrophy, Retropharyngeal Abcess, Impetigo, Ecthyma, Pneumonia, Endocarditis, Septic Arthritis, Pneumococca, Peritonitis, Bactermia, Meningitis, Acute Purulent Meningitis, Urethritis, Cervicitis, Proctitis, Pharyngitis, Salpingitis, Epididymitis, Gonorrhea, Syphilis, Listeriosis, Anthrax, Nocardiosis, Salmonella, Typhoid Fever, Dysentery, Conjunctivitis, Sinusitis, Brucellosis, Tullaremia, Cholera, Bubonic Plague, Tetanus, Necrotizing Enteritis, Actinomycosis, Mixed Anaerobic Infections, Syphilis, Relapsing Fever, Leptospirosis, Lyme Disease,

TABLE 3-continued

Rat Bite Fever, Tuberculosis, Lymphadenitis, Leprosy, Chlamydia, Chlamydial Pneumonia, Trachoma, Inclusion Conjunctivitis
Systemic Fungal Diseases:
Histoplamosis, Coccidiodomycosis, Blastomycosis, Sporotrichosis, Cryptococcsis, Systemic Candidiasis, Aspergillosis, Mucormycosis, Mycetoma, Chromomycosis
Rickettsial Diseases:
Typhus, Rocky Mountain Spotted Fever, Ehrlichiosis, Eastern Tick-Borne Rickettsioses, Rickettsialpox, Q Fever, Bartonellosis
Parasitic Diseases:
Malaria, Babesiosis, African Sleeping Sickness, Chagas' Disease, Leishmaniasis, Dum-Dum Fever, Toxoplasmosis, Meningoencephalitis, Keratitis, Entamebiasis, Giardiasis, Cryptosporidiasis, Isosporiasis, Cyclosporiasis, Microsporidiosis, Ascariasis, Whipworm Infection, Hookworm Infection, Threadworm Infection, Ocular Larva Migrans, Trichinosis, Guinea Worm Disease, Lymphatic Filariasis, Loiasis, River Blindness, Canine Heartworm Infection, Schistosomiasis, Swimmer's Itch, Oriental Lung Fluke, Oriental Liver Fluke, Fascioliasis, Fasciolopsiasis, Opisthorchiasis, Tapeworm Infections, Hydatid Disease, Alveolar Hydatid Disease
Viral Diseases:
Measles, Subacute sclerosing panencephalitis, Common Cold, Mumps, Rubella, Roseola, Fifth Disease, Chickenpox, Respiratory syncytial virus infection, Croup, Bronchiolitis, Infectious Mononucleosis, Poliomyelitis, Herpangina, Hand-Foot-and-Mouth Disease, Bornholm Disease, Genital Herpes, Genital Warts, Aseptic Meningitis, Myocarditis, Pericarditis, Gastroenteritis, Acquired Immunodeficiency Syndrome (AIDS), Human Immunodeficiency Virus (HIV), Reye's Syndrome, Kawasaki Syndrome, Influenza, Bronchitis, Viral "Walking" Pneumonia, Acute Febrile Respiratory Disease, Acute pharyngoconjunctival fever, Epidemic keratoconjunctivitis, Herpes Simplex Virus 1 (HSV-1), Herpes Simplex Virus 2 (HSV-2), Shingles, Cytomegalic Inclusion Disease, Rabies, Progressive Multifocal Leukoencephalopathy, Kuru, Fatal Familial Insomnia, Creutzfeldt-Jakob Disease, Gerstmann-Straussler-Scheinker Disease, Tropical Spastic Paraparesis, Western Equine Encephalitis, California Encephalitis, St. Louis Encephalitis, Yellow Fever, Dengue, Lymphocytic choriomeningitis, Lassa Fever, Hemorrhagic Fever, Hantvirus Pulmonary Syndrome, Marburg Virus Infections, Ebola Virus Infections, Smallpox Multi-Drug Therapy of Infectious Diseases Methods for treating an infectious disease are disclosed including administering to a patient in need thereof a Ligand-Drug Conjugate and another therapeutic agent that is an anti-infectious disease agent.

Compositions and Methods of Administration

The present invention provides pharmaceutical compositions comprising the Ligand-Drug Conjugates described herein and a pharmaceutically acceptable carrier. The Ligand-Drug Conjugates can be in any form that allows for the compound to be administered to a patient for treatment of a disorder associated with expression of the antigen to which the Ligand unit binds. For example, the conjugates can be in the form of a liquid or solid. The preferred route of administration is parenteral. Parenteral administration includes subcutaneous injections, intravenous, intramuscular, intrasternal injection or infusion techniques. In one aspect, the compositions are administered parenterally. In one aspect, the compounds are administered intravenously.

The present invention also provides pharmaceutical compositions comprising the Ligand-Functional Agent Conjugates described herein and a pharmaceutically acceptable carrier. The Ligand-Drug Conjugates can be in any form that allows for the compound to be administered to a patient for treatment of a disorder or for diagnostic purposes Pharmaceutical compositions can be formulated so as to allow a compound to be bioavailable upon administration of the composition to a patient. Compositions can take the form of one or more dosage units, where for example, a tablet can be a single dosage unit.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the compound, the manner of administration, and the composition employed.

The composition can be, for example, in the form of a liquid. The liquid can be useful for delivery by injection. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as amino acids, acetates, citrates or phosphates; detergents, such as nonionic surfactants, polyols; and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of the conjugate that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a compound such that a suitable dosage will be obtained. Typically, this amount is at least about 0.01% of a compound by weight of the composition.

For intravenous administration, the composition can comprise from about 0.01 to about 100 mg of a Ligand-Drug Conjugate per kg of the animal's body weight. In one aspect, the composition can include from about 1 to about 100 mg of a Ligand-Drug Conjugate per kg of the animal's body weight. In another aspect, the amount administered will be in the range from about 0.1 to about 25 mg/kg of body weight of a compound.

Generally, the dosage of a compound administered to a patient is typically about 0.01 mg/kg to about 100 mg/kg of the subject's body weight. In some embodiments, the dosage administered to a patient is between about 0.01 mg/kg to about 15 mg/kg of the subject's body weight. In some embodiments, the dosage administered to a patient is between about 0.1 mg/kg and about 15 mg/kg of the subject's body weight. In some embodiments, the dosage administered to a patient is between about 0.1 mg/kg and about 20 mg/kg of the subject's body weight. In some embodiments, the dosage administered is between about 0.1 mg/kg to about 5 mg/kg or about 0.1 mg/kg to about 10 mg/kg of the subject's body weight. In some embodiments, the dosage administered is between about 1 mg/kg to about 15 mg/kg of the subject's body weight. In some embodiments, the dosage administered is between about 1 mg/kg to about 10 mg/kg of the subject's body weight. In some embodiments, the dosage administered is between about 0.1 to 4 mg/kg, even more preferably 0.1 to 3.2 mg/kg, or even more preferably 0.1 to 2.7 mg/kg of the subject's body weight over a treatment cycle.

The Ligand-Functional Agent Conjugates e.g., Ligand-Drug Conjugates) can be administered by any convenient route, for example by infusion or bolus injection, by absorption through epithelial or mucocutaneous linings (e.g., oral mucosa, rectal and intestinal mucosa). Administration can be systemic or local. Various delivery systems are known, e.g., encapsulation in liposomes, microparticles, microcapsules, capsules, and can be used to administer a compound. In certain embodiments, more than one compounds or composition is administered to a patient.

The term "carrier" refers to a diluent, adjuvant or excipient, with which a compound is administered. Such pharmaceutical carriers can be liquids, such as water and oils, including those of petroleum, animal, vegetable or synthetic origin, such as peanut oil, soybean oil, mineral oil, sesame oil. The carriers can be saline, gum acacia, gelatin, starch paste, talc, keratin, colloidal silica, urea. In addition, auxiliary, stabilizing, thickening, lubricating and coloring agents can be used. In one embodiment, when administered to a patient, the compound or compositions and pharmaceutically acceptable carriers are sterile. Water is an exemplary carrier when the compounds are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol. The present compositions, if desired, can also contain minor amounts of wetting or emulsifying agents, or pH buffering agents.

In an embodiment, the conjugates are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a conjugate is to be administered by infusion, it can be dispensed, for example, with an infusion bottle containing sterile pharmaceutical grade water or saline. Where the conjugate is administered by injection, an ampoule of sterile water for injection or saline can be provided so that the ingredients can be mixed prior to administration.

The pharmaceutical compositions are generally formulated as sterile, substantially isotonic and in full compliance with all Good Manufacturing Practice (GMP) regulations of the U.S. Food and Drug Administration.

Pharmaceutical compositions of the present invention comprise the Ligand Drug Conjugates of the present invention and a pharmaceutically acceptable carrier. In some preferred embodiments, all, or substantially all, or more than 50% of the Ligand Drug Conjugates present in the pharmaceutical composition comprises a hydrolyzed thio-substituted succinimide. In some preferred embodiments, more than 55%, 60%, 65%, 70%, 75%, 80%, 85%, 90%, 91%, 92%, 93%, 94%, 95%, 96%, 97%, 98%, or 99% of the Ligand Drug Conjugates present in the pharmaceutical composition comprises a hydrolyzed thio-substituted succinimide.

Methods for Preparing Ligand-Drug Conjugates

In another aspect, the present invention provides methods of preparing Ligand-Drug Conjugates or Ligand-Functional Agent Conjugates comprising a Self-Stabilizing Linker.

In some embodiments, methods of the present invention comprise the steps of providing a Drug-Linker or Linker unit as described herein, conjugating said Drug-Linker or Linker unit to a sulfhydryl group of a Ligand unit to form a conjugate, allowing the resultant conjugate to undergo a hydrolysis reaction to form a Ligand-Drug conjugate comprising a thio-substituted hydrolyzed succinimide.

The rate of the thio-substituted succinimide hydrolysis can be manipulated by adjusting the reaction conditions following conjugation of the Drug-Linker to the Ligand, e.g., by adjusting the pH or temperature. In some embodiments of the present invention, all, substantially all, or at least 50%, 60%, 70%, 80%, 85%, 90% or even 95% of the thio-substituted succinimide is hydrolyzed without manipulation of the reaction conditions, i.e., the hydrolysis reaction occurs under the same reaction conditions as the conjugation reaction. In some embodiments, all, substantially all, or at least 50%, 60%, 70%, 80%, 85%, 90% or even 95% of the thio-substituted succinimide is hydrolyzed from 20 minutes, to 4 hours following conjugation, preferably from 20 minutes to 2 hours following conjugation. In exemplary embodiments, the conjugation conditions are pH of about 7.4 and a temperature of about 22° C.

In some embodiments, methods for preparing a Ligand-Drug Conjugate comprises the steps of providing a Drug-Linker or Linker unit comprising a Self-Stabilizing Linker; conjugating said Drug-Linker or Linker unit to a sulfhydryl group of a Ligand to form a Ligand-Drug Conjugate conjugate comprising a non-hydrolyzed thio-substituted succinimide; allowing the non-hydrolyzed thio-substituted succinimide to undergo a hydrolysis reaction, wherein all, substantially all, or at least 50%, 60%, 70%, 80% or even 85% of the succinimide is hydrolyzed from 10 minutes to 4 hours following conjugation. In some embodiments, all, substantially all, or at least 50%, 60%, 70%, 80%, 85%, 90% or even 95% of the succinimide is hydrolyzed by 10 minutes, by 20 minutes, 40 minutes 60 minutes, 90 minutes or 120 minutes following conjugation. In some embodiments, the hydrolysis reaction occurs under the same reaction conditions as the conjugation reaction. In exemplary embodiments, the conjugation conditions are pH of about 7.4 and a temperature of about 22° C.

Methods for Synthesizing Self-Stabilizing Linkers

The present invention provides, inter alia, Self-Stabilizing Linkers. Methods of preparing Self-Stabilizing Linker units are encompassed within the scope of the present invention.

Maleimide compounds are typically prepared from corresponding amines by reaction of the primary amine with maleic anhydride followed by cyclodehydration of the maleamic acid. The overall scheme for the preparation of maleimde compounds is shown in the scheme below.

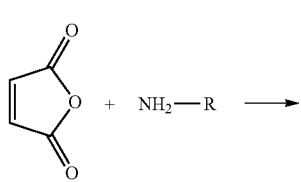

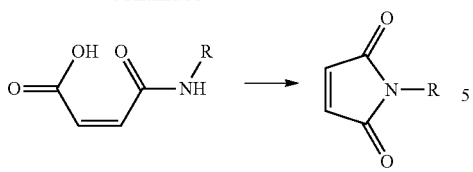 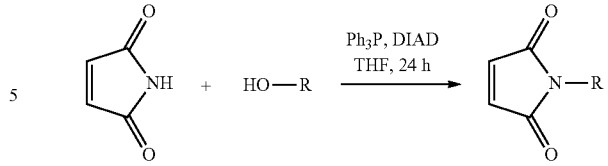

For preparation of maleimides containing basic groups in the side chain of the starting amine, such basic groups should be protected, if necessary. The appropriate protecting groups should be stable under conditions of maleimide preparation, yet should be removable later in the presence of maleimide. Suitable protecting groups consist, but are not limited to, acid labile protecting groups. "Boc" protecting group is one of the preferred protecting group.

The first step of maleimide preparation, the formation of the maleamic acid is very facile and can be usually accomplished in good yield by slow addition of the amine to a suspension containing a stoichiometric excess of the maleic anhydride.

The second step, cyclodehydration of the maleamic acid, can be accomplished in a number of ways known to skilled in the art. For example, the use of chemical dehydrating agents has been a well established method for accomplishing this step. Carbodiimides in combination with isomerizing alcohols, for example: DCC/HOBt, have been used to effect cyclodehydration of amic acids to maleimides.

Thermal cyclodehydration with use of azeotropic distillation in the presence of acid catalyst is another well known method to generate maleimides. The use of an azeotropic solvent permits the efficient removal of the water co-product as it forms, thereby driving reaction to maleimide. Suitable azeotropic solvents include cyclohexane, benzene, toluene, ethylbensene, mesitylene, and the like. Toluene is considered to be the most desirable since it boils at 110° C. at atmospheric pressure. Boiling temperatures below 200° C. are preferable to minimize possible thermal isomerization of maleamic acid to the more thermodynamically stable trans (fumaramic acid) structure.

The use of polar aprotic co-solvents can be beneficial for overall yield improvement as well as reducing time of cyclodehydration. Several polar aprotic solvents including dimethylformamide, dimethylacetamide, acetonitrile, N-methylpyrrolidone, dimethylsulfoxide, and sulfonate have been claimed to be useful. The most useful polar aprotic solvent is dimethylformamide.

Incorporation of certain amine salts instead of aprotic solvents can be further beneficial for maleimide formation according to U.S. Pat. No. 5,973,166.

One step microwave assisted maleimide synthesis has been also reported starting from maleic anhydride and an appropriate amine using no solvent (H. N. Borah, et al., J. Chem. Research (S), 1998, 272-272).

Example using water as a solvent for maleimide formation has been reported in ARKIVOC, 2001 (v) 60-67 by V. Ondrus, et al. Alternatively, maleimide compounds can be generated from maleimide and appropriate alcohol using, for example, Mitsunobu reaction conditions as shown in the scheme below (M.A. Walker, *Tetrahedron Letters*, 1994, v. 35, n 5, pp. 665-668).

The self-stabilizing linker assembly of the present invention are linked to the Stretcher unit, Cleavable unit, Spacer unit, or Drug unit using the teachings described herein in combination with methods known in the art. The Linkers and Drug-Linkers are conjugated to Ligand units using teachings described herein in combination with methods known in the art. For example, for conjugation to interchain disulfides, an antibody can be treated with a reducing agent, such as dithiothreitol (DTT) to reduce some or all of the interchain disulfide cysteine residues to form highly nucleophilic cysteine thiol groups. The full reduced antibody or partially reduced antibody can be subsequently conjugated to the maleimide of the Linker Unit. In exemplary embodiments, conjugation conditions are gentle ones, pH of about 7 and a temperature of about 22° C.

Intermediates

The present invention provides intermediates for use in making Self-Stabilizing Linkers. Intermediates include the following wherein T, c, $R^{11}$ and $R^{12}$ are as previously described.

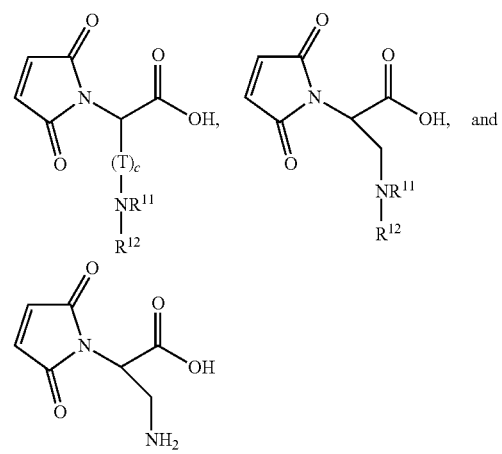

Mono-thio-substituted or Di-thio-substituted Maleimide or Succinimide Self-Stabilizing Linkers In addition to designing self-stabilizing linkers for increasing the hydrolysis rates of mono thio-substituted succinimides, self-stabilizing linkers can also be used to increase the hydrolysis rate of mono-thio-substituted maleimides, di-thio-substituted maleimides, or di-thio-substituted succinimides.

In view of the above, the present invention provides in one group of embodiments, a Ligand-Functional Agent Conjugate comprising a Ligand unit and at least one Functional Agent selected from a Drug unit, a Detection Unit, or a Stabilizing Unit, wherein the Ligand unit and each of the Functional Agent(s) are joined by a self-stabilizing linker assembly comprising a succinimide ring, a maleimide ring, a hydrolyzed succinimide ring or a hydrolyzed maleimide ring wherein the succinimide ring, maleimide ring, hydrolyzed succinimide ring or hydrolyzed maleimide ring is directly conjugated to the Ligand unit via one or two thioether linkages; and a base and an electron withdrawing group operably linked to stabilize the conjugate in plasma relative to a Ligand-Functional Agent Conjugate lacking the self-stabilizing linker assembly (i.e. by increasing the rate of succinimide or maleimide ring hydrolysis). In some aspects, the electron withdrawing group is positioned to increase the electrophilicity of the succinimide or maleimide rendering it more reactive with water and the base is positioned to assist the hydrolysis of the succinimide or maleimide ring (e.g., by an intramolecular base catalysis mechanism).

In some embodiments, the Ligand-Functional Agent Conjugates are represented by Formula IV or IVa:

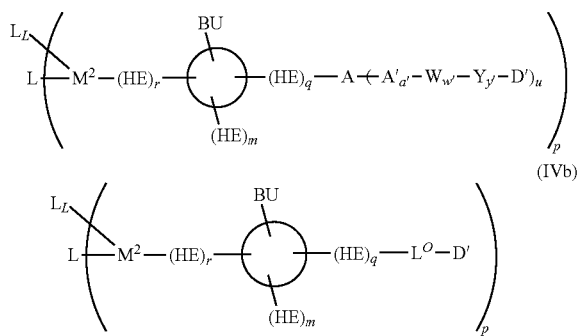

or a salt thereof (e.g., pharmaceutically acceptable salt thereof);
wherein
L is a Ligand unit
$L_L$ is a Ligand unit that can be present or absent, wherein L and $L_L$ can be the same or different Ligand units;
D' is a Drug unit, a Detection unit, or a Stabilizing unit;
$L^O$ is an optional secondary linker assembly;
$M^2$ is a maleimide ring, a hydrolyzed maleimide, a succinimide ring, or a hydrolyzed succinimide conjugated to at least one of L or $L_L$ via a thioether linkage; and
BU is a Basic unit;
HE is a hydrolysis enhancer comprising an electron withdrawing group;
The circle represents a scaffold that can be $C_{1-8}$ alkylene, $C_{1-8}$ heteroalkylene, $C_{6-10}$ arylene, or $C_{4-10}$ heteroarylene, and optionally comprises a reactive site suitable for attachment to $L^O$, A, W, Y or D';
the subscripts m, q and r are each 0 or 1, and the sum of m+q+r is 0, 1 or 2 provided that if m+q+r is 0, the scaffold is a $C_{6-10}$ arylene or $C_{4-10}$ heteroarylene;
the subscript p ranges from 1 to 20.
  W— is an optional Cleavable unit,
  the subscript w' is 0 or 1;
  —Y— is an optional Spacer unit,
  the subscript y' is 0 or 1,
  A is an optional Stretcher unit,
  A' is an optional Stretcher unit component at the terminus of A;
  a' is 0 or 1; and
  u is from 1 to 20, with the proviso that when u is from 2 to 20, A is present and when u is 1, A can be present or absent.

L, HE and BU, $L^O$, A, W, and Y have the meanings provided for the Ligand-Drug Conjugates. Additionally each of the specifically recited selected embodiments for the circle, L, HE, BU, $L^O$, A, W, and Y are equally applicable to these Conjugates. L and $L_L$ can be different Ligand units or the same Ligand unit. In embodiments, wherein L and $L_L$ are the same Ligand unit, the succinimide or maleimide can be conjugated to the Ligand unit on the same or different polypeptide chains of the Ligand unit.

In some aspects, when r is 1, HE does not comprise a carbonyl group, (i.e., C(=O))

In some aspects, m+q+r is 0, 1 or 2

In some aspects, r is zero.

In some aspects, the Ligand-Functional Agent Conjugate is represented by Formula IV or IVa or a salt thereof wherein r and m are zero and q is one.

In some aspects, the Ligand-Functional Agent Conjugate is represented by Formula IV or IVa or a salt thereof wherein the circle represents a scaffold that is $C_{1-8}$ alkylene or $C_{1-8}$ heteroalkylene (preferably $C_{1-4}$ alkylene or $C_{1-4}$ heteroalkylene), r is zero, and the sum of m+q is 1. In some such aspects, the scaffold is $C_{1-3}$ alkylene or $C_{1-3}$ heteroalkylene. In some such aspects, the alkylene is straight chain or branched.

In some aspects, the Ligand-Functional Agent Conjugate is represented by Formula IV or IVa or a salt thereof wherein the circle represents a scaffold that is $C_{1-8}$ alkylene or $C_{1-8}$ heteroalkylene (preferably $C_{1-4}$ alkylene or $C_{1-4}$ heteroalkylene), and m and r are zero. In some such aspects, the scaffold is $C_{1-3}$ alkylene or $C_{1-3}$ heteroalkylene. In some such aspects, the alkylene is straight chain or branched.

In some aspects, the Ligand-Functional Agent Conjugate is represented by Formula IV or IVa or a salt thereof wherein the circle represents a scaffold that is $C_1$, $C_2$, $C_3$ or $C_4$ straight or branched chain alkylene, r is zero, and the sum of m+q is 1.

In some aspects, the Ligand-Functional Agent Conjugate is represented by Formula IV or IVa or a salt thereof wherein the circle represents a scaffold that is $C_1$, $C_2$, $C_3$ or $C_4$ straight or branched chain alkylene, and m and r are zero.

In some aspects, m and r are zero and

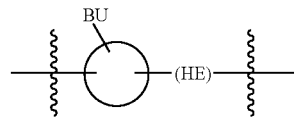

is represented by:

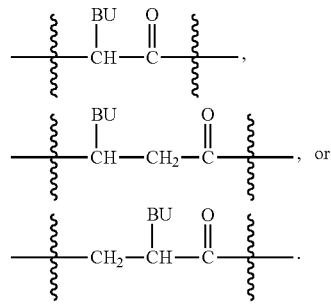

In some aspects, there are no less than 2 and no more than 6 intervening atoms between the base of the Basic unit and the nitrogen atom of the maleimide or succinimide (hydrolyzed or non-hydrolyzed) and there are no more than 5 atoms, no more than 4 atoms, no more than 3 atoms, or no more than 2 intervening atoms between the electron withdrawing group and the nitrogen atom of the maleimide or succinimide (hydrolyzed or non-hydrolyzed).

In some aspects, $M^2$ is a succinimide ring or hydrolyzed succinimide and $L_L$ is present. In some aspects, $M^2$ is a succinimide ring or hydrolyzed succinimide and $L_L$ is absent. In some aspects, $M^2$ is a maleimide ring or hydrolyzed maleimide and $L_L$ is present. In some aspects, $M^2$ is a maleimide ring or hydrolyzed maleimide and $L_L$ is absent. In each of these embodiments when L and $L_L$ are present, L and $L_L$ can be the same Ligand unit or different Ligand units. In some aspects wherein L and $L_L$ are present and are the same Ligand unit, the maleimide or succinimide can be conjugated to the Ligand unit on the same or different polypeptide chains of the Ligand unit.

In each of these embodiments, the alkylene or heteroalkylene chain can be straight or branched. In some aspects, the alkylene or heteroalkylene chain will be a straight chain. In other aspects, it will be branched.

In each of these embodiments, p can range from 1 to 20, preferably 1 to 12, even more 1 to 10 or 1 to 8.

In some aspects wherein the scaffold itself is directly linked to the optional secondary linker assembly or D', (for example, in select embodiments when q is zero or when q is zero and r is zero), the scaffold will comprise a reactive site suitable for attachment to the optional secondary linker assembly or D'

In some aspects wherein the scaffold itself is directly linked to the optional secondary linker assembly or D', (for example, in select embodiments when q is zero or when q is zero and r is zero), the scaffold will comprise a reactive site suitable for attachment to A or D'.

The maleimide ring can be conjugated to the Ligand unit via one or two thioether linkages as illustrated below both in non-hydrolyzed and hydrolyzed form and the succinimide ring can be conjugated to the Ligand unit via two thioether linkages as illustrated below in both non-hydrolyzed and hydrolyzed form wherein the wavy line indicates the point of attachment to the remainder of the linker conjugate or linker-functional agent conjugate:

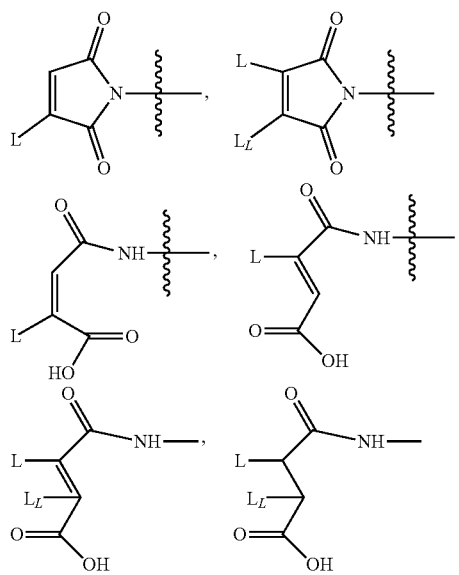

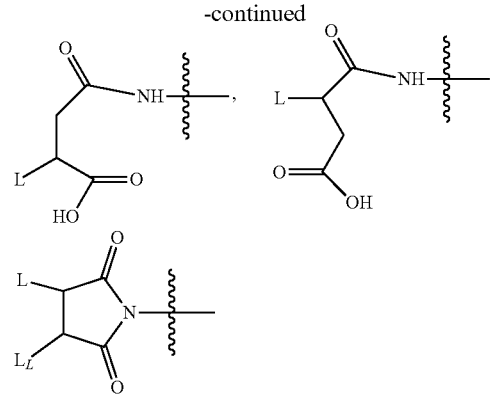

In embodiments wherein the maleimide ring, hydrolyzed maleimide, succinimide ring, or hydrolyzed succinimide is conjugated to the Ligand via two thioether linkages, p typically ranges from 1 to 10, or 1 to 8, or 1 to 4 and the maleimide or succinimide can be conjugated to the same or different polypeptide chains of the Ligand. In some aspects, the Ligand is an antibody. In other aspects, the Ligand is a non-antibody protein.

Functional Agent-Linker Conjugates having either branched or non-branched linkers can be represented by the following formulas:

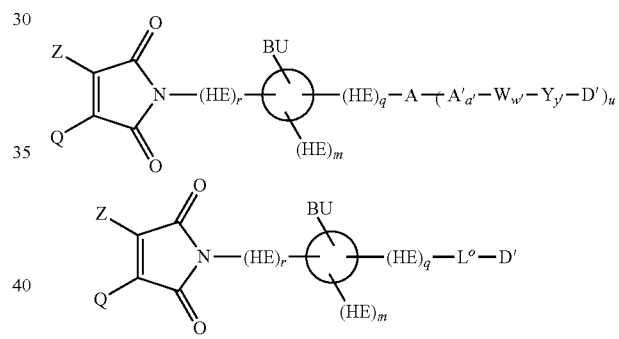

or a salt thereof (e.g., pharmaceutically acceptable salt thereof);

wherein

D' is a Drug unit, a Detection unit, or a Stabilizing unit;

$L^O$ is an optional secondary linker assembly;

Q and Z are hydrogen or halogen wherein at least one of Q and Z are halogen;

BU is a Basic unit;

HE is a hydrolysis enhancer comprising an electron withdrawing group; the circle represents a scaffold that can be $C_{1-8}$ alkylene, $C_{1-8}$ heteroalkylene, $C_{6-10}$ arylene, or $C_{4-10}$ heteroarylene, and optionally comprises a reactive site suitable for attachment to $L^O$, A, W, Y or D';

the subscripts m, q and r are each 0 or 1, and the sum of m+q+r is 0, 1 or 2 provided that if m+q+r is 0, the scaffold is a $C_{6-10}$ arylene or $C_{4-10}$ heteroarylene;

W— is an optional Cleavable unit, the subscript w' is 0 or 1;

—Y— is an optional Spacer unit, the subscript y' is 0 or 1,

A is an optional Stretcher unit,

A' is an optional Stretcher unit component at the terminus of A;

a' is 0 or 1; and
u is from 1 to 20, with the proviso that when u is from 2 to 20, A is present and when u is 1, A can be present or absent In some aspects, the halogen is bromine.

HE and BU, $L^O$, A, W, and Y have the meanings provided for the Drug-Linker Conjugates. Additionally each of the specifically recited selected embodiments for the circle, HE, BU, $L^O$, A, W, and Y are equally applicable to these Conjugates.

In some aspects, m and r are zero and

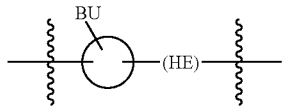

is represented by:

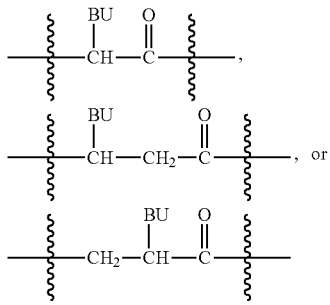

Ligand-Linker Conjugates having either branched or non-branched linkers can be represented by the following formulas:

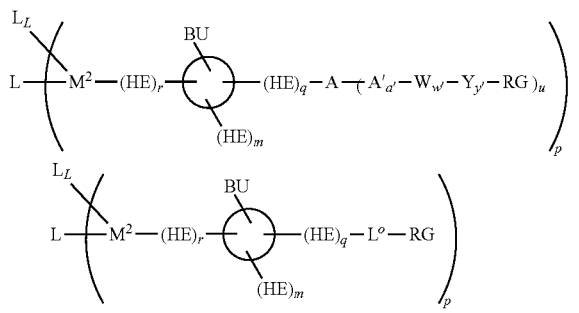

or a salt thereof (e.g., pharmaceutically acceptable salt thereof);
wherein
L is a Ligand unit;
$L_L$ is a Ligand unit that can be present or absent, wherein L and $L_L$ can be the same or different Ligand units;
RG is a reactive group (comprising a reactive site) at the terminus of $L^O$ or

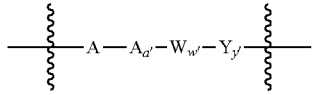

which is suitable for attaching a Drug unit, Detection unit or Stabilizing unit;
$L^O$ is an optional secondary linker assembly that is present;
$M^2$ is a maleimide ring, a hydrolyzed maleimide, a succinimide ring, or a hydrolyzed succinimide conjugated to at least one of L or $L_L$ via a thioether linkage; and BU is a Basic unit;
HE is a hydrolysis enhancer comprising an electron withdrawing group;
the circle represents a scaffold that can be $C_{1-8}$ alkylene, $C_{1-8}$ heteroalkylene, $C_{6-10}$ arylene, or $C_{4-10}$ heteroarylene, and optionally comprises a reactive site suitable for attachment to $L^O$, A, W, Y or FA;
the subscripts m, q and r are each 0 or 1, and the sum of m+q+r is 0, 1 or 2 provided that if m+q+r is 0, the scaffold is a $C_{6-10}$ arylene or $C_{4-10}$ heteroarylene;
the subscript p ranges from 1 to 20.
W— is an optional Cleavable unit,
the subscript w' is 0 or 1;
—Y— is an optional Spacer unit,
the subscript y' is 0 or 1,
A is an optional Stretcher unit,
A' is an optional Stretcher unit component at the terminus of A;
a' is 0 or 1; and
u is from 1 to 20, with the proviso that when u is from 2 to 20, A is present and when u is 1, A can be present or absent.

L, HE and BU, $L^O$, A, W, and Y have the meanings provided for the Ligand-Drug Conjugates. Additionally each of the specifically recited selected embodiments for the circle, L, HE, BU, $L^O$, A, W, and Y are equally applicable to these Conjugates.

In some aspects, r and m are zero and

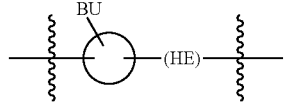

is represented by:

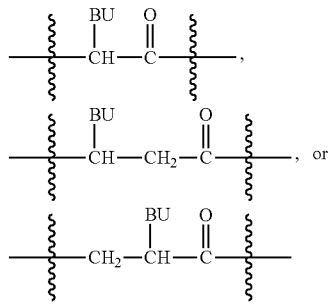

Branched or non-branched Linkers can be represented by the following formulas:

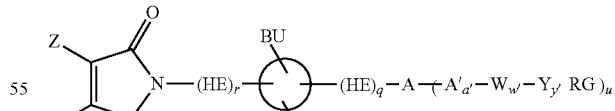
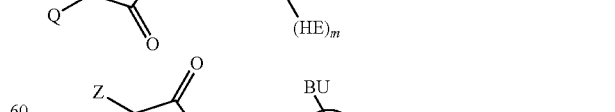

or a salt thereof (e.g., pharmaceutically acceptable salt thereof);

wherein

RG is a reactive group (comprising a reactive site) at the terminus of $L^O$ or

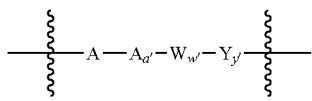

which is suitable for attaching a Drug unit, Detection unit or Stability unit;

$L^O$ is an optional secondary linker assembly that is present;

Q and Z are hydrogen or halogen wherein at least one of Q and Z are halogen;

BU is a Basic unit;

HE is a hydrolysis enhancer comprising an electron withdrawing group;

the circle represents a scaffold that can be $C_{1-8}$ alkylene, $C_{1-8}$ heteroalkylene, $C_{6-10}$ arylene, or $C_{4-10}$ heteroarylene, and optionally comprises a reactive site suitable for attachment to $L^O$, A, W, Y or FA;

the subscripts m, q and r are each 0 or 1, and the sum of m+q+r is 0, 1 or 2 provided that if m+q+r is 0, the scaffold is a $C_{6-10}$ arylene or $C_{4-10}$ heteroarylene;

W— is an optional Cleavable unit, the subscript w' is 0 or 1;

—Y— is an optional Spacer unit, the subscript y' is 0 or 1,

A is an optional Stretcher unit,

A' is an optional Stretcher unit component at the terminus of A;

a' is 0 or 1; and u is from 1 to 20, with the proviso that when u is from 2 to 20, A is present and when u is 1, A can be present or absent.

HE and BU, $L^O$, A, W, and Y have the meanings provided for the Ligand-Drug Conjugates. Additionally each of the specifically recited selected embodiments for the circle, HE, BU, $L^O$, A, W, and Y are equally applicable to these Conjugates.

In some aspects, r and m are zero and

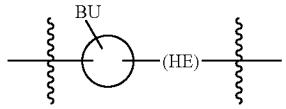

is represented by:

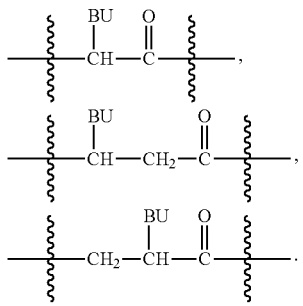

Methods of preparing mono- or di-thio-substituted halomaleimides as well as di-thiosubstituted succinimides are known in the art as are methods of conjugating them to ligands, see for example, Ryan et al., Chem. Coomun., 2011, 47, 5452-5454 and Smith et al., J. Am. Chem. Soc. 2010, 132(6), 1960-1965.

EXAMPLES

Example 1

Synthesis of Representative Self-Stabilizing Components

Chemical Formula: $C_{11}H_{22}N_2O_4$
Molecular Weight: 246.30

Chemical Formula: $C_{15}H_{24}N_2O_7$
Molecular Weight: 344.36
Maleyl-Lysine(boc)OH In a 50 ml round bottom flask H-Lys(boc)-OH (246 mg, 1 mmol) and maleic anhydride (98 mg, 1 mmol) were dissolved in 1 ml (4 vol.) acetic acid and the solution was stirred at room temperature for 3 hours. The reaction mixture was concentrated to an oil on the rotovap, and the product was precipitated by adding ~10 ml dichloromethane. The precipitate was collected by vacuum filtration, washed with dichloromethane, and dried overnight in the vacuum oven. 270 mg of product was recovered as a white powder (85% yield)

Chemical Formula: $C_{15}H_{24}N_2O_7$
Molecular Weight: 344.36

Chemical Formula: $C_{15}H_{22}N_2O_6$
Molecular Weight: 326.34
Maleoyl-Lysine(boc)-OH Maleyl-Lys(boc)-OH (100 mg, 0.29 mmol) was suspended in Toluene (3 ml) and triethylamine (224 uL) over molecular sieves in a 50 ml round bottom flask equipped with a condenser. DMA (~150 uL) was added to aid solubility. The solution was heated to 125° C. and refluxed for 4 hours after which the reaction was shown to be complete by LCMS. The reaction mixture was concentrated to dryness on the rotovap, redissolved in DMSO and purified by preparative HPLC. 56 mg of product was isolated as a white powder. (60% yield)

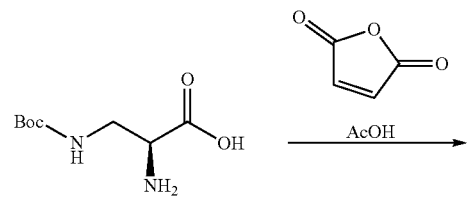

Chemical Formula: C$_8$H$_{16}$N$_2$O$_4$
Molecular Weight: 204.22

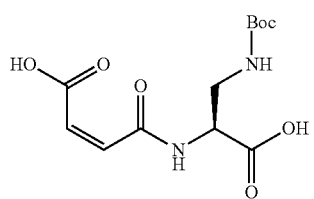

Chemical Formula: C$_{12}$H$_{18}$N$_2$O$_7$
Molecular Weight: 302.28
Maleyl-DPR(boc)OH Maleyl-DPR(boc)-OH was prepared in the same manner as Maleyl-Lysine(boc)OH. (503 mg, 67%)

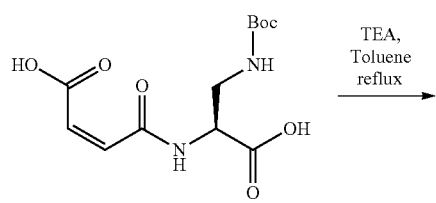

Chemical Formula: C$_{12}$H$_{18}$N$_2$O$_7$
Molecular Weight: 302.28

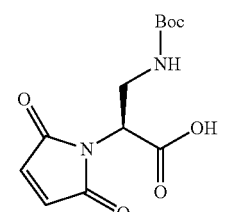

Chemical Formula: C$_{12}$H$_{16}$N$_2$O$_6$
Molecular Weight: 284.27
Maleoyl-DPR(boc)-OH Maleoyl-DPR(boc)-OH was prepared in the same manner as Maleoyl-Lys(boc). (340 mg, 71%)

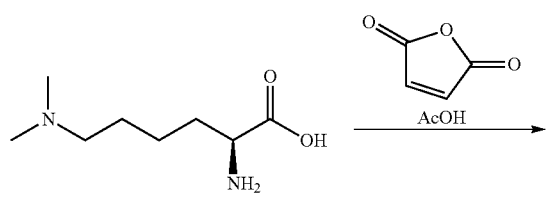

Chemical Formula: C$_8$H$_{18}$N$_2$O$_2$
Molecular Weight: 174.24

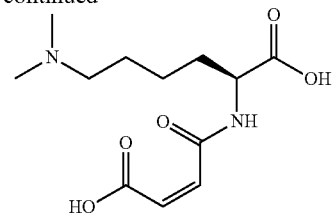

Chemical Formula: C$_{12}$H$_{20}$N$_2$O$_5$
Molecular Weight: 272.30
Maleyl-Dimethyllysine Maleyl-dimethyllysine was prepared in the same manner as Maleyl-lys(boc)-OH with the exception that the product did not precipitate after addition of dichloromethane. Instead the oil was co-evapaorated with 1:1 dichloromethane/hexane until a white foam was obtained and dried under high vacuum overnight. (109 mg, 99%)

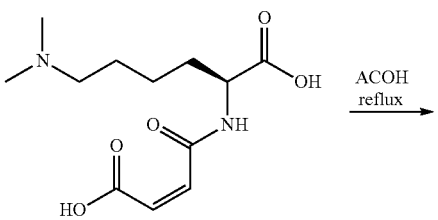

Chemical Formula: C$_{12}$H$_{20}$N$_2$O$_5$
Molecular Weight: 272.30

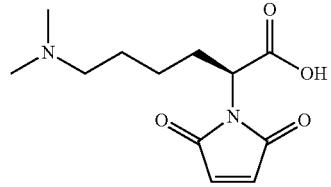

Chemical Formula: C$_{12}$H$_{18}$N$_2$O$_4$
Molecular Weight: 254.28
Maleoyl-dimethyllysine In a 10 ml round bottom flask, Maleyl-dimethyllysine (100 mg) was dissolved in acetic acid (1 ml) and refluxed for 4 hours. After 4 hours the reaction mixture was concentrated to dryness on the rotovap and dried to a white foam under high vacuum. NMR of crude material shows ~80% conversion based on ratio of the singlet at 6.9 ppm and the olefinic protons from the starting material.

Example 2

Synthesis of mDPR-Val-Cit-PAB-MMAE mDPR-Val-Cit-PAB-MMAE was prepared by coupling Boc-protected mDPR to Val-Cit-PAB-MMAE using standard methods for peptide coupling. The Boc group was removed in the final step.

Scheme:

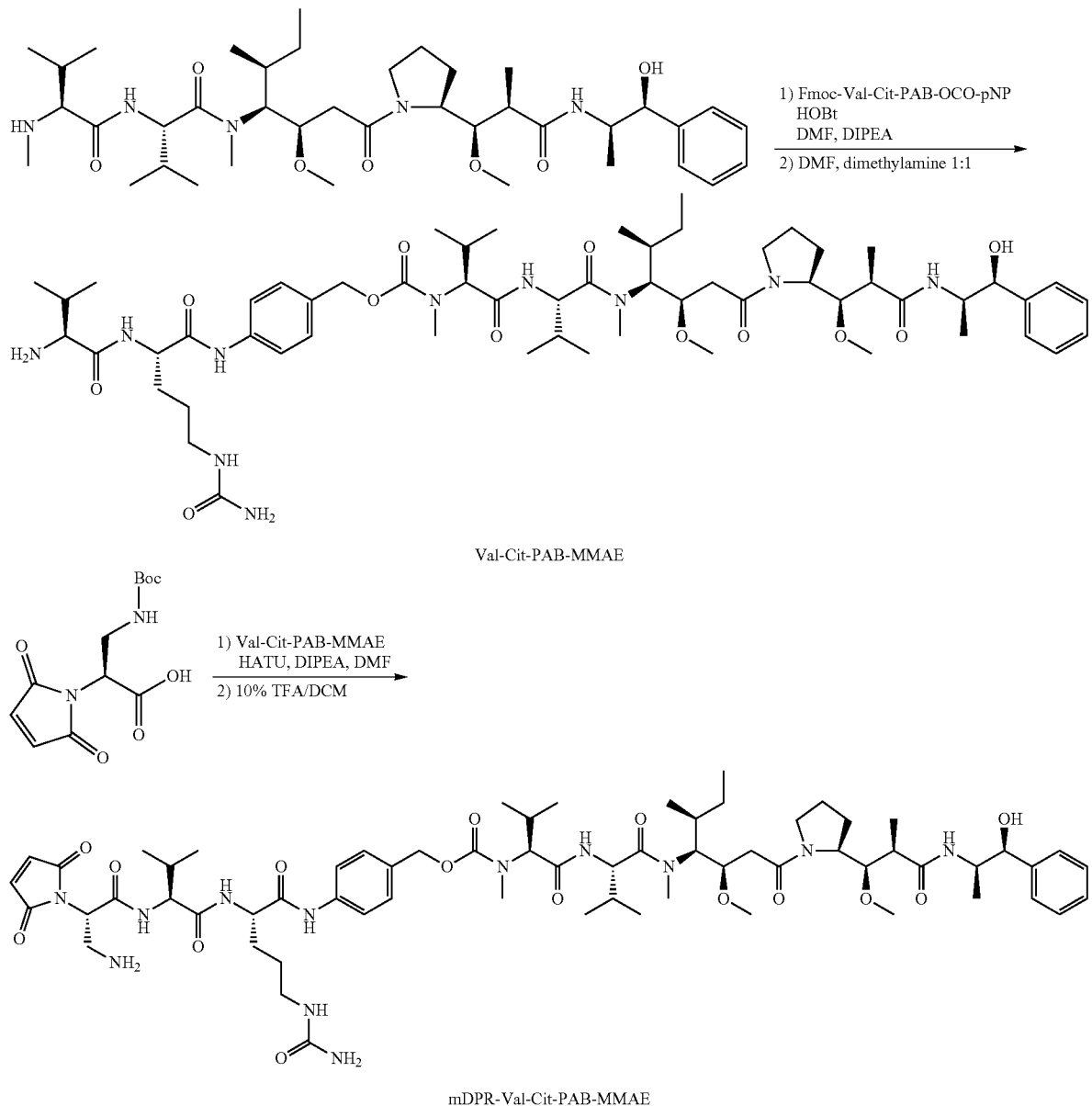

Preparation of Fmoc-Val-Cit-PAB-MMAE

MMAE (5.34 g, 6.94 mmol), Fmoc-Val-Cit-PAB-OCO-pNP (5.0 g, 6.94 mmol) and HOBt (1.4 mmol) were charged to a 250 ml round bottom flask purged with N2 and dissolved in 15 ml of DMA. DIPEA (2.44 ml, 14 mmol) was then added, and the solution was stirred overnight at room temperature under inert atmosphere. The product was isolated by preparative HPLC, using a linear gradiant from 30% MeCN (0.05% TFA) to 100% MeCN (0.05% TFA) over 40 min. Fractions containing product were concentrated on the rotovap to a white powder, affording 3.2 g (34%)

Preparation of Val-Cit-PAB-MMAE

A solution of 3.2 g of Fmoc-Val-Cit-PAB-MMAE in 7 ml DMF and 7 ml diethylamine was stirred for 3 hours at room temperature. The reaction mixture was then concentrated to a thick oil on the rotovap. The product was precipitated in diethyl ether (100 ml) and filtered affording 2.0 g of product as an off white powder which was used without further purification.

Preparation of mDPR (boc) Val-Cit-PAB-MMAE

In a 50 ml round bottom flask mDPR(boc)-OH (25 mg, 0.089 mmol), Val-Cit-PAB-MMAE (100 mg, 0.089 mmol), and HATU (41 mg, 0.107 mmol) were dissolved in 2 ml DMF. DIPEA (34 uL) was added and the solution was stirred for 1 hr at rt. The reaction mixture was diluted with 1 ml DMSO and the product was isolated by preparative HPLC. (70 mg, 56%)

Preparation of mDPR -Val-Cit-PAB-MM-AE

The above material was dissolved in 2 ml 10% TFA/ dichloromethane and stirred for 1 h at rt. The reaction mixture was concentrated to dryness, reconstituted in 1 ml DMSO, and purified by preparative HPLC. (56 mg, 86%)

Example 3

Monitoring Thiosuccinimide Hydrolysis

Figure 1B:
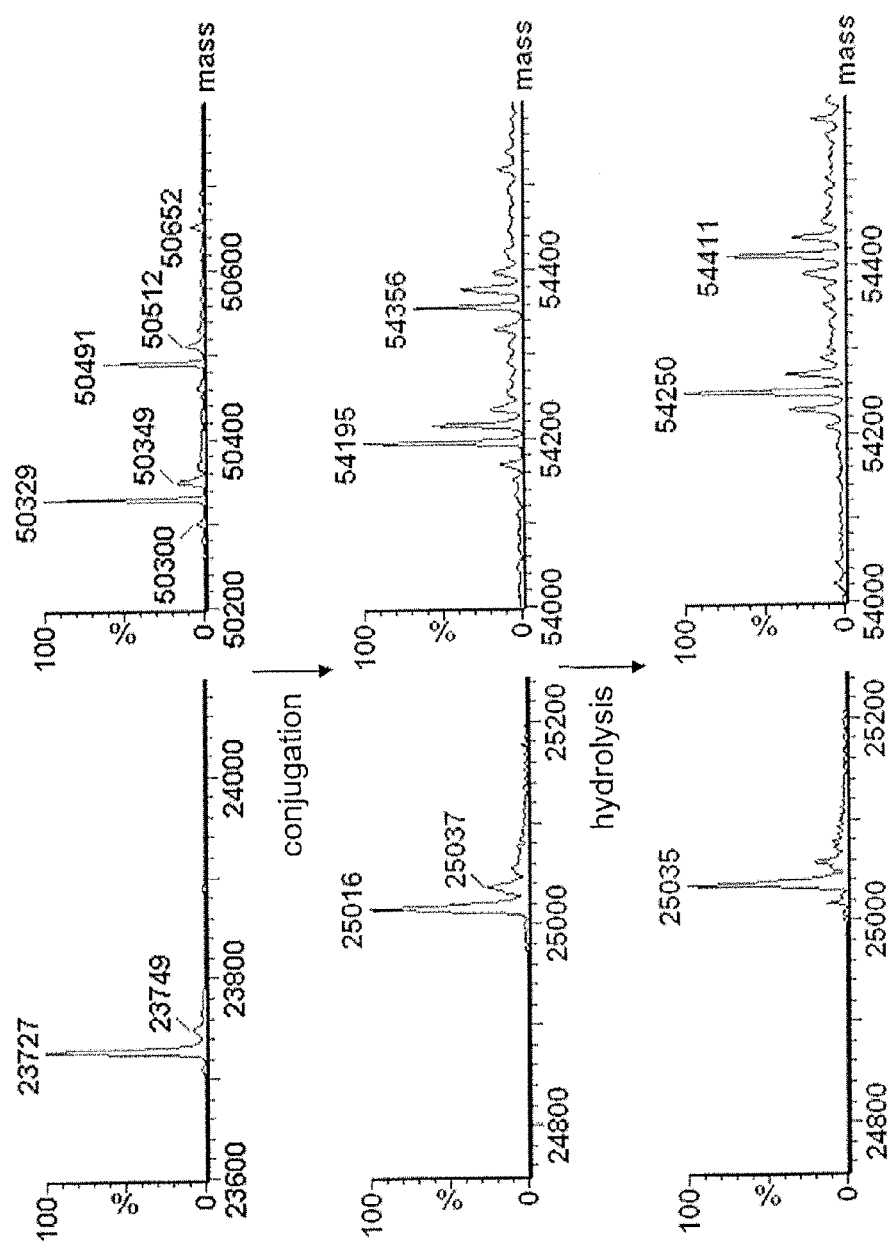

Thiosuccinimide hydrolysis of a self-stabilizing bioconjugate can be monitored by electrospray mass spectrometry, since the addition of water to the conjugate results in an increase of 18 Daltons to the observable molecular weight of the conjugate. When a conjugate is prepared by fully reducing the interchain disulfides of a human IgG1 antibody and conjugating the maleimide to the resulting cysteines, each light chain of the antibody will contain a single maleimide modification and each heavy chain will contain three maleimide modifications (see FIG. 1, top). Upon complete hydrolysis of the resulting thiosuccinimides, the mass of the light chain will therefore increase by 18 Daltons, while the mass of the heavy chain will increase by 54 Daltons. This is illustrated in FIG. 1 (bottom), with the conjugation and subsequent hydrolysis of a self-stabilizing maleimide drug-linker of the present invention (mDPR-Val-Cit-PAB-MMAE, molecular weight 1289 Da) to the fully reduced anti-CD30 antibody cAC10. The presence of the single N-linked glycosylation site on the heavy chain results in the heterogeneity of masses observed in the unconjugated antibody.

Example 4

Monitoring t1/2 Hydrolysis

Figure 2A:
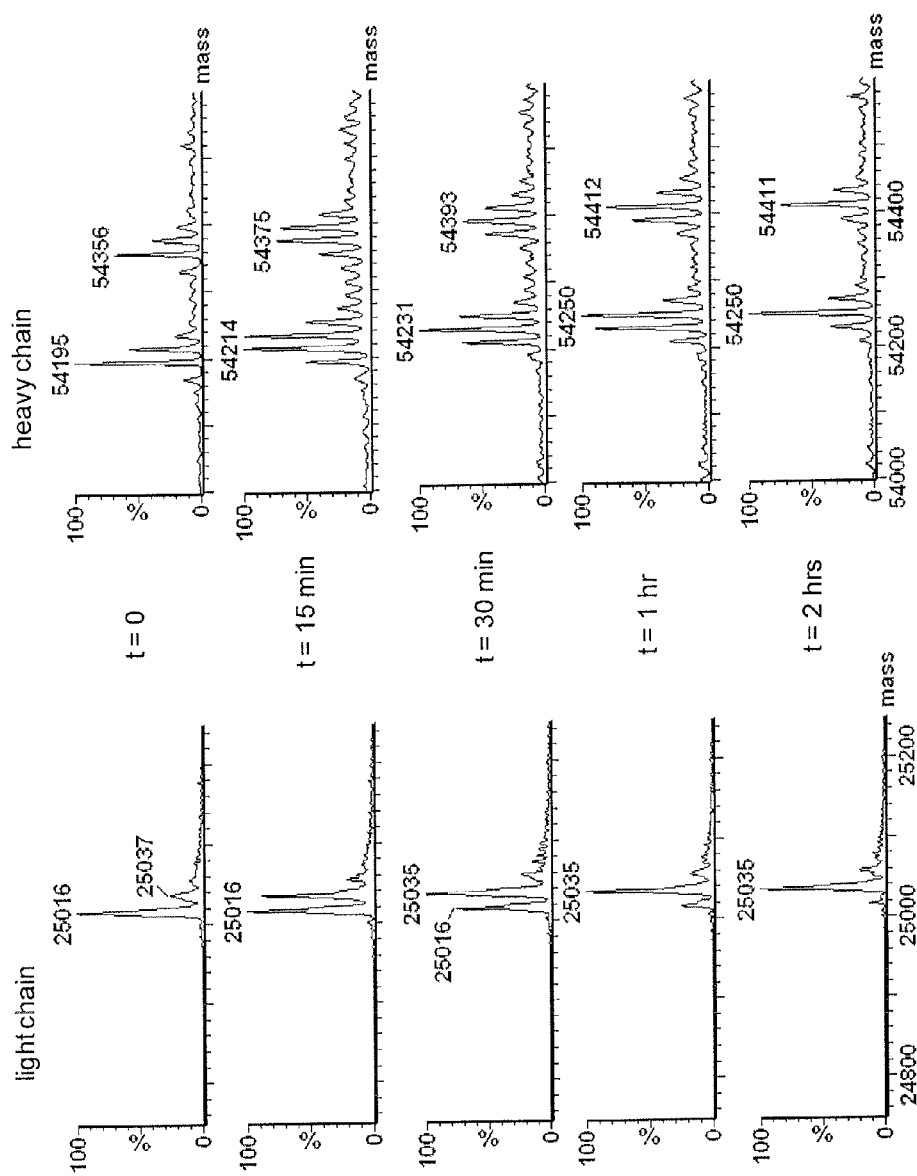
FIGS. 2A and 2B illustrate the timecourse of succinimide ring hydrolysis of a self-stabilizing antibody conjugate by electrospray mass spectrometry. Conjugation of fully reduced cAC10 with maleimido-DPR-val-cit-PAB-MMAE was performed at pH 7.2 and 22° C., then samples were subjected to analysis by LC-MS at the indicated times (FIG. 2A). The resulting data of % hydrolysis was plotted versus time and fit to an exponential equation to determine kinetic parameters (FIG. 2B).
Figure 2B:
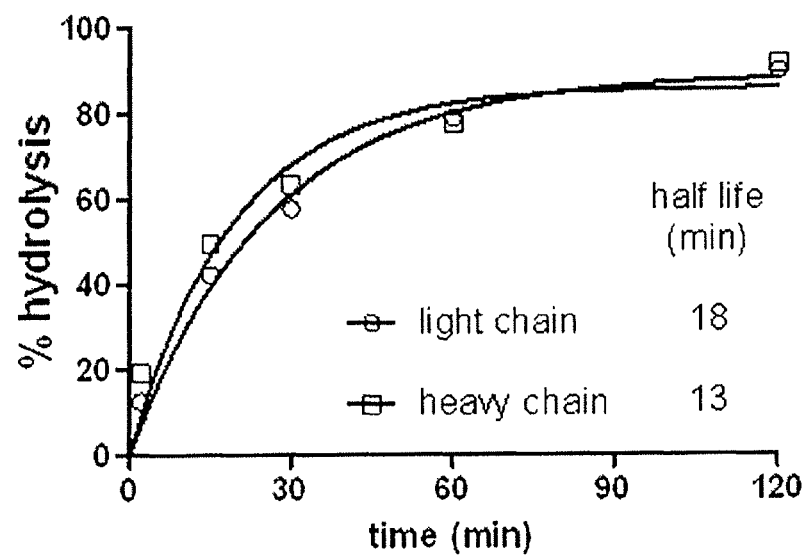
Figure 3:
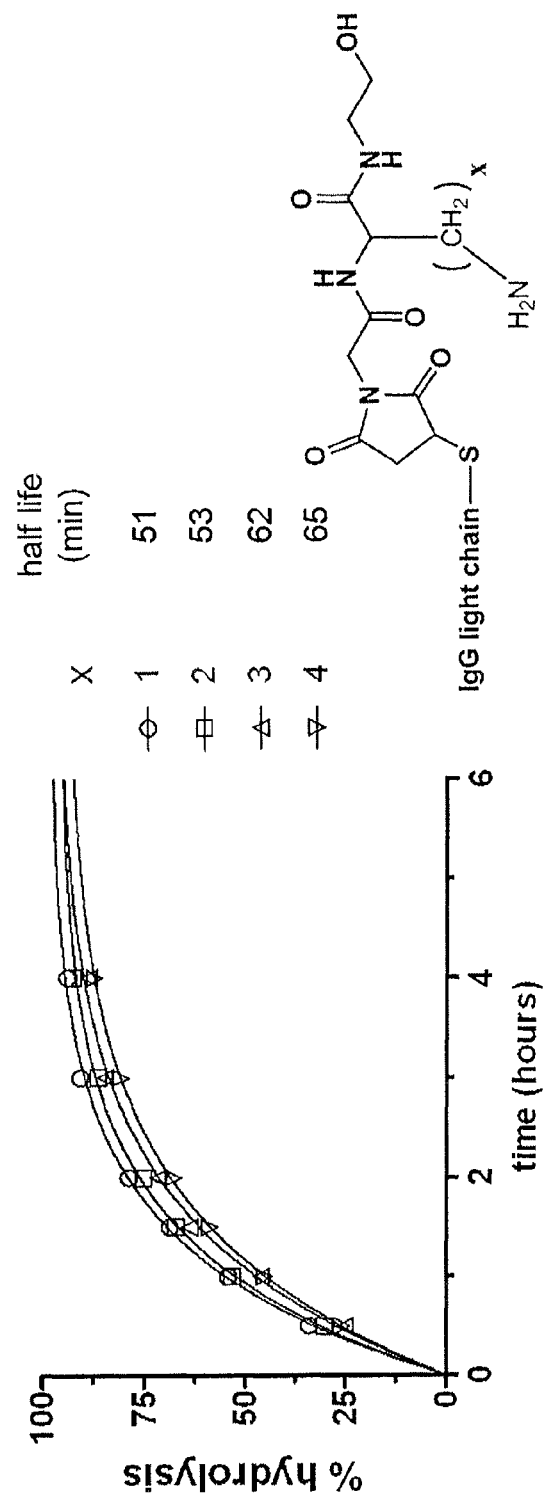
FIG. 3 provides the hydrolysis kinetic profiles for bioconjugates prepared with an IgG1 antibody and self-stabilizing linkers with varying spacing between the maleimide and the basic group (a primary amine). Conjugation was performed at pH 8 and 37° C., then hydrolysis of the IgG1 light chain conjugate was immediately monitored by mass spectrometry, plotted as a function of time, and fit to an exponential equation.

By monitoring the intensities of the non-hydrolyzed and hydrolyzed peaks in the mass spectrum of a self-stabilizing bioconjugate over time (mDPR-Val-Cit-PAB-MMAE), the hydrolysis kinetics can be evaluated. This is done by plotting the percent of the total population which has hydrolyzed at each timepoint versus time (FIG. 2, top). These data are then fit to the exponential equation $$Y = Y_{max} \times (1 - e^{(-Kt)})$$

where Y is the observed percent hydrolysis at time t, Ymax is the asymptotic maximal % hydrolysis, and K is the hydrolysis rate constant. The half-life for the hydrolysis reaction is defined as $$t_{1/2} = \ln(2)/K$$

When this procedure is performed on the light chain of a reduced hIgG1 antibody, the analysis is quite straightforward as there is only one conjugation site per light chain and the reaction is a simple progression from the unhydrolyzed species to the hydrolyzed species with a mass change of 18 Daltons. Performing this analysis on the heavy chain is complicated by the fact that there are a total of three conjugation sites, resulting in a series of peaks of +18, +36, and +54 Daltons as the conjugate undergoes hydrolysis. The analysis of the heavy chain is further complicated by the presence of multiple glycoforms. The analysis presented in FIG. 2 was performed by only evaluating the peaks arising from the most abundant glycoform (the transition from 54195 Da to 54250 Da) and assuming that these peaks are a reasonable surrogate for the whole population of heavy chain glycoforms. As is evident in FIG. 2, the observed kinetic profiles for light and heavy chains are very similar. For this reason, and because of the added complexities of quantifying hydrolysis rates on the heavy chain noted above, most of the data to characterize hydrolysis rates of self-stabilizing maleimides conjugated to antibodies was determined from evaluation of the light chain hydrolysis.

One limitation of this methodology is that the electrospray ionization process tends to produce a small proportion of sodium adducts in the observed peaks (approximately 10% under the conditions used to generate the data in FIG. 2), which have an observed mass 22 Daltons greater than the parent mass. Many mass spectrometers do not have sufficiently high resolution to resolve this +22 mass from the +18 mass that results from hydrolysis on a protein with a total molecular mass in excess of 25,000 Daltons. Consequently, at the early timepoints when the degree of hydrolysis is low, the appearance of a peak at approximately +20 Daltons is a combination of these two effects which cannot be easily separated experimentally. As a result, the estimate of the percent of hydrolyzed product at the earliest timepoints is probably an overestimate, but the magnitude of this effect diminishes as the reaction proceeds toward completion

Example 5

Evaluating Spacing Between the Maleimide and Basic Group of the Self-Stabilizing Linker Assembly It was hypothesized that the presence of a basic amino group adjacent to maleimide would accelerate the hydrolysis of thiosuccinimides prepared with those maleimides and thus result in stable bioconjugates. The distance between the maleimide and the basic amino group was recognized as an important parameter in the design of such self-stabilizing units. To evaluate the role of this spacing, a series of maleimides were prepared with the general structure

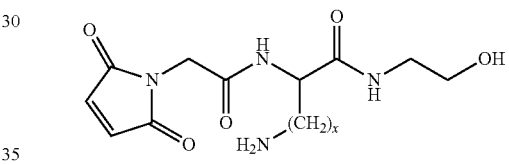

where x varied from 1 to 4. These maleimides were then conjugated to a fully reduced human IgG1 at pH8 and 37° C. and immediately monitored by electrospray mass spectrometry to determine the rate of hydrolysis. The distance between the basic group and the maleimide is inversely proportional to the hydrolysis rate—that is, the greater the distance, the slower the hydrolysis. This result illustrates that positioning a basic amino group close to a maleimide results in an increase in the rate of succinimide ring hydrolysis of bioconjugates prepared with the maleimide. However, even with the shortest spacing tested here (x=1), an antibody conjugate would have to be held at pH 8 and 37° C. for approximately 5 hours to achieve complete hydrolysis (about 5 half-lives). Exposure of an antibody or other protein to such conditions for extended periods can potentially result in covalent modifications and misfolding events, and so maleimides with even faster hydrolysis rates were sought.

To prepare bioconjugates with faster hydrolysis rates, a series of maleimides were prepared with the general structure

Figure 4:
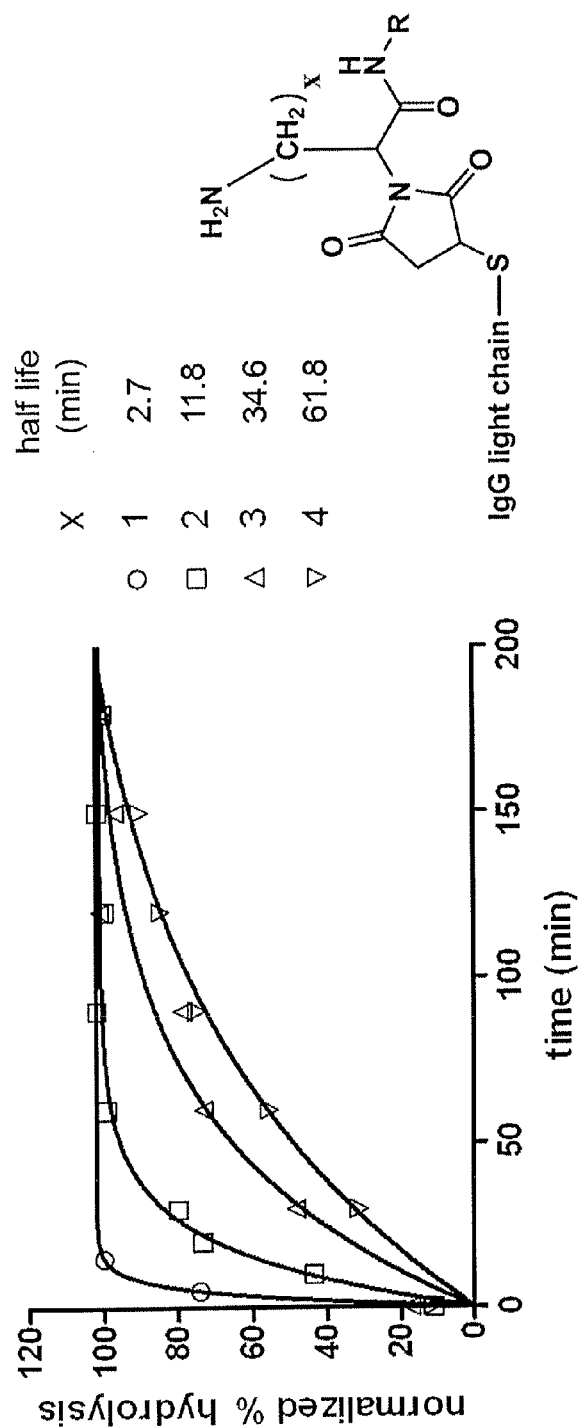
FIG. 4 provides kinetic profiles of the hydrolysis of bioconjugates prepared with an IgG1 antibody and self-stabilizing maleimide linkers with varying spacing between the maleimide and the basic group (a primary amine). Conjugation was performed at pH 8 and 37° C., then hydrolysis of the IgG1 light chain conjugate was immediately monitored by mass spectrometry, plotted as a function of time, and fit to an exponential equation.

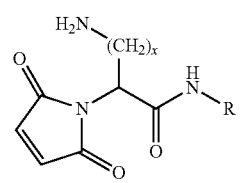

where x=1 to 4 and R=val-cit-PAB-MMAE. These maleimides were then conjugated to a fully reduced human IgG1 at pH8 and 37° C. and immediately monitored by electrospray mass spectrometry to determine the rate of hydrolysis. As shown in FIG. 4 (top), the distance between the basic group and the maleimide within this series of structurally related compounds exerts a profound influence on the progress of the hydrolysis reaction. As in the prior example, the shorter the distance between the maleimide and the basic amine, the faster the hydrolysis. Since basic conditions (i.e. high pH) are known to increase the rate of maleimide and succinimide ring hydrolysis, this effect is presumably an example of intramolecular catalysis by a general base mechanism. Within this series the compounds with x=2 and x=3 did not attain complete hydrolysis during the 3 hour incubation, instead reaching an asymptote at approximately 80% and 50%, respectively (plots are normalized to the maximally achieved hydrolysis). This phenomenon may arise from a competing reaction such as direct nucleophilic attack of the primary amine on the succinimide ring, or may be due to an isomeric impurity in the maleimide which leads to biphasic hydrolysis kinetics.

Example 6

Hydrolysis Kinetics

Figure 5:
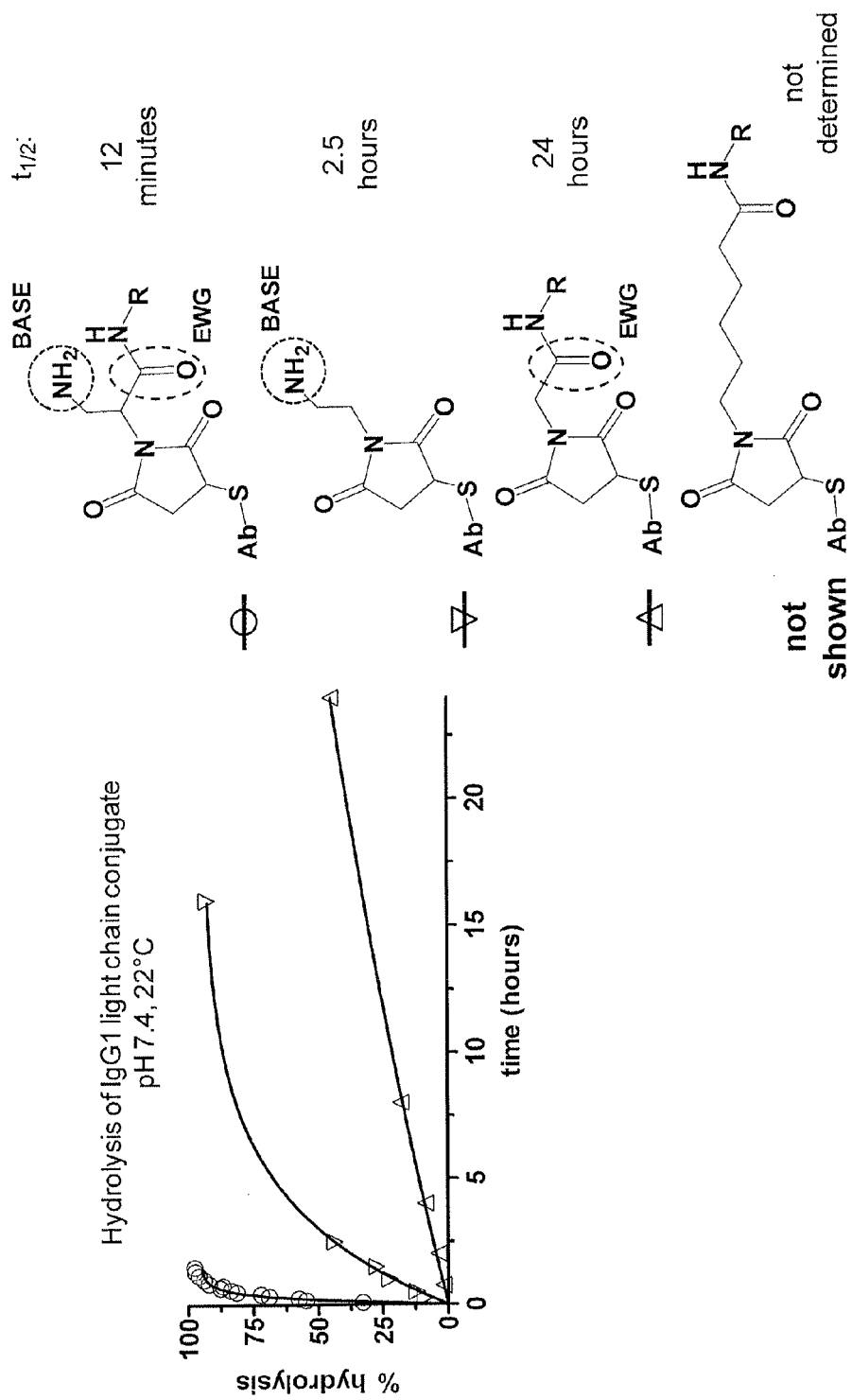
FIG. 5 provides hydrolysis kinetic profiles for bioconjugates prepared with an IgG1 antibody and various N-substituted maleimides. Conjugation was performed at pH 7.4 and 22° C., then hydrolysis of the IgG1 light chain conjugate was immediately monitored by mass spectrometry, plotted as a function of time, and fit to an exponential equation. Hydrolysis of the maleimido-caproyl conjugate (bottom structure) is too slow to produce any detectable hydrolysis in 24 hours under these conditions. The presence of the carboxamide electron withdrawing group (EWG) or the primary amine (BASE) accelerate the hydrolysis, and the combination of the two (top structure) results in a conjugate which hydrolyzes with a half-life of less than 20 minutes under these mild conditions.

The previous examples illustrate the influence that a basic group can have over the rate of succinimide ring hydrolysis in a bioconjugate, depending on the distance between the basic group and the maleimide of the parent molecule. However, it is expected that the presence of electron-withdrawing or -donating groups will also influence the rate of ring hydrolysis, since these groups will influence the electron density (and therefore electrophilicity) at the carbonyl carbons of the ring. In the conjugates of example 5, a carboxamide group is present in the alpha position relative to the nitrogen of the ring (i.e. a single carbon atom is present between the nitrogen of the ring and the carbonyl carbon of the carboxamide). Because the carboxamide is a weak electron withdrawing group, its presence is likely to influence the observed hydrolysis rates. To better understand the relative contributions of the basic amino group and the electron-withdrawing carboxamide group on the observed hydrolysis rates, a series of maleimides were conjugated to a reduced human IgG1 antibody at pH 7.4, 22° C., and the hydrolysis rates determined by mass spectrometry (FIG. 5). These maleimides contained just the carboxamide in the alpha position (triangles), just the primary amine in the beta position (inverted triangles), or both the carboxamide and the primary amine (circles). A control maleimide which contained neither group in proximity to the maleimide was also evaluated, although its hydrolysis is so slow that no reaction was observed under these conditions and no data is plotted. Under these conditions the self-stabilizing maleimide which contains both the base and the electron withdrawing group produced a bioconjugate with a hydrolysis $t_{1/2}$ of just 12 minutes, while the maleimide containing only the amine yielded a $t_{1/2}$ of 2.5 hours, and the maleimide containing only the carboxamide yielded a $t_{1/2}$ of 24 hours. This result indicates that the basic group and the electron withdrawing group act in concert to yield a conjugate with the very rapid hydrolysis kinetics which are most convenient for the manufacture of bioconjugates under the desirable mild conditions. Conjugates prepared with the diaminopropionyl maleimide (circles) exhibit ideal hydrolysis characteristics, with a $t_{1/2}$ of less than 15 minutes under very gentle conditions and the reaction approaching 100% completion in about 2 hours.

Example 7

Evaluating Spacing Between the Maleimide and Carboxamide Group of the Self-Stabilizing Linker Assembly The rapid and complete succinimide hydrolysis observed in conjugates prepared with self-stabilizing diaminopropionyl maleimido drug-linkers acid (DPR) shown in examples 5 and 6 above indicates the importance of both the basic group and the electron withdrawing group to the design. A second, isomeric maleimido drug-linker was prepared with diaminopropionic acid to further evaluate the role of these two components on the hydrolysis behavior of the resulting conjugates. The structures are termed α-maleimido DPR and β-maleimido DPR and are shown below.

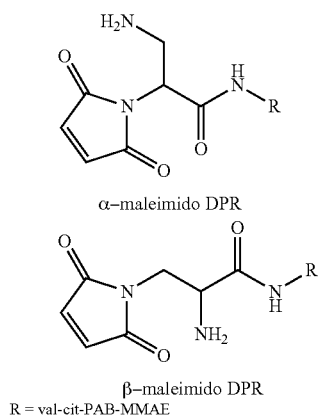

α-maleimido DPR

β-maleimido DPR
R = val-cit-PAB-MMAE

Figure 6:
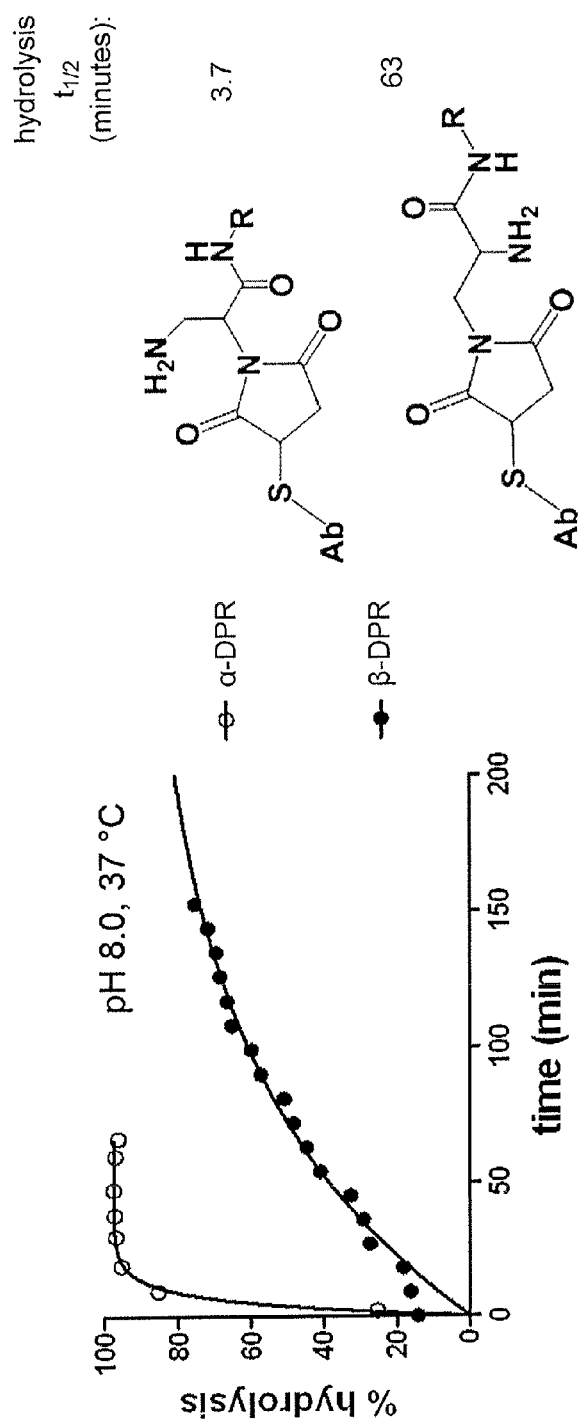
FIG. 6 provides hydrolysis kinetic profiles for self-stabilizing maleimido drug-linkers prepared with α-diaminopropionic acid (α-DPR, open circles) and with β-diaminopropionic acid (β-DPR, filled circles). Although isomers of each other, the positioning of the basic amino group and the electron withdrawing carboxamide relative to the succinimide results in a 17-fold difference in the rate of succinimide hydrolysis.

Both DPR maleimides possess a basic primary amine which is separated from the maleimido nitrogen by two carbon atoms. Both also possess an electron withdrawing carboxamide group, however the distance from the maleimido nitrogen the carboxamide varies from 1 to 2 carbon units (α and β, respectively). Finally, the separation between the basic amine and the carboxamide also varies from 1 to 2 carbon units and a, respectively). Collectively, this means that in β-DPR the carboxamide exerts less electron withdrawing influence on the maleimide ring but more electron withdrawing influence on the primary amine, relative to α-DPR. This is expected to slow the rate of hydrolysis by reducing both the electrophilicity of the maleimide and the basicity of the primary amine. When these maleimido drug-linkers were conjugated to reduced antibody and monitored for succinimide hydrolysis, a 17-fold lower hydrolysis rate was observed for β-DPR relative to α-DPR (FIG. 6). This example illustrates how the relative positioning of a basic group and an electron withdrawing group can be used to 'tune' the hydrolysis rate.

Examples 8-15

Figure 7A:
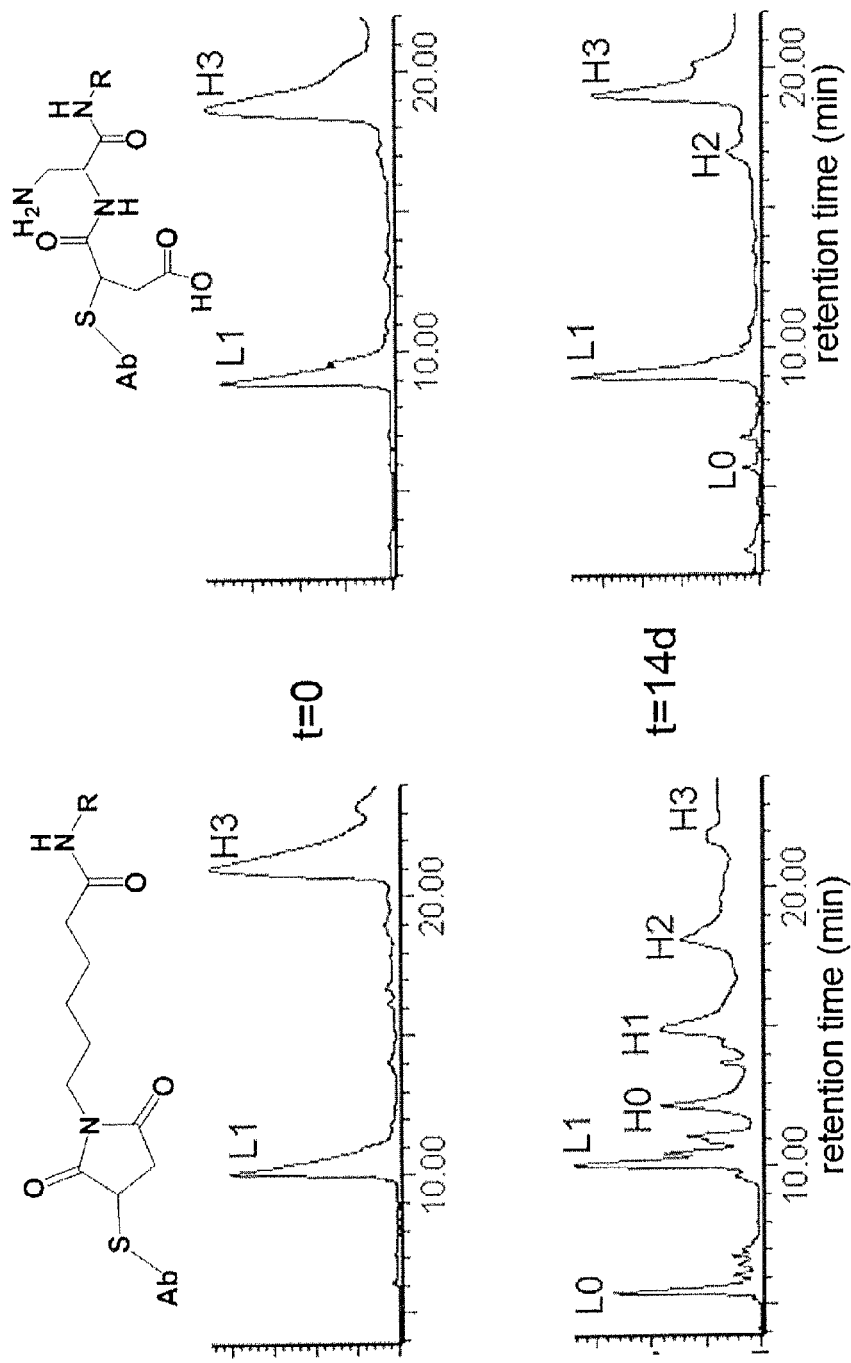
FIGS. 7A and 7B illustrate the change in drug loading over time for an ADC prepared with a self-stabilizing maleimido-DPR drug-linker versus one prepared with a maleimido-caproyl drug linker when incubated in a buffer containing excess thiol. The reversed-phase chromatograms of the two ADCs at time zero and time 14 days after incubation is shown in the top panel. Chromatographic peak assignments L0, L1, H0, H1, H2, and H3 correspond to unconjugated light chain, light chain with one drug, unconjugated heavy chain, and heavy chain with 1, 2, or 3 drugs, respectively. The self-stabilizing maleimido-DPR drug-linker is represented with open circles versus one prepared with a maleimido-caproyl drug linker (open squares). Drug loading remains constant at 8 per antibody for the self-stabilizing drug-linker (open circles), but falls to 4 drugs per antibody over 14 days for the maleimido-caproyl drug linker (open squares), reflecting loss of drug by maleimide elimination.
Figure 7B:
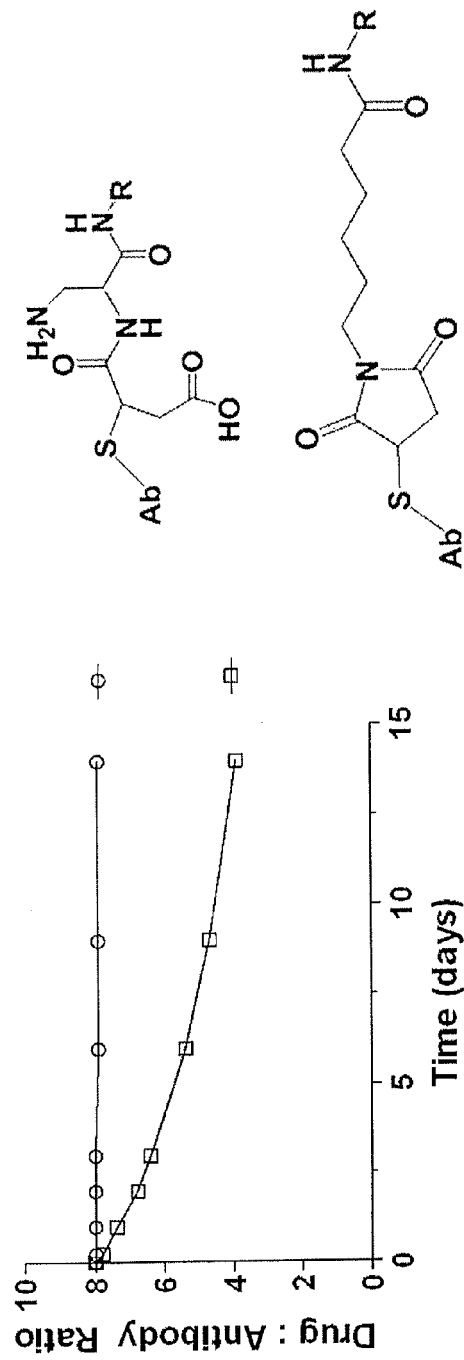

To evaluate the stability and pharmacological activity of ADCs prepared with self-stabilizing drug-linkers, a self-stabilizing maleimido-drug-linker was prepared. This drug-linker contains the maleimido-DPR group coupled to the cytotoxic agent MMAE via a protease-cleavable val-cit PAB self-immolative group (referred to herein as maleimido-DPR-val-cit-PAB-MMAE). For comparison, a non self-stabilizing drug-linker was used (referred to herein as maleimido-caproyl-val-cit-PAB-MMAE). The only difference between these agents is the unit between the maleimide and the valine group of the val-cit linker. The maleimide units of these drug-linkers can be prepared using maleic anhydride and mono-protected diaminopropionic acid and aminocaproic acid, respectively etry. These ADCs were placed in 150 mM Tris buffer, pH 8, at 2.5 mg/mL, containing 10 mM N-acetylcysteine as a scavenger, and incubated for 2 weeks at 37° C. At seven timepoints during the incubation, an aliquot of each ADC was removed and frozen at −80° C. Upon completion of the time-course, all samples were analyzed by the above reversed-phase HPLC method to determine the drug:antibody ratio. The results of this study are shown in FIG. 7. The ADC prepared with the self-stabilizing DPR maleimido drug-linker exhibited minimal loss of drug over this time-

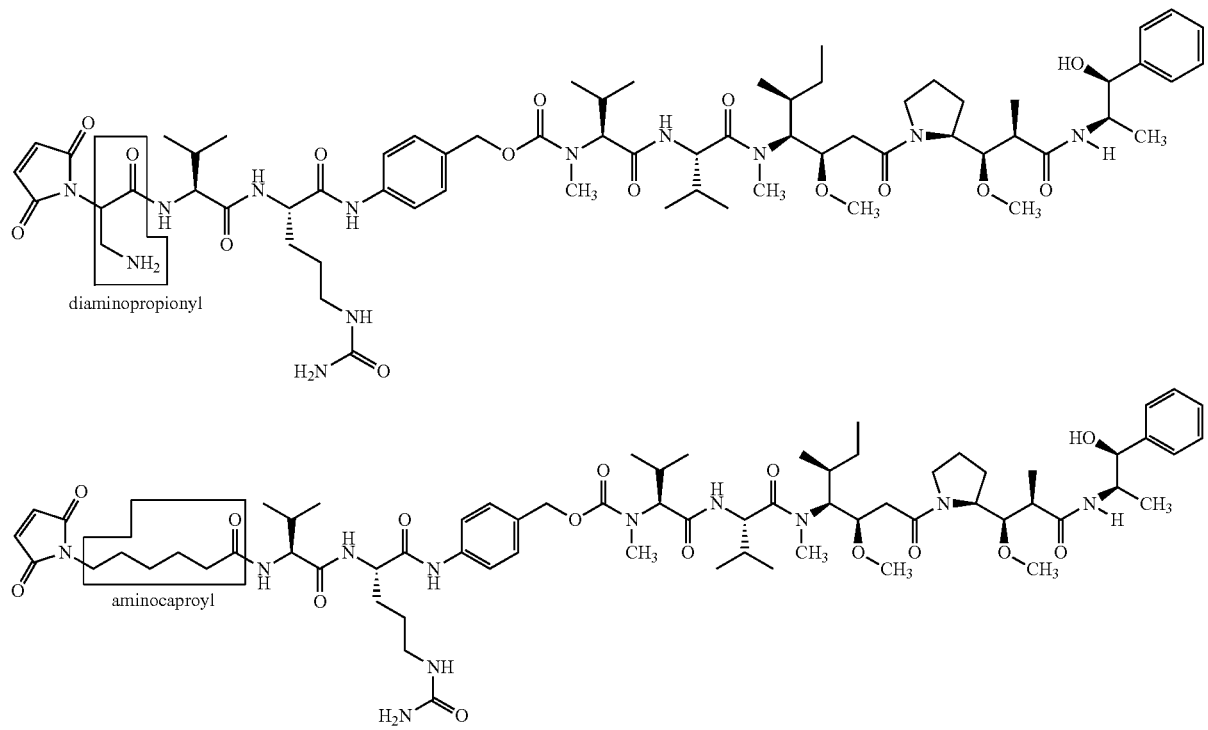

Example 8

Evaluating Stability of Ligand-Drug Conjugates in Buffer

In standard buffer systems, maleimide elimination from a bioconjugate prepared using thiol-maleimide chemistry is essentially undetectable because the eliminated maleimide quickly reacts again with the thiol, resulting in an equilibrium which lies far toward the side of the intact conjugate. However, the addition of a thiol scavenger to the buffer creates a system in which maleimide that eliminates from the bioconjugate can instead react with the scavenger, resulting in a persistent, observable loss of the maleimide from the protein. An experiment using such a system was performed with antibody-drug conjugates prepared with a self-stabilizing diaminoproprionyl (DPR) maleimido drug-linker alongside a non-stabilizing caproyl drug-linker. ADCs were prepared with 8 drugs per antibody of either maleimido-DPR-val-cit-PAB-MMAE or maleimido-caproyl-val-cit-PAB-MMAE using a fully reduced humanized IgG1. Drug loading was confirmed by reversed-phase HPLC on a polymeric PLRP—S column as described previously (Sun 2005). Complete succinimide hydrolysis of the self-stabilizing linker was also confirmed by electrospray mass spectromcourse (from 8.0 to 7.9 drugs per antibody over 14 days), while the ADC prepared with the caproyl maleimido drug-linker lost approximately half of its drug load (from 8.0 to 3.9 drugs per antibody over 14 days) under these conditions.

Example 9

Ex Vivo Plasma Stability (Reversed Phase Method)

Figure 8:
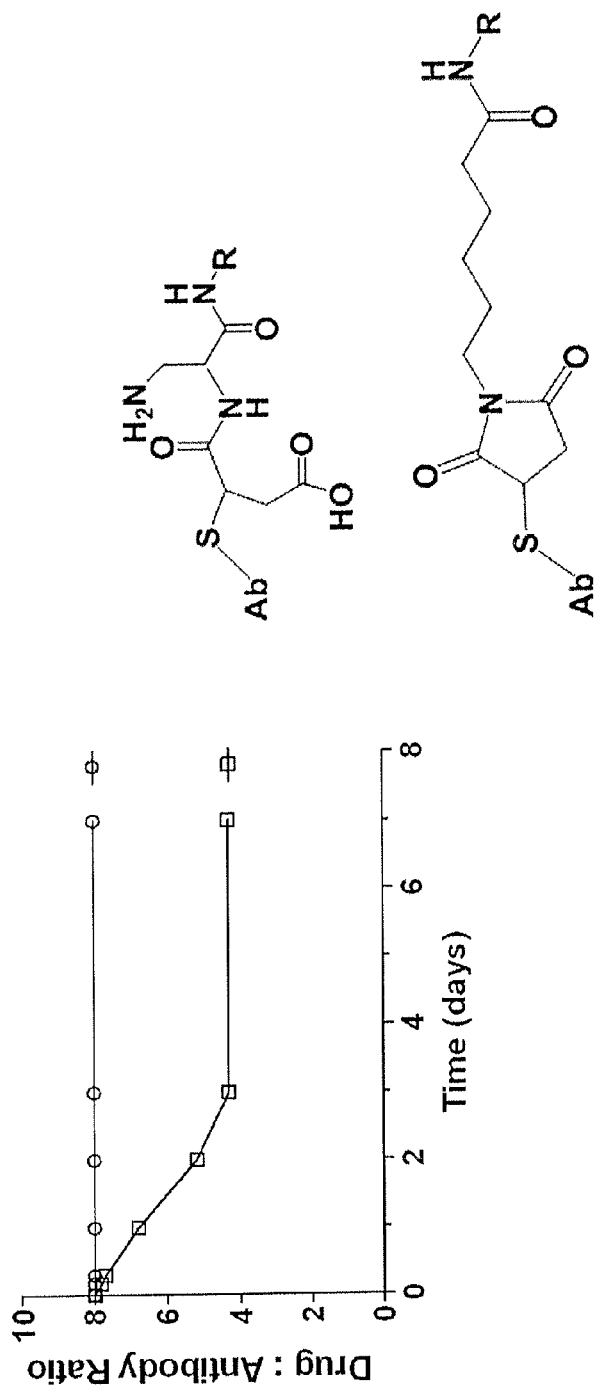
FIG. 8 illustrates the change in drug loading over time for ADCs prepared with a self-stabilizing maleimido-DPR drug-linker and a maleimido-caproyl drug linker, when incubated in rat plasma at 37° C. (R=val-cit-PAB-MMAE). ADC samples at each timepoint were purified by Ig Select affinity resin and their drug loading evaluated by reversed-phase HPLC analysis of the ADCs.

Assessing drug loading of humanized ADCs in non-human plasma samples by the reversed-phase HPLC method described in Example 8 can be achieved by first isolating the ADCs with IgSelect resin (GE Healthcare), which selectively binds to the human Fc domain. ADCs were prepared with 8 drugs per antibody of either maleimido-DPR-val-cit-PAB-MMAE or maleimido-caproyl-val-cit-PAB-MMAE using a fully reduced human IgG1. These ADCs (0.25 mg/mL) were incubated in sterile rat plasma for 7 days at 37° C. At seven timepoints during the incubation, a 50 µL aliquot of each ADC was removed and frozen at −80° C. Upon completion of the timecourse, ADCs were purified from each sample and analyzed by reversed-phase HPLC to determine the drug:antibody ratio. The results of this study are plotted in FIG. 8. As was observed in buffer, incubation of an ADC prepared with a self-stabilizing maleimide in rat plasma also results in little or no observable loss of drug under conditions which result in the loss of approximately half of the drug from a maleimido-caproyl ADC.

Example 10

Ex Vivo Plasma Stability (Conjugated Drug Method)

Figure 9:
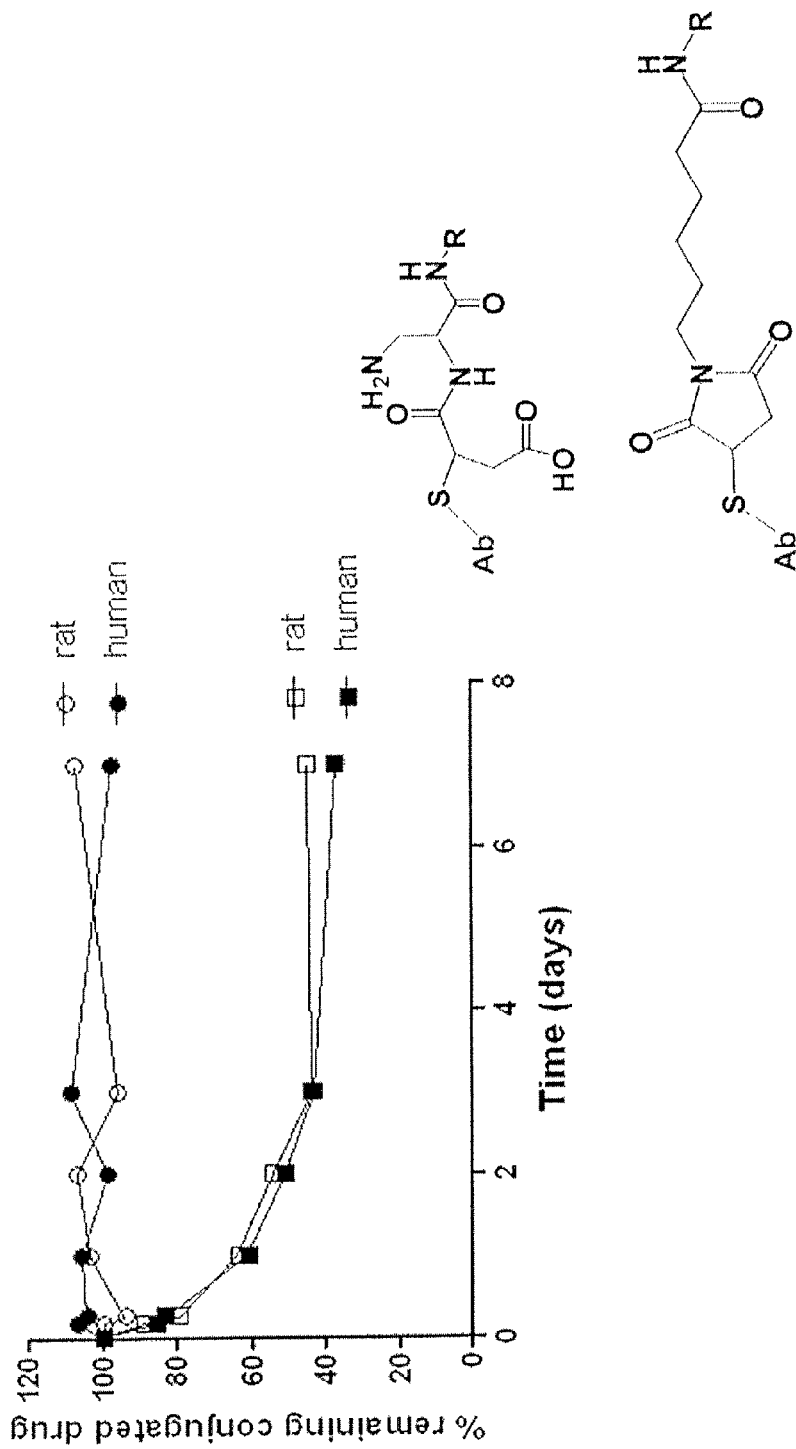
FIG. 9 provides the stability profile of drugs conjugated to antibodies via a maleimido-caproyl drug-linker (squares) or a self-stabilizing maleimide linker(circles) during incubation in rat (open symbols) or human (filled symbols) plasma (R=val-cit-PAB-MMAE). ADCs were captured on Protein A affinity resin at each timepoint and the drug released enzymatically via its protease-cleavable linker. The released drug was then quantified by LC-MS/MS and normalized to the initial value. Each timepoint reflects the percent of the conjugated drug that was observed at t0.

A second assay format was utilized to assess ADC stability in rat and human plasma ex vivo. ADCs were prepared with 4 drugs per antibody of either maleimido-DPR-val-cit-PAB-MMAE or maleimido-caproyl-val-cit-PAB-MMAE using a human IgG1 partially reduced to a level of 4 thiols per antibody (resulting in an ADC with 4 drugs per antibody). These two ADCs were spiked into rat and human plasma and incubated at 37° C. for 7 days. At seven timepoints during this incubation, aliquots were removed and frozen at −80° C. until completion of the timecourse. ADCs were then isolated from each sample and MMAE released proteolytically from the isolated ADCs as described previously (Sanderson 2005). The released MMAE was then quantified by LC-MS/MS and normalized to the initial value for each ADC (FIG. 9). In both rat and human plasma, the ADC prepared with a self-stabilizing maleimide lost little or no drug under these conditions, while approximately half of the drug was lost from a maleimido-caproyl ADC.

Example 11

In Vivo Stability

Figure 10:
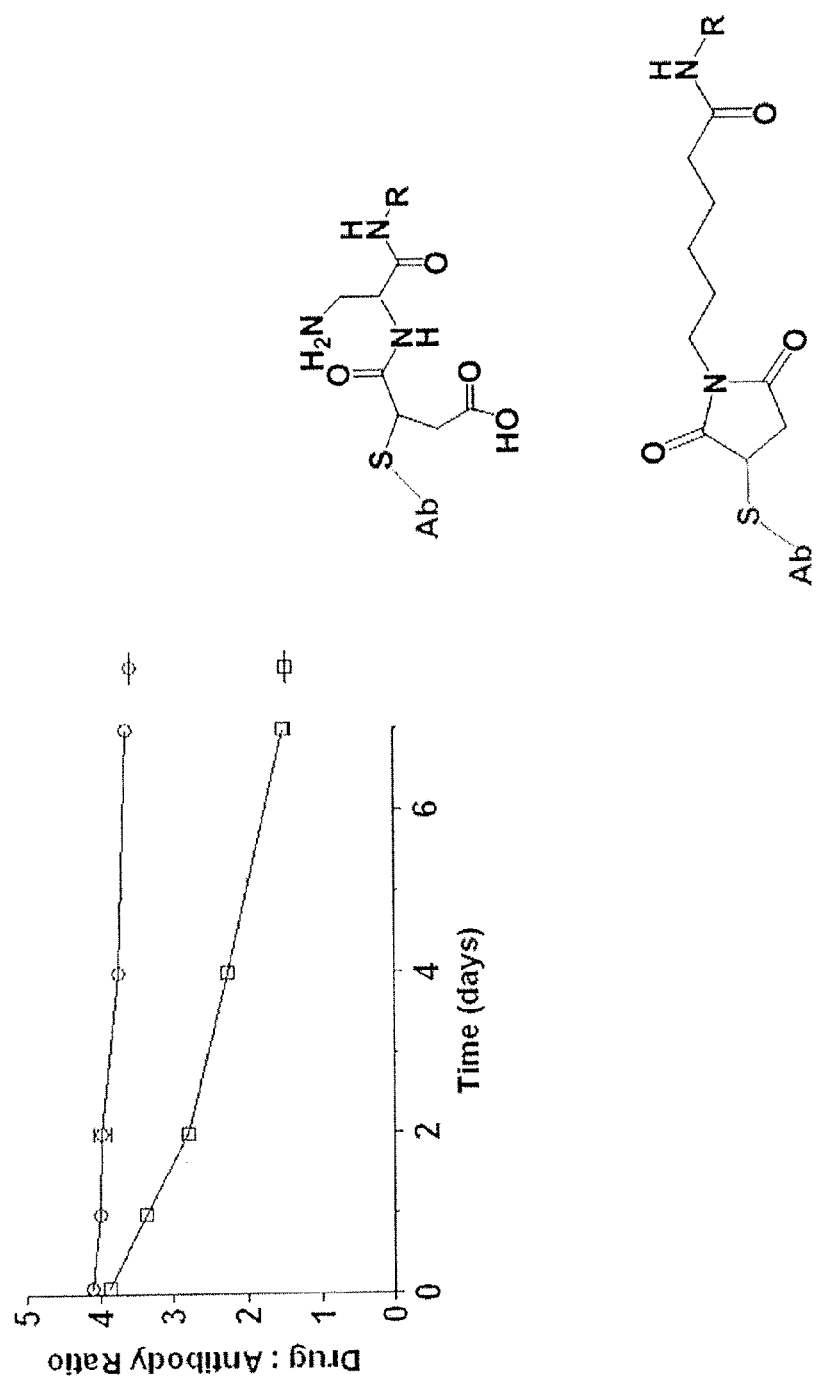
FIG. 10 illustrates the decrease in drug loading in vivo (rats) for ADCs prepared with a self-stabilizing maleimido-DPR drug-linker and a maleimido-caproyl drug linker (R=val-cit-PAB-MMAE). ADCs were dosed i.v. and plasma samples from each timepoint were purified by Ig Select affinity resin and their drug loading evaluated by reversed-phase HPLC analysis of the ADCs.

As described in Example 10 above, the drug:antibody ratio can be measured for ADCs in rat plasma by reversed-phase HPLC analysis following purification with IgSelect resin. This method was applied to samples derived from an in vivo pharmacokinetic experiment in rats. ADCs were prepared with 4 drugs per antibody of either maleimido-DPR-val-cit-PAB-MMAE or maleimido-caproyl-val-cit-PAB-MMAE using a humanized IgG1 partially reduced to an average of 4 thiols per antibody (resulting in drug:antibody ratio of 4). These ADCs were further purified as described previously (Sanderson 2005) by hydrophobic interaction chromatography to isolate the species containing 4 drugs per antibody. These ADCs were dosed intravenously at 10 mg/kg in Sprague-Dawley rats. At five timepoints, three animals from each dosing group were sacrificed and the collected blood was processed to plasma and frozen at −80° C. Upon completion of the study, all samples were processed by the IgSelect resin method described above, except that the sample volume varied. The drug:antibody ratio at each timepoint in this study are plotted in FIG. 10. As was observed in rat plasma ex vivo, the ADC prepared with a self-stabilizing maleimide exhibits minimal loss of drug in vivo, dropping from an initial value of 4.1 drugs per antibody to a value of 3.6 drugs per antibody (12% reduction) after 7 days. During this same timeframe, the drug:antibody ratio of an ADC prepared with a maleimido-caproyl linker dropped from an initial value of 3.9 to a value of 1.5 (61% reduction).

This illustrates that the increased stability of a self-stabilizing drug-linker that is observed ex vivo translates into an in vivo setting.

Example 12

Pharmacokinetics

Because maleimido-caproyl ADCs are prone to loss of drug through maleimide elimination whereas self-stabilizing maleimide ADCs are not, it is reasonable to predict that exposure to antibody-conjugated drug will be greater following equivalent doses of the two ADCs. To confirm this prediction, ADCs were prepared with 4 drugs per antibody of either maleimido-DPR-val-cit-PAB-MMAE or maleimido-caproyl-val-cit-PAB-MMAE using a human IgG1 partially reduced to an average of 4 thiols per antibody (resulting in drug:antibody ratio of 4). These two ADCs were dosed at 2 mg/kg in Sprague-Dawley rats, and blood samples were taken at seven timepoints and processed to plasma. These plasma samples, along with standards of each ADC for the preparation of a calibration curve, were subjected to the mAb Select resin capture and papain release procedure described example 10 above to measure the concentration of antibody-conjugated MMAE. Antibody-conjugated drug concentrations were higher for the ADC prepared with the self-stabilizing drug-linker, with the magnitude of the difference increasing with time (data not shown). Initial antibody-conjugated drug concentrations are superimposable, reflecting the equivalence of the dose and drug:antibody ratio of the ADCs. However, divergence is observed within the first day, reaching a two-fold difference by day 3. These higher concentrations resulted in an approximately 40% greater antibody-conjugated drug AUC for the self-stabilized ADC relative to the maleimido-caproyl ADC Example 13

Toxicology

To assess the impact of self-stabilizing maleimides on toxicology, ADCs were prepared with 4 drugs per antibody of either maleimido-DPR-val-cit-PAB-MMAE or maleimido-caproyl-val-cit-PAB-MMAE using a humanized IgG1 (which has no known binding to any rat antigen) partially reduced to an average of 4 thiols per antibody (resulting in an average drug:antibody ratio of 4). These ADCs were dosed intravenously in female CD®IGS rats (Charles River Laboratories) at 10 mg/kg (6 rats per test article plus 6 rats receiving vehicle only). Prior to dosing and at 3 post-dose timepoints, blood samples were taken for hematology and serum chemistry analysis for biomarkers of toxicity. Neutropenia induced by the MMAE ADC appeared less severe for the self-stabilized conjugate than for the maleimido-caproyl ADC (data not shown).

Example 14

Plasma Concentration of Released Drug

The toxicology experiment described in example 13 above also included blood draws at one hour and 24 hours post-dose, which along with the 4 day and 7 day post-dose samples were analyzed for unconjugated MMAE in plasma by LC-MS/MS. The results of this analysis indicated that peak concentrations of circulating MMAE are about 2-fold lower for the self-stabilizing maleimido-DPR-val-cit-PAB-MMAE ADC relative to the maleimido-caproyl-val-cit-PAB-MMAE (data not shown).

Example 15

Xenograft Activity

Figure 11:
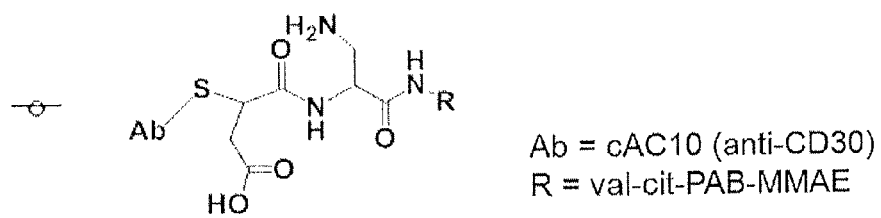
FIG. 11 illustrates the antitumor activity of ADCs in a murine xenograft model of ALCL (Karpas-299 cell line). ADCs were prepared with the anti-CD30 antibody cAC10 and drug linkers containing the val-cit-PAB-MMAE cytotoxic payload linked to the antibody via either a maleimido-caproyl group (closed circles) or a self-stabilizing maleimido-DPR group (open circles). Tumors were allowed to reach a volume of approximately 250 mm³ before dosing at 1 mg/kg weekly for three doses (six mice per dose group). The self-stabilizing ADC dose group experienced complete responses (no detectable tumor) in all six animals, with five animals experiencing durable regressions, while the maleimido-caproyl ADC experienced no complete responses.
Figure 11:
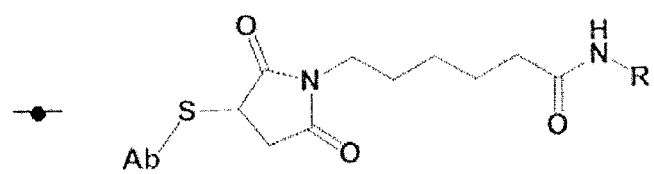
Figure 11:
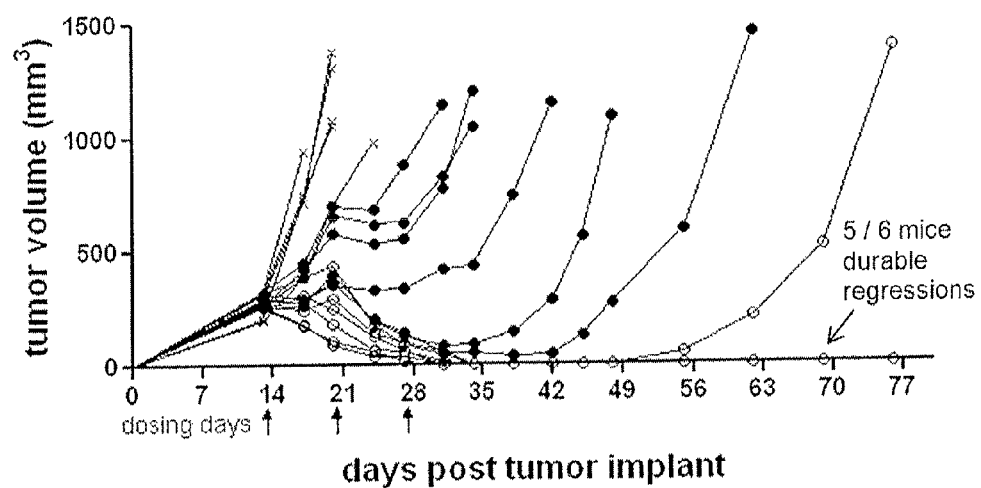

To evaluate the impact of self-stabilizing drug-linkers on the antitumor activity of ADCs, conjugates were prepared with the anti-CD30 antibody cAC10 using drug-linkers containing the val-cit-PAB-MMAE cytotoxic payload linked to the antibody via either a maleimido-caproyl group or a self-stabilizing maleimido-DPR group. These ADCs were evaluated in two separate murine xenograft models of CD30+ human malignancies. In the first model (FIG. 11), Karpas-299 (human ALCL) cells were implanted subcutaneously in female SCID mice and tumors were allowed to grow a volume of approximately 250 mm³ before dosing at 1 mg/kg weekly for three doses (six mice per dose group). All six mice dosed with the maleimido-caproyl ADC experienced some tumor growth delay relative to the untreated group, and two animals experienced partial tumor shrinkage; however, all tumors grew out and the entire group was euthanized with large tumors. The self-stabilizing ADC dose group experienced complete responses (no detectable tumor) in all six animals, with five animals experiencing durable regressions for the course of the study and only one animal sacrificed after its tumor had returned on study day 55. The results of this study indicate a significantly greater in vivo antitumor activity for the ADC prepared with the self-stabilizing drug-linker. In the second model, L428 (human Hodgkin Lymphoma) cells were implanted subcutaneously in female NSG mice and tumors were allowed to grow a volume of approximately 100 mm³ before dosing at 1 mg/kg every four days for four doses (six mice per dose group). All animals in both ADC dose groups experienced significant growth delay during treatment, however all tumors began growing out after study day 28 with no significant difference between maleimido-caproyl and self-stabilizing ADCs. Thus, the improvement in antitumor activity observed with the self-stabilizing ADC in xenograft studies appears to be model-dependent.

What is claimed is:

1. A Ligand-Functional Agent Conjugate having the formula:

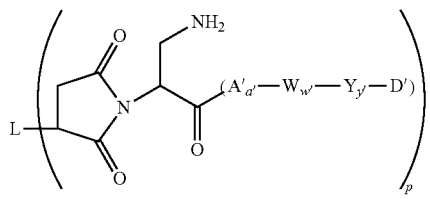

or a salt thereof, wherein
L is a Ligand unit directly attached to the succinimide ring of the Functional Agent Conjugate via a thioether linkage;
D' is a Drug unit;
the subscript p ranges from 1 to 20;
—W— is an optional Cleavable unit,
the subscript w' is 0 or 1;
—Y— is an optional Spacer unit,
the subscript y' is 0 or 1;
A' is an optional Stretcher unit; and
the subscript a' is 0 or 1.

2. A Ligand-Functional Agent Conjugate of claim 1, or a pharmaceutically acceptable salt thereof; wherein
L is an antibody.

3. A Ligand-Functional Agent Conjugate of claim 1 wherein p is 1 to 12.

4. A Ligand-Functional Agent Conjugate of claim 1 wherein p is 1 to 8.

5. A Ligand-Functional Agent Conjugate of claim 1 wherein a' is 0, and $W_{w'}$ is a dipeptide.

6. A Ligand-Functional Agent Conjugate of claim 1 wherein D' is a cytotoxic agent.

7. A Ligand-Functional Agent Conjugate of claim 1 wherein D' is an auristatin selected from the group consisting of AE, AFP, AEB, AEVB, MMAF and MMAE.

8. A Ligand-Functional Agent Conjugate of claim 1 wherein $W_{w'}$ is selected from the group consisting of Val-Cit, Phe-Lys and Val-Ala.

9. A Ligand-Functional Agent Conjugate of claim 1 wherein $Y_{y'}$ is a PAB unit.

10. A Ligand-Functional Agent Conjugate of claim 2 wherein the antibody is a monoclonal antibody.

11. A Ligand-Functional Agent Conjugate of claim 1 wherein the subscript a' is 0; $W_{w'}$ is Val-Cit; and $Y_{y'}$ is PAB.

12. A Ligand-Functional Agent Conjugate of claim 1 wherein the subscript a' is 0; $W_{w'}$ is Val-Cit; $Y_{y'}$ is PAB; and D' is a cytotoxic agent.

13. A Ligand-Functional Agent Conjugate of claim 1 wherein the subscript a' is 0; $W_{w'}$ is Val-Cit; $Y_{y'}$ is PAB; D' is a cytotoxic agent; and p is 1 to 8.

14. A Ligand-Functional Agent Conjugate of claim 1, wherein D' is MMAE.

15. A Ligand-Functional Agent Conjugate of claim 1, wherein the subscript a' is 0; $W_{w'}$ is Val-Cit; $Y_{y'}$ is PAB; and D' is MMAE.

* * * * *